US011946081B2

(12) United States Patent
Babe et al.

(10) Patent No.: US 11,946,081 B2
(45) Date of Patent: Apr. 2, 2024

(54) ***BACILLUS GIBSONII*-CLADE SERINE PROTEASES**

(71) Applicant: DANISCO US INC., Palo Alto, CA (US)

(72) Inventors: Lilia Maria Babe, Emerald Hills, CA (US); Lydia Dankmeyer, Rotterdam (NL); Frits Goedegebuur, Vlaardingen (NL); Thijs Kaper, Half Moon Bay, CA (US); Harm Mulder, Voorhout (NL); Sina Pricelius, Leiden (NL)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 16/471,686

(22) PCT Filed: Dec. 19, 2017

(86) PCT No.: PCT/US2017/067356

§ 371 (c)(1),
(2) Date: Jun. 20, 2019

(87) PCT Pub. No.: WO2018/118950

PCT Pub. Date: Jun. 28, 2018

(65) Prior Publication Data

US 2019/0330610 A1 Oct. 31, 2019

Related U.S. Application Data

(60) Provisional application No. 62/437,509, filed on Dec. 21, 2016.

(51) Int. Cl.
*C12N 9/54* (2006.01)
*C11D 3/386* (2006.01)

(52) U.S. Cl.
CPC ............ *C12N 9/54* (2013.01); *C11D 3/38681* (2013.01); *C12Y 304/21062* (2013.01)

(58) Field of Classification Search
None
See application file for complete search history.

(56) References Cited

U.S. PATENT DOCUMENTS

| | | | | |
|---|---|---|---|---|
| 6,287,841 | B1 | 9/2001 | Mulleners et al. | |
| 2005/0113273 | A1 | 5/2005 | Weber et al. | |
| 2019/0330610 | A1* | 10/2019 | Babe .................. | C11D 3/38681 |
| 2020/0392477 | A1* | 12/2020 | Babe ........................ | C12N 9/54 |

FOREIGN PATENT DOCUMENTS

| | | | |
|---|---|---|---|
| WO | 2011/027170 | A2 | 3/2011 |
| WO | 2012/151480 | A2 | 11/2012 |
| WO | 2015/089447 | A2 | 6/2015 |
| WO | 2016/205755 | A1 | 12/2016 |
| WO | 2017/219011 | A1 | 12/2017 |

OTHER PUBLICATIONS

Felix Jakob et al., Surface charge engineering of a Bacillus gibsonii subtilisin protease, Appl Microbiol Biotechnol. Aug. 2013; pp. 6793-6802; vol. 97(15) (Abstract Only).

Ronny Martinez et al., Increasing activity and thermal resistance of Bacillus gibsonii alkaline protease (BgAP) by directed evolution (Abstract Only).

International Search Report and Written Opinion—PCT/US2017/067356—dated May 18, 2018.

* cited by examiner

*Primary Examiner* — Hope A Robinson

(57) ABSTRACT

Disclosed herein is one or more subtilisin variant. nucleic acid encoding same. and compositions and methods related to the production and use thereof. including one or more *Bacillus gibsonii*-clade subtilisin variant that has improved soil removal compared to one or more reference subtilisin.

9 Claims, No Drawings

Specification includes a Sequence Listing.

*BACILLUS GIBSONII*-CLADE SERINE PROTEASES

Disclosed herein is one or more subtilisin variant, nucleic acid encoding same, and compositions and methods related to the production and use thereof, including one or more subtilisin variant that has improved soil removal compared to one or more reference subtilisin. Compositions containing the serine proteases are suitable for use in cleaning fabrics and hard surfaces, as well as in a variety of industrial applications.

REFERENCE TO SEQUENCE LISTING SUBMITTED ELECTRONICALLY

The content of the sequence listing electronically submitted with the application as an ASCII text file (Name: 20171219_NB41228WOPCT_ST25; Size: 15.3 KB; Created: Dec. 19, 2017) forms part of the application and is hereby incorporated herein by reference in its entirety.

Serine proteases are enzymes (EC No. 3.4.21) possessing an active site serine that initiates hydrolysis of peptide bonds of proteins. There are two broad categories of serine proteases, based on their structure: chymotrypsin-like (trypsin-like) and subtilisin-like. The prototypical subtilisin (EC No. 3.4.21.62) was initially obtained from *B. subtilis*. Subtilisins and their homologues are members of the S8 peptidase family of the MEROPS classification scheme. Members of family S8 have a catalytic triad in the order Asp, His and Ser in their amino acid sequence.

Although serine proteases have long been known in the art of industrial enzymes, there remains a need for further serine proteases that are suitable for particular conditions and uses.

The present variants, compositions and methods relate to recombinant serine proteases variants, compositions comprising such variants and methods related thereto. Compositions containing the *B. gibsonii*-clade serine proteases disclosed herein are suitable for use in cleaning fabrics and hard surfaces, as well as in a variety of industrial applications.

Some embodiments are directed to one or more subtilisin variant comprising an amino acid sequence comprising two, three, or four or more substitutions at positions corresponding to SEQ ID NO:1 positions selected from: (i) 99, 126, 127, 128, and 54; (ii) 99, 126, 127, and 128; (iii) S99A/E/H/I/K/M/N/Q/R/T/V, S126A/D/E/F/G/H/I/L/M/N/Q/R/T/V/W/Y, D127A/E/F/G/H/I/L/MN/P/Q/S/T/V/W/Y, F128A/C/D/E/G/H/I/K/L/M/N/P/Q/R/S/T/V/W, and P54E/G/I/L/Q/S/T/V; (iv) S99A/E/H/I/K/M/N/Q/R/T, S126A/D/E/G/I/L/MN/Q/R/T/V/W/Y, D127A/E/F/G/H/I/L/M/N/P/Q/S/T/V/W/Y, and F128A/C/D/E/G/H/I/K/L/M/N/P/Q/R/S/T/V/W; (v) S99E/H/I/K/M/Q/R/T, S126A/D/E/G/L/M/Q/V/Y, D127A/E/G/I/L/N/P/Q/S/T/V/W/Y, F128A/C/D/E/G/H/I/L/M/N/P/Q/S/T/V/W, and P54T; (vi) S99E/H/I/K/M/Q/R/T, S126A/D/E/G/L/M/Q/V/Y, D127A/E/G/I/L/N/P/Q/S/T/V/W/Y, and F128A/C/D/E/G/H/I/L/M/N/P/Q/S/T/V/W; (vii) S99E/H/I/K/M/R/T, S126A/G/M/N/T/V/Y, D127A/E/G/L/N/P/Q/S/T/V/W, F128A/C/D/E/G/I/L/M/N/Q/S/T/WW, and P54T; (viii) S99E/H/I/K/M/R/T, S126A/G/M/N/T/V/Y, D127A/E/G/L/N/P/Q/S/T/V/W, and F128A/C/D/E/G/I/L/M/N/Q/S/T/V/W; (ix) S99E/H/I/M/R/T, S126A/G/M/T, D127A/E/G/L/N/P/S/T/V, F128A/C/D/E/G/I/N/Q/S/T/W, and P54T; (x) S99E/H/I/M/R/T, S126A/G/M/T, D127A/E/G/L/N/P/S/T/V, and F128A/C/D/E/G/I/N/Q/S/T/W; (xi) S99M, S126A/G, D127E, and F128C/D/E/G; (xii) S126A/G, D127E, and F128E/G; or (xiii) S99M, S126A, D127E, and F128C/D/E; and wherein the amino acid positions of the variant are numbered by correspondence with the amino acid sequence of SEQ ID NO:1.

Another embodiment is directed to a method for increasing the production of a subtilisin variant in a Gram positive bacterial host cell, the method comprising: (a) introducing into a host cell a polynucleotide construct encoding a subtilisin variant comprising one or more substitutions at one or more positions corresponding to SEQ ID NO:1, wherein the position corresponding to N242 of SEQ ID NO:1 is substituted with an aspartic acid (D) (N242D), and (b) growing the host cell under conditions suitable for the production of the encoded subtilisin variant, wherein the host cell produces an increased amount of the subtilisin variant of (a) relative to a Gram positive host cell of the same genus, species and genetic background comprising an introduced polynucleotide construct encoding a subtilisin variant that does not comprise a substitution at the position corresponding to N242 of SEQ ID NO:1; and wherein the amino acid positions of the variant are numbered by correspondence with the amino acid sequence of SEQ ID NO:1.

In another embodiment, one or more subtilisin variant described herein (i) is a member of the *B. gibsonii*-clade; (ii) is isolated, (iii) has proteolytic activity; or comprises a combination of (i) to (iii). In a still further embodiment, one or more subtilisin variant described herein comprises an amino acid sequence with (i) 70%, 75%, 80%, 85%, 86%, 87%, 88%, 89%, 90%, 91%, 92%, 93%, 94%, 95%, 96%, 97%, 98%, 99% or less than 100% amino acid sequence identity to the amino acid sequence of SEQ ID NO:1 or 8; (ii) 85%, 86%, 87%, 88%, 89%, 90%, 91%, 92%, 93%, 94%, 95%, 96%, 97%, 98%, 99% or less than 100% amino acid sequence identity to the amino acid sequence of SEQ ID NO:1 or 8; (iii) 94%, 95%, 96%, 97%, 98%, 99%, or less than 100% amino acid sequence identity to the amino acid sequence of SEQ ID NO:1; (iv) 95%, 96%, 97%, 98%, 99%, or less than 100% amino acid sequence identity to the amino acid sequence of SEQ ID NO:8; or (v) 95%, 96%, 97%, 98%, 99%, or 100% amino acid sequence identity to the amino acid sequence of SEQ ID NO:8. In yet a still further embodiment, one or more subtilisin variant described herein has an increase in HDL, egg stain, and/or crème brûlée stain cleaning activity when compared to the HDL, egg stain, and/or crème brûlée stain cleaning activity of a protease with the amino acid sequence of SEQ ID NO:1

Another embodiment is directed to a composition comprising one or more subtilisin variant described herein. Some embodiments are directed to a method of cleaning, comprising contacting a surface or an item with one or more subtilisin variant described herein or one or more composition described herein. In further embodiments, the method of cleaning is directed to a method of cleaning a crème brûlée stain or an egg yolk stain, or both. Other embodiments are directed to a method for producing a variant described herein, comprising stably transforming a host cell with an expression vector comprising a polynucleotide encoding one or more subtilisin variant described herein. Still further embodiments are directed to a polynucleotide comprising a nucleic acid sequence encoding one or more subtilisin variant described herein.

Described herein are variants, compositions and methods relating to recombinant serine proteases. Compositions containing the serine proteases disclosed herein are suitable for use in cleaning fabrics and hard surfaces, as well as in a variety of industrial applications, such as, for example, textile, leather and feather processing. At least one serine protease disclosed herein is also well suited for inclusion in compositions for protein degradation, including but not limited to laundry and dishwashing detergents; personal care compositions; and human food and animal feed.

Prior to describing the present compositions and methods in detail, the following terms are defined for clarity. Terms and abbreviations not defined should be accorded their ordinary meaning as used in the art. Unless defined otherwise herein, all technical and scientific terms used herein have the same meaning as commonly understood by one of ordinary skill in the art. Unless otherwise indicated, the practice of the present disclosure involves conventional techniques commonly used in molecular biology, protein engineering, and microbiology. Although any methods and materials similar or equivalent to those described herein find use in the practice of the present disclosure, some suitable methods and materials are described herein. The terms defined immediately below are more fully described by reference to the Specification as a whole.

As used herein, the singular "a," "an" and "the" includes the plural unless the context clearly indicates otherwise. Unless otherwise indicated, nucleic acid sequences are written left to right in 5' to 3' orientation; and amino acid sequences are written left to right in amino to carboxy orientation. It is to be understood that this disclosure is not limited to the particular methodology, protocols, and reagents described herein, absent an indication to the contrary.

It is intended that every maximum numerical limitation given throughout this Specification includes every lower numerical limitation, as if such lower numerical limitations were expressly written herein. Every minimum numerical limitation given throughout this Specification will include every higher numerical limitation, as if such higher numerical limitations were expressly written herein. Every numerical range given throughout this Specification will include every narrower numerical range that falls within such broader numerical range, as if such narrower numerical ranges were all expressly written herein.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

The amino acid substitutions described herein use one or more following nomenclatures: position; position: amino acid substitution(s); or starting amino acid:position:amino acid substitution(s). Reference to only a "position" (i.e. 5, 8, 17, 22, etc) encompasses any starting amino acid that may be present in a reference polypeptide, parent or wild-type molecule at that position and any amino acid with which such starting amino acid may be substituted (i.e., amino acid substitutions exclude the starting amino acid of such reference polypeptide, parent or wild-type molecule). Reference to a position can be recited several forms, for example, position 003 can also be referred to as position 3. Reference to an amino acid substitution may be further expressed as several substituted amino acids separated by a foreslash ("/"). For example, D275S/K indicates position 275 is substituted with serine (S) or lysine (K). By way of further example, S101F/G/H/T/V represents five possible substitutions at position 101, wherein the starting amino acid serine (S) can be substituted with a phenylalanine (F), glycine (G), histidine (H), threonine (T), or valine (V). Reference to an X as the amino acid in a position, refers to any amino acid at the recited position.

The position of an amino acid residue in a given amino acid sequence is numbered by correspondence with the amino acid sequence of SEQ ID NO:1. That is, the amino acid sequence of SEQ ID NO:1 serves as a reference sequence. For example, the amino acid sequence of a *B. gibsonii*-clade subtilisin, which is further described in International Patent Application No. PCT/US2014/070107 filed Jun. 17, 2016, or one or more subtilisin variant described herein is aligned with the amino acid sequence of SEQ ID NO:1 using an alignment algorithm as described herein, and each amino acid residue in the given amino acid sequence that aligns (preferably optimally aligns) with an amino acid residue in SEQ ID NO:1 is conveniently numbered by reference to the numerical position of that corresponding amino acid residue. Sequence alignment algorithms, such as, for example, described herein will identify the location where insertions or deletions occur in a subject sequence when compared to a query sequence.

The term "mutation" refers to any change or alteration in an amino acid sequence, including the substitution of an amino acid at the identified position of an amino acid sequence with an amino acid that is different from the starting amino acid, deletion of an amino acid at the identified position of an amino acid sequence, insertion of an amino acid at the identified position of an amino acid sequence, replacement of an amino acid side chain in an amino acid sequence, and or chemical modification of an amino acid sequence.

The terms, "wild-type" or "parental" with respect to a polypeptide, refer to a naturally-occurring polypeptide that does not include a man-made substitution, insertion, or deletion at one or more amino acid positions. Similarly, the terms "wild-type" or "parental,", with respect to a polynucleotide, refer to a naturally-occurring polynucleotide that does not include a man-made substitution, insertion, or deletion at one or more nucleosides. A polynucleotide encoding a wild-type or parental polypeptide is, however, not limited to a naturally-occurring polynucleotide, and encompasses any polynucleotide encoding the wild-type or parental polypeptide.

The term "naturally-occurring" refers to, for example, a sequence and residues contained therein (e.g., polypeptide sequence and amino acids contained therein or nucleic acid sequence and nucleic acids contained therein) that are found in nature. Conversely, the term "non-naturally occurring" refers to, for example, a sequence and residues contained therein (e.g., polypeptide sequences and amino acids contained therein or nucleic acid sequence and nucleic acids contained therein) that are not found in nature.

Unless otherwise indicated, the term "reference", with respect to a polypeptide of the present disclosure refers to the polypeptide having the amino acid sequence of SEQ ID NO: 1. In one embodiment, the position of an amino acid residue in a given amino acid sequence is numbered by correspondence with the amino acid sequence of SEQ ID NO:1. In other embodiments, the polypeptide of SEQ ID NO: 1 serves as a reference polypeptide for comparison to the subtilisin variant of the present disclosure in stability and performance assays.

The terms "protease" and "proteinase" refer to an enzyme that has the ability to break down proteins and peptides. A protease has the ability to conduct "proteolysis," by hydrolysis of peptide bonds that link amino acids together in a peptide or polypeptide chain forming the protein. This activity of a protease as a protein-digesting enzyme is referred to as "proteolytic activity." Many well-known procedures exist for measuring proteolytic activity. For example, proteolytic activity may be ascertained by comparative assays that analyze the respective protease's ability to hydrolyze a suitable substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO99/34011 and U.S. Pat. No. 6,376,450). The pNA peptidyl assay (See e.g., Del Mar et al., Anal Biochem, 99:316-320, 1979) also finds use in determining the active enzyme concentration. This assay measures the rate at which p-nitroaniline is released as the enzyme hydrolyzes a soluble synthetic substrate, such as succinyl-alanine-alanine-proline-phenylalanine-p-nitroanilide (suc-AAPF-pNA). The rate of production of yellow color from the hydrolysis reaction is measured at 410 nm on a spectrophotometer and is proportional to the active enzyme concentration. In addition, absorbance measurements at 280 nanometers (nm) can be used to determine the total protein concentration in a sample of purified protein. The activity on substrate/protein concentration gives the enzyme specific activity.

The phrase "subtilisin variant" refers to a recombinant polypeptide that is derived from a parent or reference polypeptide by the substitution, insertion, or deletion, of one or more amino acids.

The phrase "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. gibsonii, B. pabuli, B. cereus, B. agaradhaerens, B akibai, B. clarkii*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores under stressful environmental conditions is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

The term "vector" refers to a nucleic acid construct used to introduce or transfer nucleic acid(s) into a target cell or tissue. A vector is typically used to introduce foreign DNA into a cell or tissue. Vectors include plasmids, cloning vectors, bacteriophages, viruses (e.g., viral vector), cosmids, expression vectors, shuttle vectors, and the like. A vector typically includes an origin of replication, a multicloning site, and a selectable marker. The process of inserting a vector into a target cell is typically referred to as transformation. The present invention includes, in some embodiments, a vector that comprises a DNA sequence encoding a serine protease polypeptide (e.g., precursor or mature serine protease polypeptide) that is operably linked to a suitable prosequence (e.g., secretory, signal peptide sequence, etc.) capable of effecting the expression of the DNA sequence in a suitable host, and the folding and translocation of the recombinant polypeptide chain.

The term "expression" refers to the transcription and stable accumulation of sense (mRNA) or anti-sense RNA, derived from a nucleic acid molecule of the disclosure. Expression may also refer to translation of mRNA into a polypeptide. Thus, the term "expression" includes any step involved in the "production of the polypeptide" including, but not limited to, transcription, post-transcriptional modifications, translation, post-translational modifications, secretion and the like.

The phrases "increased expression of a subtilisin variant", "increased production of a subtilisin variant" and "increased productivity of a subtilisin variant" are used interchangeably and refer to an increase in the yield of the subtilisin (variant) polypeptide as isolated or secreted from a recombinant host cell in which a polynucleotide encoding the subtilisin variant has been introduced (e.g., via transformation). More particularly, as used herein the phrases "increased expression of a subtilisin variant" or "increased production of a subtilisin variant" refer to an increase in the yield (i.e., protein productivity) of a specific subtilisin variant (polypeptide) as isolated or secreted from a recombinant host cell (i.e., into which a polynucleotide encoding the subtilisin variant has been introduced), where the "increase" in yield of the subtilisin variant polypeptide is relative (vis-à-vis) to a reference (control) subtilisin polypeptide as isolated or secreted from an analogous recombinant host cell (into which the polynucleotide encoding the reference (control) subtilisin polypeptide has been introduced). For example, a first polynucleotide encoding a subtilisin variant polypeptide of the disclosure and a second polynucleotide encoding a reference (control) subtilisin can be transformed into a population of host cells (i.e., a host cell population of the same genus, species, and genetic background). Subsequently, host cell transformants comprising the first polynucleotide and host cell transformants comprising the second polynucleotide are grown/cultured under identical conditions, and the amount of the subtilisin variant polypeptide and the reference (control) subtilisin polypeptide expressed/produced from the host cells are compared vis-à-vis each other (e.g., via protein concentration or subtilisin activity measurements).

The term "expression cassette," "expression plasmid" or "expression vector" refers to a nucleic acid construct or vector generated recombinantly or synthetically for the expression of a nucleic acid of interest in a target cell. An expression vector or expression cassette typically comprises a promoter nucleotide sequence that drives expression of the foreign nucleic acid. The expression vector or cassette also typically includes any other specified nucleic acid elements that permit transcription of a particular nucleic acid in a target cell. A recombinant expression cassette can be incorporated into a plasmid, chromosome, mitochondrial DNA, plastid DNA, virus, or nucleic acid fragment. Many prokaryotic and eukaryotic expression vectors are commercially available.

The term "plasmid" refers to an extrachromosomal DNA molecule which is capable of replicating independently from the chromosomal DNA. A plasmid is double stranded (ds) and may be circular and is typically used as a cloning vector.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, electroporation, conjugation, and transduction. Transformation refers to the genetic alteration of a cell which results from the uptake, optional genomic incorporation, and expression of genetic material (e.g., DNA).

As used herein, a nucleic acid is "operably linked" with another nucleic acid sequence when it is placed into a functional relationship with another nucleic acid sequence. For example, a promoter or enhancer is operably linked to a nucleotide coding sequence if the promoter affects the transcription of the coding sequence. A ribosome binding site may be operably linked to a coding sequence if it is positioned so as to facilitate translation of the coding sequence. Typically, "operably linked" DNA sequences are contiguous. However, enhancers do not have to be contiguous. Linking is accomplished by ligation at convenient restriction sites. If such sites do not exist, synthetic oligonucleotide adaptors or linkers may be used in accordance with conventional practice.

The term "gene" refers to a polynucleotide (e.g., a DNA segment), that encodes a polypeptide and includes regions preceding and following the coding regions. In some instances, a gene includes intervening sequences (introns) between individual coding segments (exons).

The term "recombinant" when used with reference to a cell typically indicates that the cell has been modified by the introduction of a foreign nucleic acid sequence or that the cell is derived from a cell so modified. For example, a recombinant cell may comprise a gene not found in identical form within the native (non-recombinant) form of the cell, or a recombinant cell may comprise a native gene (found in the native form of the cell) that has been modified and re-introduced into the cell. A recombinant cell may comprise a nucleic acid endogenous to the cell that has been modified without removing the nucleic acid from the cell; such modifications include those obtained by gene replacement, site-specific mutation, and related techniques known to those of ordinary skill in the art. Recombinant DNA technology includes techniques for the production of recombinant DNA in vitro and transfer of the recombinant DNA into cells where it may be expressed or propagated, thereby producing a recombinant polypeptide. "Recombination" and "recombining" of polynucleotides or nucleic acids refer generally to the assembly or combining of two or more nucleic acid or polynucleotide strands or fragments to generate a new polynucleotide or nucleic acid.

A nucleic acid or polynucleotide is said to "encode" a polypeptide if, in its native state or when manipulated by methods known to those of skill in the art, it can be transcribed and/or translated to produce the polypeptide or a fragment thereof. The anti-sense strand of such a nucleic acid is also said to encode the sequence.

The terms "host strain" and "host cell" refer to a suitable host for an expression vector comprising a DNA sequence of interest.

A "protein" or "polypeptide" comprises a polymeric sequence of amino acid residues. The terms "protein" and "polypeptide" are used interchangeably herein. The single and 3-letter code for amino acids as defined in conformity with the IUPAC-IUB Joint Commission on Biochemical Nomenclature (JCBN) is used throughout this disclosure. The single letter X refers to any of the twenty amino acids. It is also understood that a polypeptide may be coded for by more than one nucleotide sequence due to the degeneracy of the genetic code. Mutations can be named by the one letter code for the parent amino acid, followed by a position number and then the one letter code for the variant amino acid. For example, mutating glycine (G) at position 87 to serine (S) is represented as "G087S" or "G87S.

The terms "prosequence" or "propeptide sequence" refer to an amino acid sequence between the signal peptide sequence and mature protease sequence that is necessary for the proper folding and secretion of the protease; they are sometimes referred to as intramolecular chaperones. Cleavage of the prosequence or propeptide sequence results in a mature active protease. Bacterial serine proteases are often expressed as pro-enzymes. Examples of modified propeptides are provided, for example, in WO 2016/205710.

The terms "signal sequence" and "signal peptide" refer to a sequence of amino acid residues that may participate in the secretion or direct transport of the mature or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "mature" when used in describing a protein, polypeptide, or peptide refers to the functional form of the protein, polypeptide, or peptide without the signal peptide sequence and propeptide sequence.

The term "precursor" when used in describing a protein or peptide refers to a mature form of the protein having a prosequence operably linked to the amino or carbonyl terminus of the protein. The precursor may also have a "signal" sequence operably linked to the amino terminus of the prosequence. The precursor may also have additional polypeptides that are involved in post-translational activity (e.g., polypeptides cleaved therefrom to leave the mature form of a protein or peptide).

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related proteins or a reference protein.

The term "derived from" encompasses the terms "originated from," "obtained from," "obtainable from," "isolated from," and "created from" and generally indicates that the specified material comes from another specified material or has features that can be described with reference to the other specified material.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question. To exemplify, "proteases derived from *Bacillus*" refers to those enzymes having proteolytic activity that are naturally produced by *Bacillus*, as well as to serine proteases like those produced by *Bacillus* sources but which through the use of genetic engineering techniques are produced by other host cells transformed with a nucleic acid encoding the serine proteases.

The term "identical" in the context of two polynucleotide or polypeptide sequences refers to the nucleic acids or amino acids in the two sequences that are the same when aligned for maximum correspondence, as measured using sequence comparison or analysis algorithms.

The terms "% identity", "percent identity", and "PID" refer to protein sequence identity. Percent identity may be determined using standard techniques known in the art. Useful algorithms include the BLAST algorithms (See, Altschul et al., J Mol Biol, 215:403-410, 1990; and Karlin and Altschul, Proc Natl Acad Sci USA, 90:5873-5787, 1993). The BLAST program uses several search parameters, most of which are set to the default values. The NCBI BLAST algorithm finds the most relevant sequences in terms of biological similarity but is not recommended for query sequences of less than 20 residues (Altschul et al., Nucleic Acids Res, 25:3389-3402, 1997; and Schaffer et al., Nucleic Acids Res, 29:2994-3005, 2001). Exemplary default BLAST parameters for a nucleic acid sequence searches include: Neighboring words threshold=11; E-value cutoff=10; Scoring Matrix=NUC.3.1 (match=1, mismatch=−3); Gap Opening=5; and Gap Extension=2. Exemplary default BLAST parameters for amino acid sequence searches include: Word size=3; E-value cutoff=10; Scoring Matrix=BLOSUM62; Gap Opening=11; and Gap extension=1. A percent (%) amino acid sequence identity value is determined by the number of matching identical residues divided by the total number of residues of the "reference" sequence including any gaps created by the program for optimal/maximum alignment. BLAST algorithms refer to the "reference" sequence as the "query" sequence.

The phrases "homologous proteins" or "homologous proteases" refer to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST with threshold (E-value cut-off) at 0.001. (Altschul S F, Madde T L, Shaffer A A, Zhang J, Zhang Z, Miller W, Lipman D J. Gapped BLAST and PSI BLAST a new generation of protein database search programs. Nucleic Acids Res 1997 Set 1; 25(17):3389-402). Using this information, proteins sequences can be grouped. A phylogenetic tree can be built using the amino acid sequences. Amino acid sequences can be entered in a program such as the Vector NTI Advance suite and a Guide Tree can be created using the Neighbor Joining (NJ) method (Saitou and Nei, Mol Biol Evol, 4:406-425, 1987). The tree construction can be calculated using Kimura's correction for sequence distance and ignoring positions with gaps. A program such as AlignX can display the calculated distance values in parenthesis following the molecule name displayed on the phylogenetic tree.

Understanding the homology between molecules can reveal the evolutionary history of the molecules as well as information about their function; if a newly sequenced protein is homologous to an already characterized protein, there is a strong indication of the new protein's biochemical function. The most fundamental relationship between two entities is homology; two molecules are said to be homologous if they have been derived from a common ancestor. Homologous molecules, or homologs, can be divided into two classes, paralogs and orthologs. Paralogs are homologs that are present within one species. Paralogs often differ in their detailed biochemical functions. Orthologs are homologs that are present within different species and have very similar or identical functions. A protein superfamily is the largest grouping (clade) of proteins for which common ancestry can be inferred. Usually this common ancestry is based on sequence alignment and mechanistic similarity. Superfamilies typically contain several protein families which show sequence similarity within the family. The term "protein clan" is commonly used for protease superfamilies based on the MEROPS protease classification system. As used herein, the term "subtilisin" includes any member of the S8 serine protease family as described in MEROPS—The Peptidase Data base (Rawlings et al., MEROPS: the peptidase database, Nucl Acids Res, 34 Database issue, D270-272, 2006).

The CLUSTAL W algorithm is another example of a sequence alignment algorithm (See, Thompson et al., Nucleic Acids Res, 22:4673-4680, 1994). Default parameters for the CLUSTAL W algorithm include: Gap opening penalty=10.0; Gap extension penalty=0.05; Protein weight matrix=BLOSUM series; DNA weight matrix=TUB; Delay divergent sequences %=40; Gap separation distance=8; DNA transitions weight=0.50; List hydrophilic residues=GPSNDQEKR; Use negative matrix=OFF; Toggle Residue specific penalties=ON; Toggle hydrophilic penalties=ON; and Toggle end gap separation penalty=OFF. In CLUSTAL algorithms, deletions occurring at either terminus are included. For example, a variant with a five amino acid deletion at either terminus (or within the polypeptide) of a polypeptide of 500 amino acids would have a percent sequence identity of 99% (495/500 identical residues×100) relative to the "reference" polypeptide. Such a variant would be encompassed by a variant having "at least 99% sequence identity" to the polypeptide. The MUSCLE program (Robert C. Edgar. MUSCLE: multiple sequence alignment with high accuracy and high throughput Nucl. Acids Res. (2004) 32 (5): 1792-1797) is yet another example of a multiple sequence alignment algorithm.

A nucleic acid or polynucleotide is "isolated" when it is at least partially or completely separated from other components, including but not limited to for example, other proteins, nucleic acids, cells, etc. Similarly, a polypeptide, protein or peptide is "isolated" when it is at least partially or completely separated from other components, including but not limited to for example, other proteins, nucleic acids, cells, etc. On a molar basis, an isolated species is more abundant than are other species in a composition. For example, an isolated species may comprise at least about 60%, about 65%, about 70%, about 75%, about 80%, about 85%, about 90%, about 91%, about 92%, about 93%, about 94%, about 95%, about 96%, about 97%, about 98%, about 99%, or about 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a nucleic acid or a protein sample, respectively, followed by visualization upon staining. If desired, a high-resolution technique, such as high performance liquid chromatography (HPLC) or a similar means can be utilized for purification of the material.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

The phrase "composition(s) substantially-free of boron" or "detergent(s) substantially-free of boron" refers to composition(s) or detergent(s), respectively, that contain trace amounts of boron, for example, less than about 1000 ppm (1 mg/kg or liter equals 1 ppm), less than about 100 ppm, less than about 50 ppm, less than about 10 ppm, or less than about 5 ppm, or less than about 1 ppm, perhaps from other compositions or detergent constituents.

As used herein, the term "functional assay" refers to an assay that provides an indication of a protein's activity. In some embodiments, the term refers to assay systems in which a protein is analyzed for its ability to function in its usual capacity. For example, in the case of a protease, a functional assay involves determining the effectiveness of the protease to hydrolyze a proteinaceous substrate.

The term "cleaning activity" refers to a cleaning performance achieved by a serine protease polypeptide or reference protease under conditions prevailing during the proteolytic, hydrolyzing, cleaning, or other process of the disclosure. In some embodiments, cleaning performance of a serine protease polypeptide or reference protease may be determined by using various assays for cleaning one or more various enzyme sensitive stains on an item or surface (e.g., a stain resulting from food, grass, blood, ink, milk, oil, crème brûlée, and/or egg protein). Cleaning performance of a variant or reference protease can be determined by subjecting the stain on the item or surface to standard wash condition(s) and assessing the degree to which the stain is removed by using various chromatographic, spectrophotometric, or other quantitative methodologies. Exemplary cleaning assays and methods are known in the art and include, but are not limited to those described in WO99/34011 and U.S. Pat. No. 6,605,458, both of which are herein incorporated by reference, as well as those cleaning assays and methods included in the Examples provided below.

The term "cleaning effective amount" of a serine protease polypeptide or reference protease refers to the amount of protease that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, tablet, bar) composition is required, etc.

The term "cleaning adjunct material" refers to any liquid, solid, or gaseous material included in cleaning composition other than a serine protease polypeptide of the disclosure. In some embodiments, the cleaning compositions of the present disclosure include one or more cleaning adjunct materials. Each cleaning adjunct material is typically selected depending on the particular type and form of cleaning composition (e.g., liquid, granule, powder, bar, paste, spray, tablet, gel, foam, or other composition). Preferably, each cleaning adjunct material is compatible with the protease enzyme used in the composition.

Cleaning compositions and cleaning formulations include any composition that is suited for cleaning, bleaching, disinfecting, and/or sterilizing any object, item, and/or surface. Such compositions and formulations include, but are not limited to for example, liquid and/or solid compositions, including cleaning or detergent compositions (e.g., liquid, tablet, gel, bar, granule, and/or solid laundry cleaning or detergent compositions and fine fabric detergent compositions; hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwashing compositions (e.g., "hand" or "manual" dishwashing detergents) and automatic dishwashing compositions (e.g., "automatic dishwashing detergents"). Single dosage unit forms also find use with the present invention, including but not limited to pills, tablets, gelcaps, or other single dosage units such as pre-measured powders or liquids.

Cleaning composition or cleaning formulations, as used herein, include, unless otherwise indicated, granular or powder-form all-purpose or heavy-duty washing agents, especially cleaning detergents; liquid, granular, gel, solid, tablet, paste, or unit dosage form all-purpose washing agents, especially the so-called heavy-duty liquid (HDL) detergent or heavy-duty dry (HDD) detergent types; liquid fine-fabric detergents; hand or manual dishwashing agents, including those of the high-foaming type; hand or manual dishwashing, automatic dishwashing, or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries, such as bleach additives and "stain-stick" or pre-treat types. In some embodiments, granular compositions are in "compact" form; in some embodiments, liquid compositions are in a "concentrated" form.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., non-fabric) surface cleaning compositions, including, but not limited to for example, hand or manual or automatic dishwashing detergent compositions, oral cleaning compositions, denture cleaning compositions, contact lens cleaning compositions, wound debridement compositions, and personal cleansing compositions.

The phrase "detergent composition" or "detergent formulation" is used in reference to a composition intended for use in a wash medium for the cleaning of soiled or dirty objects, including particular fabric and/or non-fabric objects or items. Such compositions of the present disclosure are not limited to any particular detergent composition or formulation. Indeed, in some embodiments, the detergents of the disclosure comprise at least one serine protease polypeptide of the disclosure and, in addition, one or more surfactants, transferase(s), hydrolytic enzymes, oxido reductases, builders (e.g., a builder salt), bleaching agents, bleach activators, bluing agents, fluorescent dyes, caking inhibitors, masking agents, enzyme stabilizers, calcium, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some compositions of the disclosure, such as, but not limited to, cleaning compositions or detergent compositions, do not contain any phosphate (e.g., phosphate salt or phosphate builder).

The term "bleaching" refers to the treatment of a material (e.g., fabric, laundry, pulp, etc.) or surface for a sufficient length of time and/or under appropriate pH and/or temperature conditions to effect a brightening (i.e., whitening) and/or cleaning of the material. Examples of chemicals suitable for bleaching include, but are not limited to, for example, $ClO_2$, $H_2O_2$, peracids, $NO_2$, etc. Bleaching agents also include enzymatic bleaching agents such as perhydrolase and arylesterases. Another embodiment is directed to a composition comprising one or more subtilisin variant described herein, and one or more perhydrolase, such as, for example, is described in WO2005/056782, WO2007/106293, WO 2008/063400, WO2008/106214, and WO2008/106215.

The phrase "wash performance" of a protease (e.g., a serine protease polypeptide of the disclosure) refers to the contribution of a serine protease polypeptide to washing that provides additional cleaning performance to the detergent as compared to the detergent without the addition of the serine protease polypeptide to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

The term "relevant washing conditions" is used herein to indicate the conditions, particularly washing temperature, time, washing mechanics, sud concentration, type of detergent and water hardness, actually used in households in a hand dishwashing, automatic dishwashing, or laundry detergent market segment.

The term "disinfecting" refers to the removal of contaminants from surfaces, as well as the inhibition or killing of microbes on the surfaces of items.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, the filler salt is sodium sulfate.

Disclosed herein is one or more subtilisin variant useful for cleaning applications and in methods of cleaning, as well as in a variety of industrial applications. In one embodiment, one or more serine protease or subtilisin variant described herein is a member of the *B. gibsonii*-clade. In another embodiment, one or more subtilisin variant described herein is an isolated, recombinant, substantially pure, and/or non-naturally occurring polypeptide. In some embodiments, one or more subtilisin variant described herein can be incorporated into one or more cleaning composition useful in one or more method of cleaning an item or a surface in need thereof.

Some embodiments are directed to one or more subtilisin variant comprising an amino acid sequence comprising two, three, or four or more substitutions at positions corresponding to SEQ ID NO:1 positions selected from: (i) 99, 126, 127, 128, and 54; (ii) 99, 126, 127, and 128; (iii) S99A/E/H/I/K/M/N/Q/R/T, S126A/D/E/G/I/L/M/N/Q/R/T/V/W/Y, D127A/E/F/G/H/I/L/M/N/P/Q/S/T/V/W/Y, F128A/C/D/E/G/H/I/K/L/M/N/P/Q/R/S/T/V/W, and P54T; (iv) S99A/E/H/I/K/M/N/Q/R/T, S126A/D/E/G/I/L/M/N/Q/R/T/V/W/Y, D127A/E/F/G/H/I/L/M/N/P/Q/S/T/V/W/Y, and F128A/C/D/E/G/H/I/K/L/M/N/P/Q/R/S/T/V/W; (v) S99E/H/I/K/M/Q/R/T, S126A/D/E/G/L/M/Q/V/Y, D127A/E/G/I/L/N/P/Q/S/T/V/W/Y, F128A/C/D/E/G/H/I/L/M/N/P/Q/S/T/V/W, and P54T; (vi) S99E/H/I/K/M/Q/R/T, S126A/D/E/G/L/M/Q/V/Y, D127A/E/G/I/L/N/P/Q/S/T/V/W/Y, and F128A/C/D/E/G/H/I/L/M/N/P/Q/S/T/V/W; (vii) S99E/H/I/K/M/R/T, S126A/G/M/N/T/V/Y, D127A/E/G/L/N/P/Q/S/T/V/W, F128A/C/D/E/G/I/L/M/N/Q/S/T/V/W, and P54T; (viii) S99E/H/I/K/M/R/T, S126A/G/M/N/T/V/Y, D127A/E/G/L/N/P/Q/S/T/V/W, and F128A/C/D/E/G/I/L/M/N/Q/S/T/V/W; (ix) S99E/H/I/M/R/T, S126A/G/M/T, D127A/E/G/L/N/P/S/T/V, F128A/C/D/E/G/I/N/Q/S/T/W, and P54T; (x) S99E/H/I/M/R/T, S126A/G/M/T, D127A/E/G/L/N/P/S/T/V, and F128A/C/D/E/G/I/N/Q/S/T/W; (xi) S99M, S126A/G, D127E, and F128C/D/E/G; (xii) S126A/G, D127E, and F128E/G; or (xiii) S99M, S126A, D127E, and F128C/D/E; and wherein the amino acid positions of the variant are numbered by correspondence with the amino acid sequence of SEQ ID NO:1. Yet other embodiments are directed to one or more subtilisin variant comprising an amino acid sequence comprising two, three, or four or more substitutions at positions corresponding to SEQ ID NO:1 positions selected from: (i) 99, 126, 127, 128, and 54; (ii) 99, 126, 127, and 128; (iii) S99A/E/H/I/K/M/N/Q/R/T, S126A/D/E/G/I/L/M/N/Q/R/T/V/W/Y, D127A/E/F/G/H/I/L/M/N/P/Q/S/T/V/W/Y, F128A/C/D/E/G/H/I/K/L/M/N/P/Q/R/S/T/V/W, and P54T; (iv) S99A/E/H/I/K/M/N/Q/R/T, S126A/D/E/G/I/L/M/N/Q/R/T/V/W/Y, D127A/E/F/G/H/I/L/M/N/P/Q/S/T/V/W/Y, and F128A/C/D/E/G/H/I/K/L/M/N/P/Q/R/S/T/V/W; (v) S99E/H/I/K/M/Q/R/T, S126A/D/E/G/L/M/Q/V/Y, D127A/E/G/I/L/N/P/Q/S/T/V/W/Y, F128A/C/D/E/G/H/I/L/M/N/P/Q/S/T/V/W, and P54T; (vi) S99E/H/I/K/M/Q/R/T, S126A/D/E/G/L/M/Q/V/Y, D127A/E/G/I/L/N/P/Q/S/T/V/W/Y, and F128A/C/D/E/G/H/I/L/M/N/P/Q/S/T/V/W; (vii) S99E/H/I/K/M/R/T, S126A/G/M/N/T/V/Y, D127A/E/G/L/N/P/Q/S/T/V/W, F128A/C/D/E/G/I/L/M/N/Q/S/T/V/W, and P54T; (viii) S99E/H/I/K/M/R/T, S126A/G/M/N/T/V/Y, D127A/E/G/L/N/P/Q/S/T/V/W, and F128A/C/D/E/G/I/L/M/N/Q/S/T/V/W; (ix) S99E/H/I/M/R/T, S126A/G/M/T, D127A/E/G/L/N/P/S/T/V, F128A/C/D/E/G/I/N/Q/S/T/W, and P54T; (x) S99E/H/I/M/R/T, S126A/G/M/T, D127A/E/G/L/N/P/S/T/V, and F128A/C/D/E/G/I/N/Q/S/T/W; (xi) S99M, S126A/G, D127E, and F128C/D/E/G; (xii) S126A/G, D127E, and F128E/G; or (xiii) S99M, S126A, D127E, and F128C/D/E; with the proviso that said variant does not contain a substitution that corresponds to: (a) S99R in SEQ ID NO:1 when said variant contains a substitution that corresponds to S126T or F128A in SEQ ID NO:1, (b) S126T in SEQ ID NO:1 when said variant contains a substitution that corresponds to S99R or F128A in SEQ ID NO:1, or (c) F128A in SEQ ID NO:1 when said variant contains a substitution that corresponds to S99R or S126T in SEQ ID NO:1, and wherein the amino acid positions of the variant are numbered by correspondence with the amino acid sequence of SEQ ID NO:1.

Other embodiments are directed to one or more subtilisin variant comprising an amino acid sequence comprising two, three, or four or more substitutions at positions corresponding to SEQ ID NO:1 positions selected from: (i) S99A/E/H/I/K/M/N/Q/T, S126A/D/E/G/I/L/M/N/Q/R/V/W/Y, D127A/E/F/G/H/I/L/M/N/P/Q/S/T/V/W/Y, F128C/D/E/G/H/I/K/L/M/N/P/Q/R/S/T/V/W, and P54T; (ii) S99A/E/H/I/K/M/N/Q/T, S126D/E/G/I/L/M/N/Q/R/T/V/W/Y, D127A/E/F/G/H/I/L/M/N/P/Q/S/T/V/W/Y, and F128/C/D/E/G/H/I/K/L/M/N/P/Q/R/S/T/V/W; (iii) S99E/H/I/K/M/Q/T, S126A/D/E/G/L/M/Q/V/Y, D127A/E/G/I/L/N/P/Q/S/T/V/W/Y, F128/C/D/E/G/H/I/L/M/N/P/Q/S/T/V/W, and P54T; (iv) S99E/H/I/K/M/Q/T, S126A/D/E/G/L/M/Q/V/Y, D127A/E/G/I/L/N/P/Q/S/T/V/W/Y, and F128C/D/E/G/H/I/L/M/N/P/Q/S/T/V/W; (v) S99E/H/I/K/M/T, S126A/G/M/N/V/Y, D127A/E/G/L/N/P/Q/S/T/V/W, F128C/D/E/G/I/L/M/N/Q/S/T/V/W, and P54T; (vi) S99E/H/I/K/M/T, S126A/G/M/N/V/Y, D127A/E/G/L/N/P/Q/S/T/V/W, and F128C/D/E/G/I/L/M/N/Q/S/T/V/W; (vii) S99E/H/I/M/T, S126A/G/M, D127A/E/G/L/N/P/S/T/V, F128C/D/E/G/I/N/Q/S/T/W, and P54T; (viii) S99E/H/I/M/T, S126A/G/M, D127A/E/G/L/N/P/S/T/V, and F128C/D/E/G/I/N/Q/S/T/W; (ix) S99M, S126A/G, D127E, and F128C/D/E/G; (x) S126A/G, D127E, and F128E/G; or (xi) S99M, S126A, D127E, and F128C/D/E; wherein the amino acid positions of the variant are numbered by correspondence with the amino acid sequence of SEQ ID NO:1.

Still other embodiments are directed to one or more subtilisin variant described herein, wherein said variant further comprises one, two, three, four, or more substitutions at positions corresponding to SEQ ID NO:1 positions selected from: (i) 37, 39, 43, 47, 56, 80, 85, 87, 114, and 242; (ii) 37, 39, 47, 56, 80, 85, 87, 114, and 242; (iii) 39 in combination with one or more positions corresponding to SEQ ID NO:1 positions selected from 37, 47, 56, 80, 85, 87, 114, and 242; (iv) 56 in combination with one or more positions corresponding to SEQ ID NO:1 positions selected from 37, 39, 47, 80, 85, 87, 114, and 242; (v) 114 in combination with one or more positions corresponding to SEQ ID NO:1 positions selected from 37, 39, 47, 56, 80, 85, 87, and 242; (vi) 242 in combination with one or more positions corresponding to SEQ ID NO:1 positions selected from 37, 39, 47, 56, 80, 85, 87, and 114; (vii) 39+242 in combination with one or more positions corresponding to SEQ ID NO:1 positions selected from 37, 47, 56, 80, 85, 87, and 114; (viii) 39+99+128 in combination with one or more positions corresponding to SEQ ID NO:1 positions selected from 37, 47, 56, 80, 85, 87, 114, and 242; or (ix) 39, 242, 39+242, 37+39+242, 37+39+47+56+80+85+87+114+242, and 37+39+43+47+56+80+85+87+114+242; wherein the amino acid positions of the variant are numbered by correspondence with the amino acid sequence of SEQ ID NO:1. Yet another embodiment is directed to one or more subtilisin variant described herein, wherein said variant further comprises one, two, three, four, or more substitutions at positions corresponding to SEQ ID NO:1 positions selected from: (i) A37T, S39E, I43V, A47V, T56Y, I80V, N85S, E87D, T114Q, and N242D; (ii) A37T, S39E, A47V, T56Y, I80V, N85S, E87D, T114Q, and N242D; (iii) S39E in combination with one or more positions corresponding to SEQ ID NO:1 positions selected from A37T, A47V, T56Y, I80V, N85S, E87D, T114Q, and N242D; (iv) T56Y in combination with one or more positions corresponding to SEQ ID NO:1 positions selected from A37T, S39E, A47V, I80V, N85S, E87D, T114Q, and N242D; (v) T114Q in combination with one or more positions corresponding to SEQ ID NO:1 positions selected from A37T, S39E, A47V, T56Y, I80V, N85S, E87D, and N242D; (vi) N242D in combination with one or more positions corresponding to SEQ ID NO:1 positions selected from A37T, S39E, A47V, T56Y, I80V, N85S, E87D, and T114Q; (vii) S39E+N242D in combination with one or more positions corresponding to SEQ ID NO:1 positions selected from A37T, A47V, T56Y, I80V, N85S, E87D, and T114Q; or (viii) S39E, N242D, S39E+N242D, A37T+539E+N242D, A37T+S39E+A47V+T56Y+I80V+N85S+E87D+T114Q+N242D, and A37T+539E+143V+A47V+T56Y+I80V+N85S+E87D+T114Q+N242D; wherein the amino acid positions of the variant are numbered by correspondence with the amino acid sequence of SEQ ID NO:1.

Yet another embodiment is directed to one or more subtilisin variant comprising an amino acid sequence comprising two, three, or four or more substitutions at positions corresponding to SEQ ID NO:1 positions selected from: (i) A37T-539E-I43V-A47V-T56Y-I80V-N85S-E87D-599R-T114Q-S126T-F128A-N242D, A37T-539E-I43V-A47V-T56Y-I80V-N85S-E87D-599T-T114Q-S126G-N242D, A37T-539E-I43V-A47V-T56Y-I80V-N85S-E87D-599R-T114Q-S126V-D127G-A128E-F128A-N242D, A37T-539E-I43V-A47V-T56Y-I80V-N85S-E87D-S99I-T114Q-S126T-D127E-F1281-N242D, A37T-539E-I43V-A47V-T56Y-I80V-N85 S-E87D-599H-T114Q-D127S-F128Q-N242D, A37T-539E-I43V-A47V-T56Y-I80V-N85S-E87D-599N-T114Q-S126T-D127Q-N242D, A37T-539E-I43V-A47V-T56Y-I80V-N85S-E87D-599H-T114Q-D127Q-F128N-N242D, A37T-539E-I43V-A47V-T56Y-I80V-N85S-E87D-599T-T114Q-S126G-D127G-F128V-N242D, A37T-539E-I43V-A47V-T56Y-I80V-N85S-E87D-S99K-T114Q-S126G-D127G-F128G-N242D, A37T-539E-I43V-A47V-T56Y-I80V-N85S-E87D-T114Q-D127L-F128V-N242D, A37T-539E-I43V-A47V-T56Y-I80V-N85S-E87D-599M-T114Q-D127G-F128S-N242D, A37T-539E-I43V-A47V-T56Y-I80V-N85S-E87D-599K-T114Q-D127L-F128C-N242D, A37T-539E-I43V-A47V-T56Y-I80V-N85S-E87D-599M-T114Q-S126E-D127A-F128S-N242D, A37T-539E-I43V-A47V-T56Y-I80V-N85S-E87D-T114Q-D127P-F128E-N242D, A37T-539E-I43V-A47V-T56Y-I80V-N85S-E87D-599A-T114Q-S126M-D127S-F128A-N242D, A37T-S39E-I43V-A47V-T56Y-I80V-N85S-E87D-S99H-T114Q-D127G-F128G-N242D, A37T-S39E-I43V-A47V-T56Y-I80V-N85S-E87D-S99T-T114Q-S126V-D127E-F128K-N242D, A37T-S39E-I43V-A47V-T56Y-I80V-N85S-E87D-S99T-T114Q-S126G-D127G-F128T-N242D, A37T-S39E-I43V-A47V-T56Y-I80V-N85S-E87D-S99Q-T114Q-S126T-D127V-F128D-N242D, A37T-S39E-I43V-A47V-T56Y-I80V-N85 S-E87D-T114Q-S126T-D127L-F128 S-N242D, A37T-S39E-I43V-A47V-T56Y-I80V-N85S-E87D-T114Q-S126T-D127G-F128V-N242D, A37T-S39E-I43V-A47V-T56Y-I80V-N85S-E87D-T114Q-S126R-F128A-N242D, A37T-S39E-I43V-A47V-T56Y-I80V-N85S-E87D-T114Q-S126A-D127S-F128A-N242D, A37T-S39E-I43V-A47V-T56Y-I80V-N85S-E87D-T114Q-D127G-F128L-N242D, A37T-S39E-I43V-A47V-T56Y-I80V-N85S-E87D-T114Q-S126G-D127A-F128G-N242D, A37T-S39E-I43V-A47V-T56Y-I80V-N85S-E87D-T114Q-D127G-F128Q-N242D, A37T-539E-I43V-A47V-T56Y-I80V-N85S-E87D-T114Q-S126M-D127S-F128A-N242D, A37T-539E-I43V-A47V-T56Y-I80V-N85S-E87D-T114Q-S126M-D127A-F128W-N242D, A37T-539E-I43V-A47V-T56Y-I80V-N85S-E87D-T114Q-S126A-D127H-F128V-N242D, A37T-539E-I43V-A47V-T56Y-I80V-N85S-E87D-T114Q-D127T-F128T-N242D, A37T-539E-I43V-A47V-T56Y-I80V-N85S-E87D-T114Q-S126A-D127V-F128T-N242D, A37T-539E-I43V-A47V-T56Y-I80V-N85S-E87D-T114Q-S126A-D127L-F128N-N242D, A37T-539E-I43V-A47V-T56Y-I80V-N85S-E87D-T114Q-D127Q-F128M-N242D, A37T-539E-I43V-A47V-T56Y-I80V-N85S-E87D-T114Q-S126G-D127T-F128E-N242D, A37T-539E-I43V-A47V-T56Y-I80V-N85S-E87D-T114Q-D127Q-F128S-N242D, A37T-539E-I43V-A47V-T56Y-I80V-N85S-E87D-T114Q-D127N-F128G-

N242D, A37T-539E-143V-A47V-T56Y-I80V-N85S-E87D-T114Q-D127L-F128N-N242D, A37T-539E-I43V-A47V-T56Y-I80V-N85S-E87D-T114Q-D127V-F128T-N242D, A37T-539E-I43V-A47V-T56Y-I80V-N85 S-E87D-T114Q-D127V-F128 S-N242D, A37T-539E-I43V-A47V-T56Y-I80V-N85S-E87D-T114Q-S126M-D127V-F128G-N242D, A37T-539E-I43V-A47V-T56Y-I80V-N85S-E87D-T114Q-S126A-D127G-F128N-N242D, A37T-539E-I43V-A47V-T56Y-I80V-N85S-E87D-T114Q-S126L-D127F-F128R-N242D, A37T-539E-I43V-A47V-T56Y-I80V-N85S-E87D-T114Q-S126G-D127V-F128G-N242D, A37T-539E-I43V-A47V-T56Y-I80V-N85S-E87D-T114Q-S126V-D127M-F128S-N242D, A37T-539E-I43V-A47V-T56Y-I80V-N85S-E87D-T114Q-S126A-D127W-F128G-N242D, A37T-539E-I43V-A47V-T56Y-I80V-N85S-E87D-T114Q-S126A-D127S-F128S-N242D, A37T-539E-I43V-A47V-T56Y-I80V-N85S-E87D-T114Q-S126M-D127S-F128T-N242D, A37T-539E-I43V-A47V-T56Y-I80V-N85S-E87D-T114Q-D127A-F128V-N242D, A37T-S39E-I43V-A47V-T56Y-I80V-N85S-E87D-T114Q-S126Q-D127L-F128H-N242D, A37T-S39E-I43V-A47V-T56Y-I80V-N85S-E87D-S99R-T114Q-S126M-D127P-F128E-N242D, A37T-539E-I43V-A47V-T56Y-I80V-N85S-E87D-599R-T114Q-F128E-N242D, A37T-539E-I43V-A47V-T56Y-I80V-N85S-E87D-599R-T114Q-S126L-D127H-F128E-N242D, A37T-539E-I43V-A47V-T56Y-I80V-N85S-E87D-599R-T114Q-S126M-D127L-F128E-N242D, A37T-539E-I43V-A47V-T56Y-I80V-N85S-E87D-599R-T114Q-D127E-F128G-N242D, A37T-539E-I43V-A47V-T56Y-I80V-N85S-E87D-599R-T114Q-S126E-D127A-F128S-N242D, A37T-539E-I43V-A47V-T56Y-I80V-N85S-E87D-599R-T114Q-S126Q-D127V-F128C-N242D, A37T-539E-I43V-A47V-T56Y-I80V-N85S-E87D-599R-T114Q-S126N-D127G-F128G-N242D, A37T-539E-I43V-A47V-T56Y-I80V-N85 S-E87D-599R-T114Q-S126T-D127E-F128E-N242D, A37T-539E-I43V-A47V-T56Y-I80V-N85 S-E87D-599R-T114Q-S126D-D127S-F128A-N242D, A37T-539E-I43V-A47V-T56Y-I80V-N85S-E87D-599R-T114Q-S126W-D127N-F128D-N242D, A37T-539E-I43V-A47V-T56Y-I80V-N85S-E87D-599R-T114Q-S126A-D127E-F128G-N242D, A37T-539E-I43V-A47V-T56Y-I80V-N85S-E87D-599R-T114Q-D127A-F128C-N242D, A37T-539E-I43V-A47V-P54T-T56Y-I80V-N85S-E87D-599R-T114Q-S126T-D127E-F128A-N242D, A37T-539E-I43V-A47V-P54T-T56Y-I80V-N85S-E87D-599R-T114Q-D1271-F128T-N242D, A37T-539E-I43V-A47V-P54T-T56Y-I80V-N85S-E87D-599R-T114Q-S126L-D127G-F128E-N242D, A37T-S39E-I43V-A47V-P54T-T56Y-I80V-N85S-E87D-599R-T114Q-S126V-D127A-F128T-N242D, A37T-539E-I43V-A47V-P54T-T56Y-I80V-N85S-E87D-599R-T114Q-S126L-F128H-N242D, A37T-539E-I43V-A47V-P54T-T56Y-I80V-N85S-E87D-599R-T114Q-S126Q-D127A-F128D-N242D, A37T-539E-I43V-A47V-P54T-T56Y-I80V-N85S-E87D-599R-T114Q-S126L-D127T-F128Q-N242D, A37T-539E-I43V-A47V-P54T-T56Y-I80V-N85S-E87D-599R-T114Q-S126L-D127P-F128G-N242D, A37T-539E-I43V-A47V-P54T-T56Y-I80V-N85S-E87D-599R-T114Q-S1261-D127E-F128T-N242D, A37T-539E-I43V-A47V-P54T-T56Y-I80V-N85S-E87D-599R-T114Q-S126G-D127E-F128D-N242D, A37T-539E-I43V-A47V-P54T-T56Y-I80V-N85S-E87D-599R-T114Q-S126T-F128E-N242D, A37T-539E-I43V-A47V-P54T-T56Y-I80V-N85S-E87D-599R-T114Q-S126L-F128A-N242D, A37T-539E-I43V-A47V-P54T-T56Y-I80V-N85S-E87D-599R-T114Q-S126G-D127P-F128C-N242D, A37T-539E-I43V-A47V-P54T-T56Y-I80V-N85 S-E87D-599R-T114Q-D127S-F128 S-N242D, A37T-539E-I43V-A47V-P54T-T56Y-I80V-N85 S-E87D-599R-T114Q-S126D-D127G-F128A-N242D, A37T-539E-I43V-A47V-P54T-T56Y-I80V-N85S-E87D-599R-T114Q-S126A-D127W-F128E-N242D, A37T-539E-I43V-A47V-P54T-T56Y-I80V-N85S-E87D-S99R-T114Q-S126A-D127N-F128C-N242D, A37T-S39E-I43V-A47V-P54T-T56Y-I80V-N85S-E87D-S99R-T114Q-S126Y-F128L-N242D, A37T-S39E-I43V-A47V-P54T-T56Y-I80V-N85S-E87D-S99R-T114Q-S126A-D127S-F128S-N242D, A37T-S39E-I43V-A47V-P54T-T56Y-I80V-N85S-E87D-S99R-T114Q-D1271-F128S-N242D, A37T-S39E-I43V-A47V-P54T-T56Y-I80V-N85S-E87D-S99R-T114Q-D127G-F128P-N242D, A37T-S39E-I43V-A47V-P54T-T56Y-I80V-N85S-E87D-S99R-T114Q-D127G-F128E-N242D, A37T-S39E-I43V-A47V-P54T-T56Y-I80V-N85S-E87D-S99R-T114Q-D127T-F128A-N242D, A37T-S39E-I43V-A47V-P54T-T56Y-I80V-N85S-E87D-S99R-T114Q-S126T-D127Y-F128D-N242D, A37T-S39E-I43V-A47V-P54T-T56Y-I80V-N85S-E87D-S99R-T114Q-S126M-D127A-F128D-N242D, A37T-S39E-I43V-A47V-P54T-T56Y-I80V-N85S-E87D-S99R-T114Q-D127N-F128D-N242D, A37T-S39E-I43V-A47V-P54T-T56Y-I80V-N85S-E87D-S99R-T114Q-S126V-D127E-F128V-N242D, A37T-S39E-I43V-A47V-P54T-T56Y-I80V-N85S-E87D-S99R-T114Q-S126N-D127G-F128L-N242D, A37T-S39E-I43V-A47V-P54T-T56Y-I80V-N85S-E87D-S99R-T114Q-S126T-D127E-F128L-N242D, A37T-S39E-I43V-A47V-P54T-T56Y-I80V-N85S-E87D-S99R-T114Q-S126A-F128G-N242D, A37T-S39E-I43V-A47V-P54T-T56Y-I80V-N85S-E87D-S99R-T114Q-S126T-D127G-F128G-N242D, A37T-S39E-I43V-A47V-P54T-T56Y-I80V-N85S-E87D-S99R-T114Q-F128E-N242D, A37T-S39E-I43V-A47V-P54T-T56Y-I80V-N85S-E87D-S99R-T114Q-S126Y-D127E-F128G-N242D, A37T-S39E-I43V-A47V-P54T-T56Y-I80V-N85S-E87D-S99R-T114Q-S126A-F128Q-N242D, A37T-S39E-I43V-A47V-P54T-T56Y-I80V-N85S-E87D-S99R-T114Q-S126A-D127E-F128G-N242D, A37T-S39E-I43V-A47V-P54T-T56Y-I80V-N85S-E87D-S99R-T114Q-S126T-F128A-N242D, A37T-S39E-I43V-A47V-P54T-T56Y-I80V-N85S-E87D-S99E-T114Q-S126T-F128A-N242D, and A37T-S39E-I43V-A47V-T56Y-I80V-N85S-E87D-S99E-T114Q-D127E-F128G-N242D; (ii) A37T-S39E-I43V-A47V-T56Y-I80V-N85S-E87D-S99T-T114Q-S126G-N242D, A37T-S39E-I43V-A47V-T56Y-I80V-N85S-E87D-S99R-T114Q-S126V-D127G-A128E-F128A-N242D, A37T-S39E-I43V-A47V-T56Y-I80V-N85S-E87D-S99I-T114Q-S126T-D127E-F1281-N242D, A37T-S39E-I43V-A47V-T56Y-I80V-N85S-E87D-S99H-T114Q-D127S-F128Q-N242D, A37T-S39E-I43V-A47V-T56Y-I80V-N85S-E87D-S99N-T114Q-S126T-D127Q-N242D, A37T-S39E-I43V-A47V-T56Y-I80V-N85S-E87D-S99H-T114Q-D127Q-F128N-N242D, A37T-S39E-I43V-A47V-T56Y-I80V-N85S-E87D-S99T-T114Q-S126G-D127G-F128V-N242D, A37T-S39E-I43V-A47V-T56Y-I80V-N85S-E87D-S99K-T114Q-S126G-D127G-F128G-N242D, A37T-S39E-I43V-A47V-T56Y-I80V-N85S-E87D-T114Q-D127L-F128V-N242D, A37T-S39E-I43V-A47V-T56Y-I80V-N85 S-E87D-S99M-T114Q-D127G-F128 S-N242D, A37T-S39E-I43V-A47V-T56Y-I80V-N85S-E87D-S99K-T114Q-D127L-F128C-N242D, A37T-S39E-I43V-A47V-T56Y-I80V-N85 S-E87D-S99M-T114Q-S126E-D127A-F128 S-N242D, A37T-S39E-I43V-A47V-T56Y-I80V-N85S-E87D-T114Q-D127P-F128E-N242D, A37T-S39E-I43V-A47V-T56Y-I80V-N85S-E87D-S99A-T114Q-S126M-D127S-F128A-N242D, A37T-S39E-I43V-A47V-T56Y-I80V-N85S-E87D-S99H-T114Q-D127G-F128G-N242D, A37T-S39E-I43V-A47V-T56Y-I80V-N85S-E87D-S99T-T114Q-S126V-D127E-F128K-N242D, A37T-S39E-I43V-A47V-T56Y-I80V-N85S-E87D-S99T-T114Q-S126G-

D127G-F128T-N242D, A37T-S39E-I43V-A47V-T56Y-I80V-N85S-E87D-S99Q-T114Q-S126T-D127V-F128D-N242D, A37T-S39E-I43V-A47V-T56Y-I80V-N85 S-E87D-T114Q-S126T-D127L-F128 S-N242D, A37T-S39E-I43V-A47V-T56Y-I80V-N85S-E87D-T114Q-S126T-D127G-F128V-N242D, A37T-S39E-I43V-A47V-T56Y-I80V-N85S-E87D-T114Q-S126R-F128A-N242D, A37T-S39E-I43V-A47V-T56Y-I80V-N85S-E87D-T114Q-S126A-D127S-F128A-N242D, A37T-S39E-I43V-A47V-T56Y-I80V-N85S-E87D-T114Q-D127G-F128L-N242D, A37T-S39E-I43V-A47V-T56Y-I80V-N85S-E87D-T114Q-S126G-D127A-F128G-N242D, A37T-S39E-I43V-A47V-T56Y-I80V-N85S-E87D-T114Q-D127G-F128Q-N242D, A37T-539E-I43V-A47V-T56Y-I80V-N85S-E87D-T114Q-S126M-D127S-F128A-N242D, A37T-539E-I43V-A47V-T56Y-I80V-N85S-E87D-T114Q-S126M-D127A-F128W-N242D, A37T-539E-I43V-A47V-T56Y-I80V-N85S-E87D-T114Q-S126A-D127H-F128V-N242D, A37T-539E-I43V-A47V-T56Y-I80V-N85S-E87D-T114Q-D127T-F128T-N242D, A37T-539E-I43V-A47V-T56Y-I80V-N85S-E87D-T114Q-S126A-D127V-F128T-N242D, A37T-539E-I43V-A47V-T56Y-I80V-N85S-E87D-T114Q-S126A-D127L-F128N-N242D, A37T-539E-I43V-A47V-T56Y-I80V-N85 S-E87D-T114Q-D127Q-F128M-N242D, A37T-539E-I43V-A47V-T56Y-I80V-N85 S-E87D-T114Q-S126G-D127T-F128E-N242D, A37T-539E-I43V-A47V-T56Y-I80V-N85 S-E87D-T114Q-D127Q-F128 S-N242D, A37T-539E-I43V-A47V-T56Y-I80V-N85S-E87D-T114Q-D127N-F128G-N242D, A37T-539E-143V-A47V-T56Y-I80V-N85S-E87D-T114Q-D127L-F128N-N242D, A37T-539E-I43V-A47V-T56Y-I80V-N85S-E87D-T114Q-D127V-F128T-N242D, A37T-539E-I43V-A47V-T56Y-I80V-N85 S-E87D-T114Q-D127V-F128 S-N242D, A37T-539E-I43V-A47V-T56Y-I80V-N85S-E87D-T114Q-S126M-D127V-F128G-N242D, A37T-539E-I43V-A47V-T56Y-I80V-N85S-E87D-T114Q-S126A-D127G-F128N-N242D, A37T-539E-I43V-A47V-T56Y-I80V-N85S-E87D-T114Q-S126L-D127F-F128R-N242D, A37T-539E-I43V-A47V-T56Y-I80V-N85S-E87D-T114Q-S126G-D127V-F128G-N242D, A37T-539E-I43V-A47V-T56Y-I80V-N85S-E87D-T114Q-S126V-D127M-F128S-N242D, A37T-S39E-I43V-A47V-T56Y-I80V-N85S-E87D-T114Q-S126A-D127W-F128G-N242D, A37T-S39E-I43V-A47V-T56Y-I80V-N85S-E87D-T114Q-S126A-D127S-F128S-N242D, A37T-S39E-I43V-A47V-T56Y-I80V-N85S-E87D-T114Q-S126M-D127S-F128T-N242D, A37T-S39E-I43V-A47V-T56Y-I80V-N85S-E87D-T114Q-D127A-F128V-N242D, A37T-S39E-I43V-A47V-T56Y-I80V-N85S-E87D-T114Q-S126Q-D127L-F128H-N242D, A37T-S39E-I43V-A47V-T56Y-I80V-N85S-E87D-S99R-T114Q-S126M-D127P-F128E-N242D, A37T-539E-I43V-A47V-T56Y-I80V-N85S-E87D-599R-T114Q-F128E-N242D, A37T-539E-I43V-A47V-T56Y-I80V-N85S-E87D-599R-T114Q-S126L-D127H-F128E-N242D, A37T-539E-I43V-A47V-T56Y-I80V-N85S-E87D-599R-T114Q-S126M-D127L-F128E-N242D, A37T-539E-I43V-A47V-T56Y-I80V-N85S-E87D-599R-T114Q-D127E-F128G-N242D, A37T-539E-I43V-A47V-T56Y-I80V-N85S-E87D-599R-T114Q-S126E-D127A-F128S-N242D, A37T-539E-I43V-A47V-T56Y-I80V-N85S-E87D-599R-T114Q-S126Q-D127V-F128C-N242D, A37T-539E-I43V-A47V-T56Y-I80V-N85S-E87D-599R-T114Q-S126N-D127G-F128G-N242D, A37T-539E-I43V-A47V-T56Y-I80V-N85 S-E87D-599R-T114Q-S126T-D127E-F128E-N242D, A37T-539E-I43V-A47V-T56Y-I80V-N85 S-E87D-599R-T114Q-S126D-D127S-F128A-N242D, A37T-539E-I43V-A47V-T56Y-I80V-N85S-E87D-599R-T114Q-S126W-D127N-F128D-N242D, A37T-539E-I43V-A47V-T56Y-I80V-N85S-E87D-599R-T114Q-S126A-D127E-F128G-N242D, A37T-539E-I43V-A47V-T56Y-I80V-N85S-E87D-599R-T114Q-D127A-F128C-N242D, A37T-539E-I43V-A47V-P54T-T56Y-I80V-N85S-E87D-599R-T114Q-S126T-D127E-F128A-N242D, A37T-539E-I43V-A47V-P54T-T56Y-I80V-N85S-E87D-599R-T114Q-D1271-F128T-N242D, A37T-539E-I43V-A47V-P54T-T56Y-I80V-N85S-E87D-599R-T114Q-S126L-D127G-F128E-N242D, A37T-S39E-I43V-A47V-P54T-T56Y-I80V-N85S-E87D-599R-T114Q-S126V-D127A-F128T-N242D, A37T-539E-I43V-A47V-P54T-T56Y-I80V-N85S-E87D-599R-T114Q-S126L-F128H-N242D, A37T-539E-I43V-A47V-P54T-T56Y-I80V-N85S-E87D-599R-T114Q-S126Q-D127A-F128D-N242D, A37T-539E-I43V-A47V-P54T-T56Y-I80V-N85S-E87D-599R-T114Q-S126L-D127T-F128Q-N242D, A37T-539E-I43V-A47V-P54T-T56Y-I80V-N85S-E87D-599R-T114Q-S126L-D127P-F128G-N242D, A37T-539E-I43V-A47V-P54T-T56Y-I80V-N85S-E87D-599R-T114Q-S1261-D127E-F128T-N242D, A37T-539E-I43V-A47V-P54T-T56Y-I80V-N85S-E87D-599R-T114Q-S126G-D127E-F128D-N242D, A37T-539E-I43V-A47V-P54T-T56Y-I80V-N85S-E87D-599R-T114Q-S126T-F128E-N242D, A37T-539E-I43V-A47V-P54T-T56Y-I80V-N85S-E87D-599R-T114Q-S126L-F128A-N242D, A37T-539E-I43V-A47V-P54T-T56Y-I80V-N85S-E87D-S99R-T114Q-S126G-D127P-F128C-N242D, A37T-S39E-I43V-A47V-P54T-T56Y-I80V-N85S-E87D-S99R-T114Q-D127S-F128S-N242D, A37T-S39E-I43V-A47V-P54T-T56Y-I80V-N85S-E87D-S99R-T114Q-S126D-D127G-F128A-N242D, A37T-S39E-I43V-A47V-P54T-T56Y-I80V-N85S-E87D-S99R-T114Q-S126A-D127W-F128E-N242D, A37T-S39E-I43V-A47V-P54T-T56Y-I80V-N85S-E87D-S99R-T114Q-S126A-D127N-F128C-N242D, A37T-S39E-I43V-A47V-P54T-T56Y-I80V-N85S-E87D-S99R-T114Q-S126Y-F128L-N242D, A37T-S39E-I43V-A47V-P54T-T56Y-I80V-N85S-E87D-S99R-T114Q-S126A-D127S-F128S-N242D, A37T-S39E-I43V-A47V-P54T-T56Y-I80V-N85S-E87D-S99R-T114Q-D1271-F128S-N242D, A37T-S39E-I43V-A47V-P54T-T56Y-I80V-N85S-E87D-S99R-T114Q-D127G-F128P-N242D, A37T-S39E-I43V-A47V-P54T-T56Y-I80V-N85S-E87D-S99R-T114Q-D127G-F128E-N242D, A37T-S39E-I43V-A47V-P54T-T56Y-I80V-N85S-E87D-S99R-T114Q-D127T-F128A-N242D, A37T-S39E-I43V-A47V-P54T-T56Y-I80V-N85S-E87D-S99R-T114Q-S126T-D127Y-F128D-N242D, A37T-S39E-I43V-A47V-P54T-T56Y-I80V-N85S-E87D-S99R-T114Q-S126M-D127A-F128D-N242D, A37T-S39E-I43V-A47V-P54T-T56Y-I80V-N85S-E87D-S99R-T114Q-D127N-F128D-N242D, A37T-S39E-I43V-A47V-P54T-T56Y-I80V-N85S-E87D-S99R-T114Q-S126V-D127E-F128V-N242D, A37T-S39E-I43V-A47V-P54T-T56Y-I80V-N85S-E87D-S99R-T114Q-S126N-D127G-F128L-N242D, A37T-S39E-I43V-A47V-P54T-T56Y-I80V-N85S-E87D-S99R-T114Q-S126T-D127E-F128L-N242D, A37T-S39E-I43V-A47V-P54T-T56Y-I80V-N85S-E87D-S99R-T114Q-S126A-F128G-N242D, A37T-S39E-I43V-A47V-P54T-T56Y-I80V-N85S-E87D-S99R-T114Q-S126T-D127G-F128G-N242D, A37T-S39E-I43V-A47V-P54T-T56Y-I80V-N85S-E87D-S99R-T114Q-F128E-N242D, A37T-S39E-I43V-A47V-P54T-T56Y-I80V-N85S-E87D-S99R-T114Q-S126Y-D127E-F128G-N242D, A37T-S39E-I43V-A47V-P54T-T56Y-I80V-N85S-E87D-S99R-T114Q-S126A-F128Q-N242D, A37T-S39E-I43V-A47V-P54T-T56Y-I80V-N85S-E87D-S99R-T114Q-S126A-D127E-F128G-N242D, A37T-S39E-I43V-A47V-P54T-T56Y-I80V-N85S-E87D-S99R-T114Q-S126T-F128A-N242D, A37T-S39E-I43V-A47V-P54T-T56Y-I80V-N85S-E87D-S99E-T114Q-S126T-F128A-N242D, and A37T-S39E-I43V-A47V-T56Y-I80V-

N85S-E87D-S99E-T114Q-D127E-F128G-N242D; (iii) A37T-S39E-I43V-A47V-T56Y-I80V-N85S-E87D-S99R-T114Q-S126T-F128A-N242D, A37T-S39E-I43V-A47V-T56Y-I80V-N85S-E87D-S99T-T114Q-S126G-N242D, A37T-S39E-I43V-A47V-T56Y-I80V-N85S-E87D-S99R-T114Q-S126V-D127G-A128E-F128A-N242D, A37T-S39E-I43V-A47V-T56Y-I80V-N85S-E87D-S99I-T114Q-S126T-D127E-F1281-N242D, A37T-S39E-I43V-A47V-T56Y-I80V-N85S-E87D-S99H-T114Q-D127S-F128Q-N242D, A37T-S39E-I43V-A47V-T56Y-I80V-N85S-E87D-S99H-T114Q-D127Q-F128N-N242D, A37T-S39E-I43V-A47V-T56Y-I80V-N85 S-E87D-T114Q-D127L-F128V-N242D, A37T-S39E-I43V-A47V-T56Y-I80V-N85S-E87D-S99M-T114Q-D127G-F128S-N242D, A37T-S39E-I43V-A47V-T56Y-I80V-N85S-E87D-S99K-T114Q-D127L-F128C-N242D, A37T-S39E-I43V-A47V-T56Y-I80V-N85S-E87D-T114Q-D127P-F128E-N242D, A37T-S39E-I43V-A47V-T56Y-I80V-N85S-E87D-S99H-T114Q-D127G-F128G-N242D, A37T-S39E-I43V-A47V-T56Y-I80V-N85S-E87D-S99Q-T114Q-S126T-D127V-F128D-N242D, A37T-S39E-I43V-A47V-T56Y-I80V-N85S-E87D-T114Q-S126T-D127L-F128S-N242D, A37T-539E-I43V-A47V-T56Y-I80V-N85S-E87D-T114Q-S126A-D127S-F128A-N242D, A37T-539E-I43V-A47V-T56Y-I80V-N85S-E87D-T114Q-S126G-D127A-F128G-N242D, A37T-539E-I43V-A47V-T56Y-I80V-N85S-E87D-T114Q-D127G-F128Q-N242D, A37T-539E-I43V-A47V-T56Y-I80V-N85S-E87D-T114Q-S126M-D127A-F128W-N242D, A37T-539E-I43V-A47V-T56Y-I80V-N85S-E87D-T114Q-S126A-D127V-F128T-N242D, A37T-539E-I43V-A47V-T56Y-I80V-N85S-E87D-T114Q-S126A-D127L-F128N-N242D, A37T-539E-I43V-A47V-T56Y-I80V-N85S-E87D-T114Q-D127Q-F128M-N242D, A37T-539E-I43V-A47V-T56Y-I80V-N85S-E87D-T114Q-S126G-D127T-F128E-N242D, A37T-539E-I43V-A47V-T56Y-I80V-N85S-E87D-T114Q-D127Q-F128S-N242D, A37T-539E-I43V-A47V-T56Y-I80V-N85S-E87D-T114Q-D127N-F128G-N242D, A37T-539E-I43V-A47V-T56Y-I80V-N85S-E87D-T114Q-D127V-F128T-N242D, A37T-539E-143V-A47V-T56Y-I80V-N85S-E87D-T114Q-D127V-F128S-N242D, A37T-539E-I43V-A47V-T56Y-I80V-N85S-E87D-T114Q-S126A-D127G-F128N-N242D, A37T-539E-I43V-A47V-T56Y-I80V-N85S-E87D-T114Q-S126G-D127V-F128G-N242D, A37T-539E-I43V-A47V-T56Y-I80V-N85S-E87D-T114Q-S126A-D127S-F128S-N242D, A37T-539E-I43V-A47V-T56Y-I80V-N85S-E87D-T114Q-S126M-D127S-F128T-N242D, A37T-539E-I43V-A47V-T56Y-I80V-N85S-E87D-T114Q-D127A-F128V-N242D, A37T-539E-I43V-A47V-T56Y-I80V-N85 S-E87D-599R-T114Q-F128E-N242D, A37T-539E-I43V-A47V-T56Y-I80V-N85S-E87D-599R-T114Q-D127E-F128G-N242D, A37T-539E-I43V-A47V-T56Y-I80V-N85S-E87D-599R-T114Q-S126E-D127A-F128S-N242D, A37T-539E-I43V-A47V-T56Y-I80V-N85S-E87D-599R-T114Q-S126Q-D127V-F128C-N242D, A37T-539E-I43V-A47V-T56Y-I80V-N85S-E87D-599R-T114Q-S126T-D127E-F128E-N242D, A37T-539E-I43V-A47V-T56Y-I80V-N85S-E87D-599R-T114Q-S126D-D127S-F128A-N242D, A37T-539E-I43V-A47V-T56Y-I80V-N85 S-E87D-599R-T114Q-S126A-D127E-F128G-N242D, A37T-539E-I43V-A47V-T56Y-I80V-N85S-E87D-599R-T114Q-D127A-F128C-N242D, A37T-539E-I43V-A47V-P54T-T56Y-I80V-N85S-E87D-S99R-T114Q-S126T-D127E-F128A-N242D, A37T-S39E-I43V-A47V-P54T-T56Y-I80V-N85S-E87D-S99R-T114Q-S126L-D127G-F128E-N242D, A37T-S39E-I43V-A47V-P54T-T56Y-I80V-N85S-E87D-S99R-T114Q-S126V-D127A-F128T-N242D, A37T-S39E-I43V-A47V-P54T-T56Y-I80V-N85S-E87D-S99R-T114Q-S126L-F128H-N242D, A37T-S39E-I43V-A47V-P54T-T56Y-I80V-N85S-E87D-S99R-T114Q-S126L-D127T-F128Q-N242D, A37T-S39E-I43V-A47V-P54T-T56Y-I80V-N85 S-E87D-S99R-T114Q-S126L-D127P-F128G-N242D, A37T-S39E-I43V-A47V-P54T-T56Y-I80V-N85S-E87D-S99R-T114Q-S126G-D127E-F128D-N242D, A37T-S39E-I43V-A47V-P54T-T56Y-I80V-N85 S-E87D-S99R-T114Q-S126T-F128E-N242D, A37T-S39E-I43V-A47V-P54T-T56Y-I80V-N85S-E87D-S99R-T114Q-S126L-F128A-N242D, A37T-S39E-I43V-A47V-P54T-T56Y-I80V-N85 S-E87D-S99R-T114Q-S126G-D127P-F128C-N242D, A37T-S39E-I43V-A47V-P54T-T56Y-I80V-N85S-E87D-S99R-T114Q-D127S-F128S-N242D, A37T-S39E-I43V-A47V-P54T-T56Y-I80V-N85S-E87D-S99R-T114Q-S126A-D127W-F128E-N242D, A37T-S39E-I43V-A47V-P54T-T56Y-I80V-N85S-E87D-S99R-T114Q-S126A-D127N-F128C-N242D, A37T-539E-I43V-A47V-P54T-T56Y-I80V-N85S-E87D-599R-T114Q-S126Y-F128L-N242D, A37T-539E-I43V-A47V-P54T-T56Y-I80V-N85S-E87D-599R-T114Q-D1271-F128S-N242D, A37T-539E-I43V-A47V-P54T-T56Y-I80V-N85S-E87D-599R-T114Q-D127G-F128P-N242D, A37T-539E-I43V-A47V-P54T-T56Y-I80V-N85S-E87D-599R-T114Q-D127G-F128E-N242D, A37T-539E-I43V-A47V-P54T-T56Y-I80V-N85S-E87D-599R-T114Q-S126T-D127Y-F128D-N242D, A37T-539E-I43V-A47V-P54T-T56Y-I80V-N85S-E87D-599R-T114Q-S126M-D127A-F128D-N242D, A37T-539E-I43V-A47V-P54T-T56Y-I80V-N85S-E87D-599R-T114Q-S126V-D127E-F128V-N242D, A37T-539E-I43V-A47V-P54T-T56Y-I80V-N85S-E87D-599R-T114Q-S126T-D127E-F128L-N242D, A37T-S39E-I43V-A47V-P54T-T56Y-I80V-N85S-E87D-599R-T114Q-S126A-F128G-N242D, A37T-S39E-I43V-A47V-P54T-T56Y-I80V-N85S-E87D-599R-T114Q-F128E-N242D, A37T-539E-143V-A47V-P54T-T56Y-I80V-N85 S-E87D-599R-T114Q-S126Y-D127E-F128G-N242D, A37T-539E-I43V-A47V-P54T-T56Y-I80V-N85S-E87D-599R-T114Q-S126A-F128Q-N242D, A37T-539E-I43V-A47V-P54T-T56Y-I80V-N85 S-E87D-599R-T114Q-S126A-D127E-F128G-N242D, A37T-539E-I43V-A47V-P54T-T56Y-I80V-N85S-E87D-599E-T114Q-S126T-F128A-N242D, and A37T-539E-I43V-A47V-T56Y-I80V-N85S-E87D-599E-T114Q-D127E-F128G-N242D; (iv) A37T-539E-I43V-A47V-T56Y-I80V-N85 S-E87D-T114Q-S126A-D127S-F128A-N242D, A37T-539E-I43V-A47V-T56Y-I80V-N85 S-E87D-T114Q-S126M-D127S-F128A-N242D, A37T-539E-I43V-A47V-T56Y-I80V-N85 S-E87D-599R-T114Q-D127A-F128C-N242D, A37T-S39E-I43V-A47V-T56Y-I80V-N85S-E87D-S99R-T114Q-F128E-N242D, A37T-S39E-I43V-A47V-T56Y-I80V-N85S-E87D-S99R-T114Q-S126T-D127E-F128E-N242D, A37T-S39E-I43V-A47V-T56Y-I80V-N85 S-E87D-S99R-T114Q-S126V-D127G-A128E-F128A-N242D, A37T-S39E-I43V-A47V-T56Y-I80V-N85S-E87D-T114Q-D127P-F128E-N242D, A37T-S39E-I43V-A47V-T56Y-I80V-N85S-E87D-T114Q-S126G-D127T-F128E-N242D, A37T-S39E-I43V-A47V-T56Y-I80V-N85S-E87D-S99T-T114Q-S126G-N242D; A37T-S39E-143V-A47V-T56Y-I80V-N85S-E87D-T114Q-S126G-D127A-F128G-N242D, A37T-S39E-143V-A47V-T56Y-I80V-N85S-E87D-S99R-T114Q-S126A-D127E-F128G-N242D, A37T-S39E-I43V-A47V-T56Y-I80V-N85S-E87D-S99R-T114Q-D127E-F128G-N242D, A37T-S39E-143V-A47V-T56Y-I80V-N85S-E87D-S99T-T114Q-S126G-D127G-F128V-N242D, A37T-S39E-I43V-A47V-T56Y-I80V-N85S-E87D-S99R-T114Q-S126N-D127G-F128G-N242D, A37T-S39E-I43V-A47V-T56Y-I80V-N85S-E87D-S99H-T114Q-D127G-F128G-N242D, A37T-S39E-I43V-A47V-T56Y-I80V-N85S-E87D-T114Q-D127N-F128G-

N242D, A37T-S39E-I43V-A47V-T56Y-I80V-N85S-E87D-T114Q-S126G-D127V-F128G-N242D, A37T-S39E-I43V-A47V-T56Y-I80V-N85 S-E87D-S99I-T114Q-S126T-D127E-F1281-N242D, A37T-S39E-I43V-A47V-T56Y-I80V-N85S-E87D-T114Q-D127G-F128L-N242D, A37T-S39E-I43V-A47V-T56Y-I80V-N85S-E87D-T114Q-D127Q-F128M-N242D, A37T-S39E-I43V-A47V-T56Y-I80V-N85 S-E87D-T114Q-S126A-D127G-F128N-N242D, A37T-S39E-I43V-A47V-T56Y-I80V-N85 S-E87D-T114Q-S126A-D127L-F128N-N242D, A37T-S39E-I43V-A47V-T56Y-I80V-N85 S-E87D-T114Q-D127L-F128N-N242D, A37T-S39E-I43V-A47V-T56Y-I80V-N85S-E87D-S99H-T114Q-D127Q-F128N-N242D, A37T-S39E-I43V-A47V-T56Y-I80V-N85S-E87D-T114Q-D127G-F128Q-N242D, A37T-S39E-I43V-A47V-T56Y-I80V-N85S-E87D-S99H-T114Q-D127S-F128Q-N242D, A37T-S39E-I43V-A47V-T56Y-I80V-N85 S-E87D-S99M-T114Q-D127G-F128 S-N242D, A37T-S39E-I43V-A47V-T56Y-I80V-N85 S-E87D-T114Q-S126T-D127L-F128 S-N242D, A37T-S39E-I43V-A47V-T56Y-I80V-N85 S-E87D-T114Q-D127Q-F128 S-N242D, A37T-539E-I43V-A47V-T56Y-I80V-N85S-E87D-T114Q-S126A-D127S-F128S-N242D, A37T-539E-I43V-A47V-T56Y-I80V-N85 S-E87D-T114Q-D127V-F128 S-N242D, A37T-539E-I43V-A47V-T56Y-I80V-N85S-E87D-T114Q-S126M-D127S-F128T-N242D, A37T-539E-I43V-A47V-T56Y-I80V-N85S-E87D-T114Q-D127T-F128T-N242D, A37T-539E-I43V-A47V-T56Y-I80V-N85 S-E87D-T114Q-S126A-D127V-F128T-N242D, A37T-539E-I43V-A47V-T56Y-I80V-N85S-E87D-T114Q-D127V-F128T-N242D, A37T-539E-I43V-A47V-T56Y-I80V-N85S-E87D-T114Q-S126T-D127G-F128V-N242D, A37T-S39E-I43V-A47V-T56Y-I80V-N85S-E87D-T114Q-D127L-F128V-N242D, A37T-S39E-143V-A47V-T56Y-I80V-N85S-E87D-T114Q-S126M-D127A-F128W-N242D, A37T-S39E-143V-A47V-P54T-T56Y-I80V-N85S-E87D-S99E-T114Q-S126T-F128A-N242D, and A37T-S39E-I43V-A47V-T56Y-I80V-N85S-E87D-S99E-T114Q-D127E-F128G-N242D; (v) A37T-S39E-I43V-A47V-T56Y-I80V-N85S-E87D-T114Q-S126A-D127S-F128A-N242D, A37T-S39E-I43V-A47V-T56Y-I80V-N85S-E87D-S99R-T114Q-D127A-F128C-N242D, A37T-S39E-143V-A47V-T56Y-I80V-N85S-E87D-S99R-T114Q-F128E-N242D, A37T-S39E-I43V-A47V-T56Y-I80V-N85S-E87D-S99R-T114Q-S126T-D127E-F128E-N242D, A37T-S39E-I43V-A47V-T56Y-I80V-N85S-E87D-T114Q-D127P-F128E-N242D, A37T-S39E-I43V-A47V-T56Y-I80V-N85 S-E87D-T114Q-S126G-D127T-F128E-N242D, A37T-S39E-I43V-A47V-T56Y-I80V-N85 S-E87D-S99T-T114Q-S126G-N242D, A37T-S39E-I43V-A47V-T56Y-I80V-N85S-E87D-S99R-T114Q-S126A-D127E-F128G-N242D, A37T-S39E-I43V-A47V-T56Y-I80V-N85S-E87D-S99R-T114Q-D127E-F128G-N242D, A37T-S39E-I43V-A47V-T56Y-I80V-N85S-E87D-S99H-T114Q-D127G-F128G-N242D, A37T-S39E-I43V-A47V-T56Y-I80V-N85S-E87D-T114Q-D127N-F128G-N242D, A37T-S39E-I43V-A47V-T56Y-I80V-N85S-E87D-T114Q-S126G-D127V-F128G-N242D, A37T-S39E-I43V-A47V-T56Y-I80V-N85S-E87D-S99I-T114Q-S126T-D127E-F1281-N242D, A37T-539E-I43V-A47V-T56Y-I80V-N85S-E87D-T114Q-S126A-D127G-F128N-N242D, A37T-539E-I43V-A47V-T56Y-I80V-N85S-E87D-T114Q-S126A-D127L-F128N-N242D, A37T-539E-I43V-A47V-T56Y-I80V-N85S-E87D-T114Q-D127G-F128Q-N242D, A37T-539E-I43V-A47V-T56Y-I80V-N85S-E87D-599H-T114Q-D127S-F128Q-N242D, A37T-539E-I43V-A47V-T56Y-I80V-N85 S-E87D-599M-T114Q-D127G-F128 S-N242D, A37T-539E-I43V-A47V-T56Y-I80V-N85S-E87D-T114Q-S126A-D127V-F128T-N242D, A37T-539E-I43V-A47V-T56Y-I80V-N85S-E87D-T114Q-S126M-D127A-F128W-N242D, and A37T-539E-I43V-A47V-T56Y-I80V-N85S-E87D-599E-T114Q-D127E-F128G-N242D; (vi) A37T-539E-I43V-A47V-T56Y-I80V-N85S-E87D-599H-T114Q-D127S-F128Q-N242D, A37T-539E-I43V-A47V-T56Y-I80V-N85S-E87D-T114Q-D127P-F128E-N242D, A37T-539E-I43V-A47V-T56Y-I80V-N85S-E87D-T114Q-S126G-D127T-F128E-N242D, A37T-539E-I43V-A47V-T56Y-I80V-N85 S-E87D-599R-T114Q-F128E-N242D, A37T-539E-I43V-A47V-T56Y-I80V-N85S-E87D-599R-T114Q-D127E-F128G-N242D, A37T-539E-I43V-A47V-T56Y-I80V-N85 S-E87D-599R-T114Q-S126T-D127E-F128E-N242D, A37T-539E-I43V-A47V-T56Y-I80V-N85S-E87D-599R-T114Q-S126A-D127E-F128G-N242D, A37T-539E-I43V-A47V-P54T-T56Y-I80V-N85S-E87D-599R-T114Q-S126A-F128G-N242D, A37T-S39E-I43V-A47V-P54T-T56Y-I80V-N85 S-E87D-S99R-T114Q-F128E-N242D, and A37T-S39E-I43V-A47V-P54T-T56Y-I80V-N85S-E87D-S99R-T114Q-S126A-D127E-F128G-N242D; or (vii) combinations of (i)-(vi).

Another embodiment is directed to one or more subtilisin variant comprising an amino acid sequence comprising two, three, or four or more substitutions at positions corresponding to SEQ ID NO:1 positions selected from: A037C-S039E-I043V-A047V-P054T-T056Y-I080V-N085 S-E087D-S099R-T114Q-S126A-D127E-F128G-N242D, A037D-S039E-I043V-A047V-P054T-T056Y-I080V-N085S-E087D-S099R-T114Q-S126A-D127E-F128G-N242D, A037G-S039E-I043V-A047V-P054T-T056Y-I080V-N085S-E087D-S099R-T114Q-S126A-D127E-F128G-N242D, A037H-S039E-I043V-A047V-P054T-T056Y-I080V-N085S-E087D-S099R-T114Q-S126A-D127E-F128G-N242D, A037N-S039E-I043V-A047V-P054T-T056Y-I080V-N085 S-E087D-S099R-T114Q-S126A-D127E-F128G-N242D, A037P-S039E-I043V-A047V-P054T-T056Y-I080V-N085S-E087D-S099R-T114Q-S126A-D127E-F128G-N242D, A037Q-S039E-I043V-A047V-P054T-T056Y-I080V-N085S-E087D-S099R-T114Q-S126A-D127E-F128G-N242D, A037T-S039D-I043V-A047V-P054T-T056Y-I080V-N085S-E087D-S099R-T114Q-S126A-D127E-F128G-N242D, A037T-S039E-A047V-I080V-N085S-S099R-N242D, A037T-S039E-A047V-P054T-T056Y-I080V-N085 S-E087D-S099R-S126A-D127E-F128G-N242D, A037T-S039E-A047V-P054T-T056Y-I080V-N085S-E087D-S099R-T114Q-S126A-D127E-F128G-N242D, A037T-S039E-A047V-T056Y-E087D-S099R-T114A-F128A-N242D, A037T-S039E-A047V-T056Y-I080V-N085S-E087D-S099R-S126A-D127E-F128G-N242D, A037T-S039E-A047V-T056Y-I080V-N085 S-E087D-S099R-T114Q-S126A-D127E-F128G-N242D, A037T-S039E-I043V-A047D-P054T-T056Y-I080V-N085S-E087D-S099R-T114Q-S126A-D127E-F128G-N242D, A037T-S039E-I043V-A047E-P054T-T056Y-I080V-N085S-E087D-S099R-T114Q-S126A-D127E-F128G-N242D, A037T-S039E-I043V-A047F-P054T-T056Y-I080V-N085S-E087D-S099R-T114Q-S126A-D127E-F128G-N242D, A037T-S039E-I043V-A047H-P054T-T056Y-I080V-N085 S-E087D-S099R-T114Q-S126A-D127E-F128G-N242D, A037T-S039E-I043V-A0471-P054T-T056Y-I080V-N085S-E087D-S099R-T114Q-S126A-D127E-F128G-N242D, A037T-S039E-I043V-A047M-P054T-T056Y-I080V-N085S-E087D-S099R-T114Q-S126A-D127E-F128G-N242D, A037T-S039E-I043V-A047N-P054T-T056Y-I080V-N085S-E087D-S099R-T114Q-S126A-D127E-F128G-N242D, A037T-S039E-I043V-A047Q-P054T-T056Y-I080V-N085 S-E087D-S099R-T114Q-S126A-

D127E-F128G-N242D, A037T-S039E-I043V-A0475-P054T-T056Y-I080V-N085S-E087D-S099R-T114Q-S126A-D127E-F128G-N242D, A037T-S039E-I043V-A047V, A037T-S039E-I043V-A047V-I080V-N085S-E087D-S099R-S126A-D127E-F128G-N242D, A037T-S039E-I043V-A047V-I080V-N085S-E087D-S099R-T114Q-S126A-D127E-F128G-N242D, A037T-S039E-I043V-A047V-N085S-E087D-S099R-T114Q-N242D, A037T-S039E-I043V-A047V-N242D, A037T-S039E-I043V-A047V-P054E-T056Y-I080V-N085S-E087D-S099R-T114Q-S126A-D127E-F128G-N242D, A037T-S039E-I043V-A047V-P054G-T056Y-I080V-N085S-E087D-S099R-T114Q-S126A-D127E-F128G-N242D, A037T-S039E-I043V-A047V-P0541-T056Y-I080V-N085 S-E087D-S099R-T114Q-S126A-D127E-F128G-N242D, A037T-S039E-I043V-A047V-P054L-T056Y-I080V-N085S-E087D-S099R-T114Q-S126A-D127E-F128G-N242D, A037T-S039E-I043V-A047V-P054Q-T056Y-I080V-N085S-E087D-S099R-T114Q-S126A-D127E-F128G-N242D, A037T-S039E-I043V-A047V-P0545-T056Y-I080V-N085S-E087D-S099R-T114Q-S126A-D127E-F128G-N242D, A037T-S039E-I043V-A047V-P054T-I080V-N085S-E087D-S099R-S126A-D127E-F128G-N242D, A037T-S039E-I043V-A047V-P054T-I080V-N085 S-E087D-S099R-T114Q-S126A-D127E-F128G-N242D, A037T-S039E-I043V-A047V-P054T-T056A-I080V-N085S-E087D-S099R-T114Q-S126A-D127E-F128G-N242D, A037T-S039E-I043V-A047V-P054T-T056C-I080V-N085S-E087D-S099R-T114Q-S126A-D127E-F128G-N242D, A037T-S039E-I043V-A047V-P054T-T056D-I080V-N085S-E087D-S099R-T114Q-S126A-D127E-F128G-N242D, A037T-S039E-I043V-A047V-P054T-T056E-I080V-N085 S-E087D-S099R-T114Q-S126A-D127E-F128G-N242D, A037T-S039E-I043V-A047V-P054T-T056F-I080V-N085S-E087D-S099R-T114Q-S126A-D127E-F128G-N242D, A037T-S039E-I043V-A047V-P054T-T056H-I080V-N085S-E087D-S099R-T114Q-S126A-D127E-F128G-N242D, A037T-S039E-I043V-A047V-P054T-T0561-I080V-N085S-E087D-S099R-T114Q-S126A-D127E-F128G-N242D, A037T-S039E-I043V-A047V-P054T-T056K-I080V-N085 S-E087D-S099R-T114Q-S126A-D127E-F128G-N242D, A037T-S039E-I043V-A047V-P054T-T056L-I080V-N085S-E087D-S099R-T114Q-S126A-D127E-F128G-N242D, A037T-S039E-I043V-A047V-P054T-T056M-I080V-N085S-E087D-S099R-T114Q-S126A-D127E-F128G-N242D, A037T-S039E-I043V-A047V-P054T-T056N-I080V-N085S-E087D-S099R-T114Q-S126A-D127E-F128G-N242D, A037T-S039E-I043V-A047V-P054T-T056P-I080V-N085 S-E087D-S099R-T114Q-S126A-D127E-F128G-N242D, A037T-S039E-I043V-A047V-P054T-T056Q-I080V-N085S-E087D-S099R-T114Q-S126A-D127E-F128G-N242D, A037T-S039E-I043V-A047V-P054T-T0565-I080V-N085S-E087D-S099R-T114Q-S126A-D127E-F128G-N242D, A037T-S039E-I043V-A047V-P054T-T056V-I080V-N085S-E087D-S099R-T114Q-S126A-D127E-F128G-N242D, A037T-S039E-I043V-A047V-P054T-T056W-I080V-N085 S-E087D-S099R-T114Q-S126A-D127E-F128G-N242D, A037T-S039E-I043V-A047V-P054T-T056Y-I080C-N085S-E087D-S099R-T114Q-S126A-D127E-F128G-N242D, A037T-S039E-I043V-A047V-P054T-T056Y-1080L-N085S-E087D-S099R-T114Q-S126A-D127E-F128G-N242D, A037T-S039E-I043V-A047V-P054T-T056Y-I080V-E087D-S099R-S126A-D127E-F128G-N242D, A037T-S039E-I043V-A047V-P054T-T056Y-I080V-E087D-S099R-T114Q-S126A-D127E-F128G-N242D, A037T-S039E-I043V-A047V-P054T-T056Y-I080V-N085A-E087D-S099R-T114Q-S126A-D127E-F128G-N242D, A037T-S039E-I043V-A047V-P054T-T056Y-I080V-N085D-E087D-S099R-T114Q-S126A-D127E-F128G-N242D, A037T-S039E-I043V-A047V-P054T-T056Y-I080V-N085E-E087D-S099R-T114Q-S126A-D127E-F128G-N242D, A037T-S039E-I043V-A047V-P054T-T056Y-I080V-N085H-E087D-S099R-T114Q-S126A-D127E-F128G-N242D, A037T-S039E-I043V-A047V-P054T-T056Y-I080V-N085L-E087D-S099R-T114Q-S126A-D127E-F128G-N242D, A037T-S039E-I043V-A047V-P054T-T056Y-I080V-N085P-E087D-S099R-T114Q-S126A-D127E-F128G-N242D, A037T-S039E-I043V-A047V-P054T-T056Y-I080V-N085Q-E087D-S099R-T114Q-S126A-D127E-F128G-N242D, A037T-S039E-I043V-A047V-P054T-T056Y-I080V-N085S-E087D-N097A-S099R-T114Q-S126A-D127E-F128G-N242D, A037T-S039E-I043V-A047V-P054T-T056Y-I080V-N085S-E087D-N097G-S099R-T114Q-S126A-D127E-F128G-N242D, A037T-S039E-I043V-A047V-P054T-T056Y-I080V-N085S-E087D-N097S-S099R-T114Q-S126A-D127E-F128G-N242D, A037T-S039E-I043V-A047V-P054T-T056Y-I080V-N085S-E087D-S099E-T114Q-S126A-D127E-F128G-N242D, A037T-S039E-I043V-A047V-P054T-T056Y-I080V-N085 S-E087D-S099E-T114Q-S126T-F128A-N242D, A037T-S039E-I043V-A047V-P054T-T056Y-I080V-N085S-E087D-S099M-T114Q-S126A-D127E-F128G-N242D, A037T-S039E-I043V-A047V-P054T-T056Y-I080V-N085S-E087D-S099R-D127E-F128G-N242D, A037T-S039E-I043V-A047V-P054T-T056Y-I080V-N085S-E087D-S099R-S101A-T114Q-S126A-D127E-F128G-N242D, A037T-S039E-I043V-A047V-P054T-T056Y-I080V-N085S-E087D-S099R-S126A-D127E-F128G, A037T-S039E-I043V-A047V-P054T-T056Y-I080V-N085S-E087D-S099R-S126A-D127E-F128G-N242D, A037T-S039E-I043V-A047V-P054T-T056Y-I080V-N085S-E087D-S099R-S126A-D127E-N242D, A037T-S039E-I043V-A047V-P054T-T056Y-I080V-N085S-E087D-S099R-S126A-F128G-N242D, A037T-S039E-I043V-A047V-P054T-T056Y-I080V-N085S-E087D-S099R-T114D-S126A-D127E-F128G-N242D, A037T-S039E-I043V-A047V-P054T-T056Y-I080V-N085S-E087D-S099R-T114E-S126A-D127E-F128G-N242D, A037T-S039E-I043V-A047V-P054T-T056Y-I080V-N085S-E087D-S099R-T114F-S126A-D127E-F128G-N242D, A037T-S039E-I043V-A047V-P054T-T056Y-I080V-N085 S-E087D-S099R-T114G-S126A-D127E-F128G-N242D, A037T-S039E-I043V-A047V-P054T-T056Y-I080V-N085S-E087D-S099R-T114H-S126A-D127E-F128G-N242D, A037T-S039E-I043V-A047V-P054T-T056Y-I080V-N085S-E087D-S099R-T1141-S126A-D127E-F128G-N242D, A037T-S039E-I043V-A047V-P054T-T056Y-I080V-N085S-E087D-S099R-T114L-S126A-D127E-F128G-N242D, A037T-S039E-I043V-A047V-P054T-T056Y-I080V-N085 S-E087D-S099R-T114Q-D127E-F128G-N242D, A037T-S039E-I043V-A047V-P054T-T056Y-I080V-N085S-E087D-S099R-T114Q-D127G-F128E-N242D, A037T-S039E-I043V-A047V-P054T-T056Y-I080V-N085S-E087D-S099R-T114Q-D127G-F128P-N242D, A037T-S039E-I043V-A047V-P054T-T056Y-I080V-N085 S-E087D-S099R-T114Q-D1271-F128S-N242D, A037T-S039E-I043V-A047V-P054T-T056Y-I080V-N085S-E087D-S099R-T114Q-D1271-F128T-N242D, A037T-S039E-I043V-A047V-P054T-T056Y-I080V-N085S-E087D-S099R-T114Q-D127N-F128D-N242D, A037T-S039E-I043V-A047V-P054T-T056Y-I080V-N085

S-E087D-S099R-T114Q-D127S-F128 S-N242D, A037T-S039E-I043V-A047V-P054T-T056Y-I080V-N085S-E087D-S099R-T114Q-D127T-F128A-N242D, A037T-S039E-I043V-A047V-P054T-T056Y-I080V-N085S-E087D-S099R-T114Q-F128E-N242D, A037T-S039E-I043V-A047V-P054T-T056Y-I080V-N085S-E087D-S099R-T114Q-M117I-M122L-S126A-D127E-F128G-M211L-N242D, A037T-S039E-I043V-A047V-P054T-T056Y-I080V-N085S-E087D-S099R-T114Q-M117I-M122L-S126A-D127E-F128G-N242D, A037T-S039E-I043V-A047V-P054T-T056Y-I080V-N085 S-E087D-S099R-T114Q-M122L-S126A-D127E-F128G-M211L-N242D, A037T-S039E-I043V-A047V-P054T-T056Y-I080V-N085S-E087D-S099R-T114Q-M122L-S126A-D127E-F128G-N242D, A037T-S039E-I043V-A047V-P054T-T056Y-I080V-N085S-E087D-S099R-T114Q-N116R-S126A-D127E-F128G-N242D, A037T-S039E-I043V-A047V-P054T-T056Y-I080V-N085 S-E087D-S099R-T114Q-S126A-D127E-F128A-N242D, A037T-S039E-I043V-A047V-P054T-T056Y-I080V-N085S-E087D-S099R-T114Q-S126A-D127E-F128D-N242D, A037T-S039E-I043V-A047V-P054T-T056Y-I080V-N085S-E087D-S099R-T114Q-S126A-D127E-F128E-N242D, A037T-S039E-I043V-A047V-P054T-T056Y-I080V-N085 S-E087D-S099R-T114Q-S126A-D127E-F128G, A037T-S039E-I043V-A047V-P054T-T056Y-I080V-N085S-E087D-S099R-T114Q-S126A-D127E-F128G-G157S-N242D, A037T-S039E-I043V-A047V-P054T-T056Y-I080V-N085S-E087D-S099R-T114Q-S126A-D127E-F128G-M211L-N242D, A037T-S039E-I043V-A047V-P054T-T056Y-I080V-N085 S-E087D-S099R-T114Q-S126A-D127E-F128G-N242D, A037T-S039E-I043V-A047V-P054T-T056Y-I080V-N085S-E087D-S099R-T114Q-S126A-D127E-N242D, A037T-S039E-I043V-A047V-P054T-T056Y-I080V-N085 S-E087D-S099R-T114Q-S126A-D127N-F128C-N242D, A037T-S039E-I043V-A047V-P054T-T056Y-I080V-N085 S-E087D-S099R-T114Q-S126A-D127S-F128 S-N242D, A037T-S039E-I043V-A047V-P054T-T056Y-I080V-N085S-E087D-S099R-T114Q-S126A-D127W-F128E-N242D, A037T-S039E-I043V-A047V-P054T-T056Y-I080V-N085S-E087D-S099R-T114Q-S126A-F128G-N242D, A037T-S039E-I043V-A047V-P054T-T056Y-I080V-N085S-E087D-S099R-T114Q-S126A-F128Q-N242D, A037T-S039E-I043V-A047V-P054T-T056Y-I080V-N085S-E087D-S099R-T114Q-S126D-D127G-F128A-N242D, A037T-S039E-I043V-A047V-P054T-T056Y-I080V-N085S-E087D-S099R-T114Q-S126F-D127E-F128G-N242D, A037T-S039E-I043V-A047V-P054T-T056Y-I080V-N085 S-E087D-S099R-T114Q-S126G-D127E-F128D-N242D, A037T-S039E-I043V-A047V-P054T-T056Y-I080V-N085S-E087D-S099R-T114Q-S126G-D127P-F128C-N242D, A037T-S039E-I043V-A047V-P054T-T056Y-I080V-N085S-E087D-S099R-T114Q-S126H-D127E-F128G-N242D, A037T-S039E-I043V-A047V-P054T-T056Y-I080V-N085S-E087D-S099R-T114Q-S1261-D127E-F128T-N242D, A037T-S039E-I043V-A047V-P054T-T056Y-I080V-N085 S-E087D-S099R-T114Q-S126L-D127G-F128E-N242D, A037T-S039E-I043V-A047V-P054T-T056Y-I080V-N085S-E087D-S099R-T114Q-S126L-D127P-F128G-N242D, A037T-S039E-I043V-A047V-P054T-T056Y-I080V-N085S-E087D-S099R-T114Q-S126L-D127T-F128Q-N242D, A037T-S039E-I043V-A047V-P054T-T056Y-I080V-N085S-E087D-S099R-T114Q-S126L-F128A-N242D, A037T-S039E-I043V-A047V-P054T-T056Y-I080V-N085S-E087D-S099R-T114Q-S126L-F128H-N242D, A037T-S039E-I043V-A047V-P054T-T056Y-I080V-N085S-E087D-S099R-T114Q-S126M-D127A-F128D-N242D, A037T-S039E-I043V-A047V-P054T-T056Y-I080V-N085S-E087D-S099R-T114Q-S126N-D127E-F128G-N242D, A037T-S039E-I043V-A047V-P054T-T056Y-I080V-N085S-E087D-S099R-T114Q-S126N-D127G-F128L-N242D, A037T-S039E-I043V-A047V-P054T-T056Y-I080V-N085S-E087D-S099R-T114Q-S126Q-D127A-F128D-N242D, A037T-S039E-I043V-A047V-P054T-T056Y-I080V-N085S-E087D-S099R-T114Q-S126T-D127E-F128A-N242D, A037T-S039E-I043V-A047V-P054T-T056Y-I080V-N085S-E087D-S099R-T114Q-S126T-D127E-F128L-N242D, A037T-S039E-I043V-A047V-P054T-T056Y-I080V-N085S-E087D-S099R-T114Q-S126T-D127G-F128G-N242D, A037T-S039E-I043V-A047V-P054T-T056Y-I080V-N085S-E087D-S099R-T114Q-S126T-D127Y-F128D-N242D, A037T-S039E-I043V-A047V-P054T-T056Y-I080V-N085S-E087D-S099R-T114Q-S126T-F128A-N242D, A037T-S039E-I043V-A047V-P054T-T056Y-I080V-N085S-E087D-S099R-T114Q-S126T-F128E-N242D, A037T-S039E-I043V-A047V-P054T-T056Y-I080V-N085S-E087D-S099R-T114Q-S126V-D127A-F128T-N242D, A037T-S039E-I043V-A047V-P054T-T056Y-I080V-N085S-E087D-S099R-T114Q-S126V-D127E-F128V-N242D, A037T-S039E-I043V-A047V-P054T-T056Y-I080V-N085S-E087D-S099R-T114Q-S126Y-D127E-F128G-N242D, A037T-S039E-I043V-A047V-P054T-T056Y-I080V-N085S-E087D-S099R-T114Q-S126Y-F128L-N242D, A037T-S039E-I043V-A047V-P054T-T056Y-I080V-N085S-E087D-S099R-T114V-S126A-D127E-F128G-N242D, A037T-S039E-I043V-A047V-P054T-T056Y-I080V-N085S-E087D-S099R-V102E-T114Q-S126A-D127E-F128G-N242D, A037T-S039E-I043V-A047V-P054T-T056Y-I080V-N085S-E087D-S099R-V102I-T114Q-S126A-D127E-F128G-N242D, A037T-S039E-I043V-A047V-P054T-T056Y-I080V-N085S-E087D-S099V-T114Q-S126A-D127E-F128G-N242D, A037T-S039E-I043V-A047V-P054T-T056Y-I080V-N085S-E087D-S126A-D127E-F128G-N242D, A037T-S039E-I043V-A047V-P054T-T056Y-I080V-N085S-E087D-T114Q-S126A-D127E-F128G-N242D, A037T-S039E-I043V-A047V-P054T-T056Y-I080V-N085S-S099R-S126A-D127E-F128G-N242D, A037T-S039E-I043V-A047V-P054T-T056Y-I080V-N085S-S099R-T114Q-S126A-D127E-F128G-N242D, A037T-S039E-I043V-A047V-P054T-T056Y-I080V-N085T-E087D-S099R-T114Q-S126A-D127E-F128G-N242D, A037T-S039E-I043V-A047V-P054T-T056Y-I080V-N085V-E087D-S099R-T114Q-S126A-D127E-F128G-N242D, A037T-S039E-I043V-A047V-P054T-T056Y-I080V-N085W-E087D-S099R-T114Q-S126A-D127E-F128G-N242D, A037T-S039E-I043V-A047V-P054T-T056Y-N074C-I080V-N085S-E087D-S099R-T114Q-S126A-D127E-F128G-N242D, A037T-S039E-I043V-A047V-P054T-T056Y-N074D-I080V-N085S-E087D-S099R-T114Q-S126A-D127E-F128G-N242D, A037T-S039E-I043V-A047V-P054T-T056Y-N074E-I080V-N085S-E087D-S099R-T114Q-S126A-D127E-F128G-N242D, A037T-S039E-I043V-A047V-P054T-T056Y-N074H-I080V-N085S-E087D-S099R-T114Q-S126A-D127E-F128G-N242D, A037T-S039E-I043V-A047V-P054T-T056Y-N0745-I080V-N085S-E087D-S099R-T114Q-S126A-D127E-F128G-N242D, A037T-S039E-I043V-A047V-P054T-T056Y-N074T-I080V-N085S-E087D-S099R-T114Q-S126A-D127E-F128G-N242D, A037T-S039E-I043V-A047V-P054T-T056Y-N085S-E087D-S099R-S126A-D127E-F128G-N242D, A037T-S039E-I043V-A047V-P054T-T056Y-N085S-E087D-S099R-T114Q-S126A-D127E-F128G-N242D,

A037T-S039E-I043V-A047V-P054T-T056Y-S099R-S126A-D127E-F128G-N242D, A037T-S039E-I043V-A047V-P054T-T056Y-S099R-T114Q-S126A-D127E-F128G, A037T-S039E-I043V-A047V-P054T-T056Y-S099R-T114Q-S126A-D127E-F128G-N242D, A037T-S039E-I043V-A047V-P054V-T056Y-I080V-N085S-E087D-S099R-T114Q-S126A-D127E-F128G-N242D, A037T-S039E-I043V-A047V-T056Y-I080V-E087D-S099R-S126A-D127E-F128G-N242D, A037T-S039E-I043V-A047V-T056Y-I080V-E087D-S099R-T114Q-S126A-D127E-F128G-N242D, A037T-S039E-I043V-A047V-T056Y-I080V-N085S-E087D-S099A-T114Q-S126M-D127S-F128A-N242D, A037T-S039E-I043V-A047V-T056Y-I080V-N085S-E087D-S099E-T114Q-D127E-F128G-N242D, A037T-S039E-I043V-A047V-T056Y-I080V-N085S-E087D-S099H-T114Q-D127G-F128G-N242D, A037T-S039E-I043V-A047V-T056Y-I080V-N085S-E087D-S099H-T114Q-D127Q-F128N-N242D, A037T-S039E-I043V-A047V-T056Y-I080V-N085 S-E087D-S099H-T114Q-D127S-F128Q-N242D, A037T-S039E-I043V-A047V-T056Y-I080V-N085S-E087D-S0991-T114Q-S126T-D127E-F1281-N242D, A037T-S039E-I043V-A047V-T056Y-I080V-N085S-E087D-S099K-T114Q-D127L-F128C-N242D, A037T-S039E-I043V-A047V-T056Y-I080V-N085S-E087D-S099K-T114Q-S126G-D127G-F128G-N242D, A037T-S039E-I043V-A047V-T056Y-I080V-N085 S-E087D-S099M-T114Q-D127G-F128 S-N242D, A037T-S039E-I043V-A047V-T056Y-I080V-N085S-E087D-S099M-T114Q-S126E-D127A-F1285-N242D, A037T-S039E-I043V-A047V-T056Y-I080V-N085S-E087D-S099N-T114Q-S126T-D127Q-N242D, A037T-S039E-I043V-A047V-T056Y-I080V-N085S-E087D-S099Q-T114Q-S126T-D127V-F128D-N242D, A037T-S039E-I043V-A047V-T056Y-I080V-N085S-E087D-S099R-D127E-F128G-N242D, A037T-S039E-I043V-A047V-T056Y-I080V-N085 S-E087D-S099R-S126A-D127E-F128G, A037T-S039E-I043V-A047V-T056Y-I080V-N085 S-E087D-S099R-S126A-D127E-F128G-N242D, A037T-S039E-I043V-A047V-T056Y-I080V-N085S-E087D-S099R-S126A-D127E-N242D, A037T-S039E-I043V-A047V-T056Y-I080V-N085 S-E087D-S099R-S126A-F128G-N242D, A037T-S039E-I043V-A047V-T056Y-I080V-N085S-E087D-S099R-T114Q-D127A-F128C-N242D, A037T-S039E-I043V-A047V-T056Y-I080V-N085S-E087D-S099R-T114Q-D127E-F128G-N242D, A037T-S039E-I043V-A047V-T056Y-I080V-N085S-E087D-S099R-T114Q-F128E-N242D, A037T-S039E-I043V-A047V-T056Y-I080V-N085S-E087D-S099R-T114Q-M117I-S126A-D127E-F128G-M211L-M122L-N242D, A037T-S039E-I043V-A047V-T056Y-I080V-N085S-E087D-S099R-T114Q-M117I-S126A-D127E-F128G-M211L-N242D, A037T-S039E-I043V-A047V-T056Y-I080V-N085S-E087D-S099R-T114Q-M122L-S126A-D127E-F128G-N242D, A037T-S039E-I043V-A047V-T056Y-I080V-N085 S-E087D-S099R-T114Q-S126A-D127E-F128G, A037T-S039E-I043V-A047V-T056Y-I080V-N085S-E087D-S099R-T114Q-S126A-D127E-F128G-M211L-M122L-N242D, A037T-S039E-I043V-A047V-T056Y-I080V-N085S-E087D-S099R-T114Q-S126A-D127E-F128G-M211L-N242D, A037T-S039E-I043V-A047V-T056Y-I080V-N085S-E087D-S099R-T114Q-S126A-D127E-F128G-N242D, A037T-S039E-I043V-A047V-T056Y-I080V-N085S-E087D-S099R-T114Q-S126A-D127E-N242D, A037T-S039E-I043V-A047V-T056Y-I080V-N085S-E087D-S099R-T114Q-S126A-F128G-N242D, A037T-S039E-I043V-A047V-T056Y-I080V-N085S-E087D-S099R-T114Q-S126D-D127S-F128A-N242D, A037T-S039E-I043V-A047V-T056Y-I080V-N085S-E087D-S099R-T114Q-S126E-D127A-F128 S-N242D, A037T-S039E-I043V-A047V-T056Y-I080V-N085S-E087D-S099R-T114Q-S126L-D127H-F128E-N242D, A037T-S039E-I043V-A047V-T056Y-I080V-N085S-E087D-S099R-T114Q-S126M-D127L-F128E-N242D, A037T-S039E-I043V-A047V-T056Y-I080V-N085 S-E087D-S099R-T114Q-S126M-D127P-F128E-N242D, A037T-S039E-I043V-A047V-T056Y-I080V-N085S-E087D-S099R-T114Q-S126N-D127G-F128G-N242D, A037T-S039E-I043V-A047V-T056Y-I080V-N085S-E087D-S099R-T114Q-S126Q-D127V-F128C-N242D, A037T-S039E-I043V-A047V-T056Y-I080V-N085S-E087D-S099R-T114Q-S126T-D127E-F128E-N242D, A037T-S039E-I043V-A047V-T056Y-I080V-N085S-E087D-S099R-T114Q-S126T-F128A-N242D, A037T-S039E-I043V-A047V-T056Y-I080V-N085 S-E087D-S099R-T114Q-S126V-D127G-A128E-F128A-N242D, A037T-S039E-I043V-A047V-T056Y-I080V-N085 S-E087D-S099R-T114Q-S126W-D127N-F128D-N242D, A037T-S039E-I043V-A047V-T056Y-I080V-N085S-E087D-S099T-T114Q-S126G-D127G-F128T-N242D, A037T-S039E-I043V-A047V-T056Y-I080V-N085S-E087D-S099T-T114Q-S126G-D127G-F128V-N242D, A037T-S039E-I043V-A047V-T056Y-I080V-N085S-E087D-S099T-T114Q-S126G-N242D, A037T-S039E-I043V-A047V-T056Y-I080V-N085S-E087D-S099T-T114Q-S126V-D127E-F128K-N242D, A037T-S039E-I043V-A047V-T056Y-I080V-N085S-E087D-S126A-D127E-F128G-N242D, A037T-S039E-I043V-A047V-T056Y-I080V-N085S-E087D-T114Q-D127A-F128V-N242D, A037T-S039E-I043V-A047V-T056Y-I080V-N085S-E087D-T114Q-D127G-F128L-N242D, A037T-S039E-I043V-A047V-T056Y-I080V-N085S-E087D-T114Q-D127G-F128Q-N242D, A037T-S039E-I043V-A047V-T056Y-I080V-N085S-E087D-T114Q-D127L-F128N-N242D, A037T-S039E-I043V-A047V-T056Y-I080V-N085S-E087D-T114Q-D127L-F128V-N242D, A037T-S039E-I043V-A047V-T056Y-I080V-N085S-E087D-T114Q-D127N-F128G-N242D, A037T-S039E-I043V-A047V-T056Y-I080V-N085S-E087D-T114Q-D127P-F128E-N242D, A037T-S039E-I043V-A047V-T056Y-I080V-N085S-E087D-T114Q-D127Q-F128M-N242D, A037T-S039E-I043V-A047V-T056Y-I080V-N085S-E087D-T114Q-D127Q-F128S-N242D, A037T-S039E-I043V-A047V-T056Y-I080V-N085S-E087D-T114Q-D127T-F128T-N242D, A037T-S039E-I043V-A047V-T056Y-I080V-N085S-E087D-T114Q-D127V-F128S-N242D, A037T-S039E-I043V-A047V-T056Y-I080V-N085S-E087D-T114Q-D127V-F128T-N242D, A037T-S039E-I043V-A047V-T056Y-I080V-N085S-E087D-T114Q-S126A-D127E-F128G-N242D, A037T-S039E-I043V-A047V-T056Y-I080V-N085S-E087D-T114Q-S126A-D127G-F128N-N242D, A037T-S039E-I043V-A047V-T056Y-I080V-N085S-E087D-T114Q-S126A-D127H-F128V-N242D, A037T-S039E-I043V-A047V-T056Y-I080V-N085S-E087D-T114Q-S126A-D127L-F128N-N242D, A037T-S039E-I043V-A047V-T056Y-I080V-N085S-E087D-T114Q-S126A-D127S-F128A-N242D, A037T-S039E-I043V-A047V-T056Y-I080V-N085S-E087D-T114Q-S126A-D127S-F128S-N242D, A037T-S039E-I043V-A047V-T056Y-I080V-N085S-E087D-T114Q-S126A-D127V-F128T-N242D, A037T-S039E-I043V-A047V-T056Y-I080V-N085S-E087D-T114Q-S126A-D127W-F128G-N242D, A037T-S039E-I043V-A047V-T056Y-I080V-N085S-E087D-

T114Q-S126G-D127A-F128G-N242D, A037T-S039E-I043V-A047V-T056Y-I080V-N085S-E087D-T114Q-S126G-D127T-F128E-N242D, A037T-S039E-I043V-A047V-T056Y-I080V-N085S-E087D-T114Q-S126G-D127V-F128G-N242D, A037T-S039E-I043V-A047V-T056Y-I080V-N085 S-E087D-T114Q-S126L-D127F-F128R-N242D, A037T-S039E-I043V-A047V-T056Y-I080V-N085S-E087D-T114Q-S126M-D127A-F128W-N242D, A037T-S039E-I043V-A047V-T056Y-I080V-N085S-E087D-T114Q-S126M-D127S-F128A-N242D, A037T-S039E-I043V-A047V-T056Y-I080V-N085S-E087D-T114Q-S126M-D127S-F128T-N242D, A037T-S039E-I043V-A047V-T056Y-I080V-N085S-E087D-T114Q-S126M-D127V-F128G-N242D, A037T-S039E-I043V-A047V-T056Y-I080V-N085S-E087D-T114Q-S126Q-D127L-F128H-N242D, A037T-S039E-I043V-A047V-T056Y-I080V-N085S-E087D-T114Q-S126R-F128A-N242D, A037T-S039E-I043V-A047V-T056Y-I080V-N085S-E087D-T114Q-S126T-D127G-F128V-N242D, A037T-S039E-I043V-A047V-T056Y-I080V-N085S-E087D-T114Q-S126T-D127L-F128 S-N242D, A037T-S039E-I043V-A047V-T056Y-I080V-N085S-E087D-T114Q-S126V-D127M-F128S-N242D, A037T-S039E-I043V-A047V-T056Y-I080V-N085S-S099R-S126A-D127E-F128G-N242D, A037T-S039E-I043V-A047V-T056Y-I080V-N085S-S099R-T114Q-S126A-D127E-F128G-N242D, A037T-S039E-I043V-A047V-T056Y-N085S-E087D-S099R-S126A-D127E-F128G-N242D, A037T-S039E-I043V-A047V-T056Y-N085S-E087D-S099R-T114Q-S126A-D127E-F128G-N242D, A037T-S039E-I043V-A047V-T056Y-S099R-S126A-D127E-F128G, A037T-S039E-I043V-A047V-T056Y-S099R-T114Q-S126A-D127E-F128G, A037T-S039E-I043V-A047W-P054T-T056Y-I080V-N085S-E087D-S099R-T114Q-S126A-D127E-F128G-N242D, A037T-S039E-I043V-A047Y-P054T-T056Y-I080V-N085S-E087D-S099R-T114Q-S126A-D127E-F128G-N242D, A037T-S039E-I043V-I080V-N085S-E087D-S099R-T114Q, A037T-S039E-I043V-I080V-N085S-E087D-S099R-T114Q-N242D, A037T-S039E-I043V-N085S-E087D-S099R-T114Q, A037T-S039E-I043V-N085S-E087D-S099R-T114Q-N242D, A037T-S039E-I043V-P054T-T056Y-I080V-N085S-E087D-S099R-S126A-D127E-F128G-N242D, A037T-S039E-I043V-P054T-T056Y-I080V-N085S-E087D-S099R-T114Q-S126A-D127E-F128G-N242D, A037T-S039E-I043V-S099R-T114Q-N242D, A037T-S039E-I043V-T056Y-I080V-N085S-E087D-S099R-S126A-D127E-F128G-N242D, A037T-S039E-I043V-T056Y-I080V-N085S-E087D-S099R-T114Q-S126A-D127E-F128G-N242D, A037T-S039E-S099R-S126A-D127E-F128G, A037T-S039E-S099R-S126A-D127E-F128G-M211L, A037V-S039E-I043V-A047V-P054T-T056Y-I080V-N085S-E087D-S099R-T114Q-S126A-D127E-F128G-N242D, A037W-S039E-I043V-A047V-P054T-T056Y-I080V-N085S-E087D-S099R-T114Q-S126A-D127E-F128G-N242D, A037Y-S039E-I043V-A047V-P054T-T056Y-I080V-N085S-E087D-S099R-T114Q-S126A-D127E-F128G-N242D, I021V-A037T-S039E-I043V-A047V-P054T-T056Y-I080V-N085S-E087D-S099R-T114Q-S126A-D127E-F128G-N242D, I043V-A047V-N242D, I043V-A047V-S099R-F128A-N242D, I043V-A047V-S099R-S126T-N242D, I043V-A047V-T056Y-T114Q, I043V-A047V-T056Y-T114Q-N242D, N242D, S039E-A047V-N074D-S099R-S126A-D127E-F128G, S039E-A047V-N085 S-S099R-T114Q-N242D, S039E-A047V-S099R-S126A-D127E-F128G, S039E-A047V-S099R-S126A-D127E-F128G-M211L, S039E-A047V-T056Y-I080V-N085S-S099R-T114Q, S039E-A047V-T056Y-N085S-E087D-S099R-T114Q, S039E-A047V-T056Y-N085S-S099R-T114Q-F128A-N242D, S039E-E087D-N242D, S039E-E087D-S099R-F128A-N242D, S039E-E087D-S099R-S126A-D127E-F128G, S039E-E087D-S099R-S126T-N242D, S039E-I043V-A047V-E087D-N242D, S039E-I043V-A047V-E087D-S099R, S039E-I043V-A047V-P054T-T056Y-I080V-N085 S-E087D-S099R-S126A-D127E-F128G-N242D, S039E-I043V-A047V-S099R-T114Q-N242D, S039E-I043V-A047V-T056Y-I080V-E087D-S099R-T114Q-S126T-N242D, S039E-I043V-A047V-T056Y-I080V-N085 S-E087D-S099R-S126A-D127E-F128G-N242D, S039E-I043V-A047V-T056Y-I080V-N085 S-E087D-S099R-T114Q-S126A-D127E-F128G-N242D, S039E-I043V-E087D-S099R-T114Q, S039E-I043V-N074D-S099R-S126A-D127E-F128G, S039E-I043V-N085S-E087D-S099R-T114Q-N242D, S039E-I043V-S099R-S126A-D127E-F128G, S039E-I043V-S099R-S126A-D127E-F128G-M211L, S039E-I043V-T056Y-E087D-S099R-N242D, S039E-I043V-T056Y-E087D-S099R-T114Q, S039E-I043V-T056Y-I080V-N085S-S099R-T114Q-N242D, S039E-I043V-T056Y-S099R-T114Q-F128A-N242D, S039E-I080V-S099R-S126A-D127E-F128G, S039E-I080V-S099R-S126A-D127E-F128G-M211L, S039E-I080V-S099R-T114Q-N242D, S039E-N042R-S099R-S126A-D127E-F128G, S039E-N074D-E087D-S099R-S126A-D127E-F128G, S039E-N074D-I080V-S099R-S126A-D127E-F128G, S039E-N074D-N085S-S099R-S126A-D127E-F128G, S039E-N074D-S099R-S126A-D127E-F128G-N242D, S039E-N074D-S099R-T114Q-S126A-D127E-F128G, S039E-N085S-S099R-S126A-D127E-F128G, S039E-N085S-S099R-S126A-D127E-F128G-M211L, S039E-P054T-N074D-S099R-S126A-D127E-F128G, S039E-P054T-S099R-S126A-D127E-F128G, S039E-P054T-S099R-S126A-D127E-F128G-M211L, S039E-S099R-S126A-D127E-F128G, S039E-S099R-S126A-D127E-F128G-M211L, S039E-S099R-S126A-D127E-F128G-N242D, S039E-S099R-S126A-D127E-F128G-N253D, S039E-S099R-S126A-D127E-F128G-Q200L, S039E-S099R-S126A-D127E-F128G-Q256E, S039E-S099R-S126A-D127E-F128G-S255W, S039E-S099R-S126A-D127E-F128G-V199I, S039E-S099R-S126A-D127E-F128G-Y203W, S039E-S099R-T114Q-S126A-D127E-F128G, S039E-T056Y-E087D-T114Q-N242D, S039E-T056Y-N074D-S099R-S126A-D127E-F128G, S039E-T056Y-S099R-S126A-D127E-F128G, S039E-T056Y-S099R-S126A-D127E-F128G-M211L, S099R-F128A-N242D, S099R-S126T-N242D, T009E-S039E-S099R-S126A-D127E-F128G, T056Y-S099R-S126A-D127E-F128G, T056Y-S099R-T114Q-F128A-N242D, T056Y-S099R-T114Q-S126T-N242D, and T056Y-T114Q-N242D.

In another embodiment, variants provided herein comprise one or more variants having amino acids substitutions selected from the group consisting of those listed in Tables 6, 7, 8, 9, 10, 11, 12, and 13 having a PI≥1.1 in one or more of the cleaning assays or stability assay, including laundry, BMI, egg, crème brûlée assays or EDTA stability assay, or having greater than 40% residual activity in EDTA stability assay.

In another embodiment, the one or more subtilisin variant provided herein comprises one or more additional substitutions, deletions, or insertions, or combinations thereof. In one example, the variant having one or more additional substitutions, is a variant having at least 90% identity with the amino acid sequence of SEQ ID NO:1 and the variant comprising at least one additional substitution (using the SEQ ID NO:1 numbering) selected from the group consisting of T3V, T9R, A15T, V66A, N74D, N97A/D/G/S, S99G/M, S101A, V102E/I, N116V/R, S126F, D127Q, F128A, G157S, Y161A, R164S, T188P, V199I, Q200C/E/I/K/T/V/W/L, Y203W, M211C, N212D, M216S/F, Q239R and T249R. In yet another example, the variant having one or more additional substitutions, is a variant having at least 90% identity with the amino acid sequence of SEQ ID NO:13 and the variant comprising at least one additional substitution (using the SEQ ID NO:13 numbering) selected from the group consisting of S3V, 59R, A15T, V66A, N74D, S97A/D/E/G, S99G/M, S101A, V102E/I, G116V/R, S126F, P127Q, S128A, G157S, Y161A, R164S, A188P, V199I, Q200C/E/I/K/T/V/W/L, Y203W, L211C/M, N212D, M216S/F, Q239R and T249R.

Yet still another embodiment is directed to one or more subtilisin variant described herein with the proviso that said two, three, or four or more substitutions is non-naturally occurring. Yet an even still further embodiment is directed to one or more subtilisin variant described herein wherein said variant (i) is a member of the *B. gibsonii*-clade; (ii) is isolated; (iii) has proteolytic activity; or (iv) comprises a combination of (i) to (iii). Still yet another embodiment is directed to one or more subtilisin variant described herein, wherein said variant is derived from a parent or reference polypeptide with (i) 70%, 75%, 80%, 85%, 86%, 87%, 88%, 89%, 90%, 91%, 92%, 93%, 94%, 95%, 96%, 97%, 98%, 99%, or 100% amino acid sequence identity to the amino acid sequence of SEQ ID NO:1; or (ii) 100% amino acid sequence identity to the amino acid sequence of SEQ ID NO:1. An even further embodiment is directed to one or more subtilisin variant described herein, wherein said variant comprises an amino acid sequence with (i) 70%, 75%, 80%, 85%, 86%, 87%, 88%, 89%, 90%, 91%, 92%, 93%, 94%, 95%, 96%, 97%, 98%, 99% or less than 100% amino acid sequence identity to the amino acid sequence of SEQ ID NO:1; (ii) 85%, 86%, 87%, 88%, 89%, 90%, 91%, 92%, 93%, 94%, 95%, 96%, 97%, 98%, 99% or less than 100% amino acid sequence identity to the amino acid sequence of SEQ ID NO:1; or (iii) 94%, 95%, 96%, 97%, 98%, 99%, or less than 100% amino acid sequence identity to the amino acid sequence of SEQ ID NO:1.

Some embodiments are directed to a method of cleaning, comprising contacting a surface or an item in need of cleaning with an effective amount of one or more subtilisin variant described herein or one or more composition described herein. In further embodiments, the method of cleaning described herein is directed to a method of cleaning a crème brûlée stain. In still other embodiments, the method of cleaning provided herein is directed to a method of cleaning an egg stain.

In still another embodiment, one or more subtilisin variant described herein has enzymatic activity (e.g., protease activity) and thus is useful in cleaning applications, including but not limited to, methods for cleaning dishware items, tableware items, fabrics, and items having hard surfaces (e.g., the hard surface of a table, table top, wall, furniture item, floor, ceiling, etc.). Some embodiments are directed to one or more cleaning composition comprising one or more subtilisin variant described herein. The enzymatic activity (e.g., protease enzyme activity) of one or more subtilisin variant described herein can be readily determined through procedures well known to those of ordinary skill in the art. The Examples presented infra describe methods for evaluating cleaning performance. In some embodiments, one or more subtilisin variant described herein has protease activity in the presence of a surfactant. In other embodiments, the surfactant is selected from the group consisting of a non-ionic surfactant, an anionic surfactant, a cationic surfactant, a zwitterionic surfactant, an ampholytic surfactant, a semi-polar non-ionic surfactant, and a combination thereof. In some embodiments, the protease activity comprises casein hydrolysis activity. In some embodiments, the protease activity comprises dimethylcasein hydrolysis activity.

In some embodiments, one or more subtilisin variant described herein demonstrates at least one improved property compared to a reference subtilisin. In some such embodiments, the one or more subtilisin variant demonstrates improved cleaning performance, improved stability, or both improved cleaning performance and improved stability compared to a reference subtilisin.

The term "enhanced stability" or "improved stability" in the context of an oxidation, chelator, denaturant, surfactant, thermal and/or pH stable protease refers to a higher retained proteolytic activity over time as compared to a reference protease, for example, a wild-type protease or parent protease. Autolysis has been identified as one mode of subtilisin activity loss in liquid detergents. (Stoner et al., 2004 Protease autolysis in heavy-duty liquid detergent formulations: effects of thermodynamic stabilizers and protease inhibitors, Enzyme and Microbial Technology 34:114-125).

The terms "thermally stable" and "thermostable" and "thermostability" with regard to a protease variant refers to a protease that retains a specified amount of enzymatic activity after exposure to identified temperatures over a given period of time under conditions (or "stress conditions") prevailing during proteolytic, hydrolysing, cleaning or other process, while being exposed to altered temperatures. "Altered temperatures" encompass increased or decreased temperatures.

In some embodiments, the variant proteases provided herein retain at least about 40%, about 50%, about 60%, about 70%, about 80%, about 85%, about 90%, about 92%, about 95%, about 96%, about 97%, about 98%, or about 99% proteolytic activity after exposure to temperatures of 50° C., 51° C., 52° C., 53° C., 54° C., 55° C., 56° C., 57° C., 58° C., 58° C., 59° C., or 60° C. over a given time period, for example, at least about 20 minutes, at least about 60 minutes, about 90 minutes, about 120 minutes, about 180 minutes, about 240 minutes, about 300 minutes, about 360 minutes, about 420 minutes, about 480 minutes, about 540 minutes, about 600 minutes, about 660 minutes, about 720 minutes, about 780 minutes, about 840 minutes, about 900 minutes, about 960 minutes, about 1020 minutes, about 1080 minutes, about 1140 minutes, or about 1200 minutes.

In some embodiments, the one or more variants having improved stability are selected from the group of variants listed in Tables 8, 10, and 11.

A still further embodiment is directed to one or more subtilisin variant described herein, in which the variant has a crème brûlée stain cleaning PI>1 when compared to the crème brûlée stain cleaning performance of a protease with an amino acid sequence of SEQ ID NO:1. Another embodiment is directed to one or more subtilisin variant described herein, in which the variant has a crème brûlée stain cleaning PI>1 when compared to the crème brûlée stain cleaning performance of a protease with an amino acid sequence of SEQ ID NO:1, in which the crème brûlée stain cleaning performance of the variant and protease with the amino acid sequence of SEQ ID NO:1 is measured in accordance with the crème brûlée assay described in Example 2. In some such embodiments, the one or more subtilisin variant having a crème brûlée stain cleaning PI>1 when compared to the crème brûlée stain cleaning performance of a protease with an amino acid sequence of SEQ ID NO:1 is selected from the variants provided in Tables 7 and 9.

A still further embodiment is directed to one or more subtilisin variant described herein, in which the variant has an egg yolk stain cleaning PI>1 when compared to the egg yolk stain cleaning performance of a protease with an amino acid sequence of SEQ ID NO:1. Another embodiment is directed to one or more subtilisin variant described herein, in which the variant has an egg yolk stain cleaning PI>1 when compared to the egg yolk stain cleaning performance of a protease with an amino acid sequence of SEQ ID NO:1, in which the egg yolk stain cleaning performance of the variant and protease with the amino acid sequence of SEQ ID NO:1 is measured in accordance with the egg yolk stain assay described in Example 2. In some such embodiments, the one or more subtilisin variant having an egg stain cleaning PI>1 when compared to the egg stain cleaning performance of a protease with an amino acid sequence of SEQ ID NO:1 is selected from the variants provided in Tables 8, 10, and 11.

In some embodiments, one or more subtilisin variant described herein demonstrates cleaning performance in a cleaning composition. Cleaning compositions often include ingredients harmful to the stability and performance of enzymes, making cleaning compositions a harsh environment for enzymes, e.g. serine proteases, to retain function. Thus, it is not trivial for an enzyme to be put in a cleaning composition and expect enzymatic function (e.g. serine protease activity, such as demonstrated by cleaning performance). In some embodiments, one or more subtilisin variant described herein demonstrates cleaning performance in automatic dishwashing (ADW) detergent compositions. In some such embodiments, the one or more variants is selected from the group of variants listed in Tables 7, 8, 9, 10, and 11. In some embodiments, the cleaning performance in automatic dishwashing (ADW) detergent compositions includes cleaning of egg yolk stains. In some embodiments, one or more subtilisin variant described herein demonstrates cleaning performance in laundry detergent compositions. In some embodiments, the cleaning performance in laundry detergent compositions includes cleaning of blood/milk/ink stains. In one or more cleaning composition described herein, one or more subtilisin variant described herein demonstrates cleaning performance with or without a bleach component.

In an even still further embodiment, one or more subtilisin variant described herein has one or more improved property when compared to a reference subtilisin; where the improved property is selected from improved cleaning performance in detergent, improved stability; and combinations thereof. In another embodiment, reference subtilisin comprises an amino acid sequence of SEQ ID NO:1. In yet another embodiment, the improved property is (i) improved cleaning performance in detergent, where the variant has a BMI, crème brûlée and/or egg stain cleaning PI>1; and/or (ii) improved stability, where the variant has a residual activity greater than the reference subtilisin. In still yet another embodiment, the cleaning performance in detergent is measured in accordance with the cleaning performance in laundry (HDL) and ADW detergents assay of Example 2; and/or the stability is measured in accordance with the stability assay of Example 2. In some such embodiments, the one or more variants is selected from the group of variants listed in Tables 7, 8, 9, 10, 11, 12, and 13.

One or more subtilisin variant described herein can be subject to various changes, such as one or more amino acid insertion, deletion, and/or substitution, either conservative or non-conservative, including where such changes do not substantially alter the enzymatic activity of the polypeptide. Similarly, one or more nucleic acid described herein can also be subject to various changes, such as one or more substitutions of one or more nucleotides in one or more codons such that a particular codon encodes the same or a different amino acid, resulting in either a silent variation (e.g., when the encoded amino acid is not altered by the nucleotide mutation) or non-silent variation, one or more deletions of one or more nucleic acids (or codons) in the sequence, one or more additions or insertions of one or more nucleic acids (or codons) in the sequence, and/or cleavage of or one or more truncations of one or more nucleic acids (or codons) in the sequence. Many such changes in the nucleic acid sequence may not substantially alter the enzymatic activity of the resulting encoded polypeptide enzyme compared to the polypeptide enzyme encoded by the original nucleic acid sequence. One or more nucleic acid sequence described herein can also be modified to include one or more codons that provide for optimum expression in an expression system (e.g., bacterial expression system), while, if desired, said one or more codons still encode the same amino acid(s).

Some embodiments are directed to one or more polypeptide having the desired enzymatic activity (e.g., protease enzyme activity or cleaning performance activity) which comprise sequences having the amino acid substitutions and/or variations described herein and also which comprise one or more additional amino acid substitution or variation, such as conservative and non-conservative substitutions or variations, wherein the polypeptide exhibits, maintains, or approximately maintains the desired enzymatic activity (e.g., proteolytic activity). In some embodiments, the proteolytic activity is reflected in the cleaning activity or performance of one or more subtilisin variant described herein. For example, an amino acid substitution may include, but is not limited to, one or more non-conservative substitution, and/or one or more conservative amino acid substitution. A conservative amino acid residue substitution typically involves exchanging a member within one functional class of amino acid residues for a residue that belongs to the same functional class (conservative amino acid residues are considered functionally homologous or conserved in calculating percent functional homology). For example, alanine, glycine, serine, and threonine are functionally similar and thus may serve as conservative amino acid substitutions for one another. Aspartic acid and glutamic acid may serve as conservative substitutions for one another. Asparagine and glutamine may serve as conservative substitutions for one another. Arginine, lysine, and histidine may serve as conservative substitutions for one another. Isoleucine, leucine, methionine, and valine may serve as conservative substitutions for one another. Phenylalanine, tyrosine, and tryptophan may serve as conservative substitutions for one another.

Other conservative amino acid substitution groups can be envisioned. For example, amino acids can be grouped by similar function or chemical structure or composition (e.g., acidic, basic, aliphatic, aromatic, sulfur-containing). For instance, an aliphatic grouping may comprise: Glycine (G), Alanine (A), Valine (V), Leucine (L), Isoleucine (I). Other groups containing amino acids that are considered conservative substitutions for one another include: aromatic: Phenylalanine (F), Tyrosine (Y), Tryptophan (W); sulfur-containing: Methionine (M), Cysteine (C); Basic: Arginine (R), Lysine (K), Histidine (H); Acidic: Aspartic acid (D), Glutamic acid (E); non-polar uncharged residues, Cysteine (C), Methionine (M), and Proline (P); hydrophilic uncharged residues: Serine (S), Threonine (T), Asparagine (N), and Glutamine (Q). Additional groupings of amino acids are well-known to those of skill in the art and described in various standard textbooks. Listing of a polypeptide sequence herein, in conjunction with the above substitution groups, provides an express listing of all conservatively substituted polypeptide sequences.

More conservative substitutions exist within the amino acid residue classes described above, which also or alternatively can be suitable. Conservation groups for substitutions that are more conservative include: valine-leucine-isoleucine, phenylalanine-tyrosine, lysine-arginine, alanine-valine, and asparagine-glutamine.

Conservative substitutions or variations of one or more subtilisin variant described herein includes substitutions or variations of a small percentage, sometimes less than 5%, 4%, 3%, 2%, or 1%, or less than 10, 9, 8, 7, 6, 5, 4, 3, 2, or 1 amino acid with a conservatively selected amino acid of the same conservative substitution group.

Some embodiments are directed to one or more polynucleotide comprising a nucleic acid sequence that encodes one or more subtilisin variant described herein. In even further embodiments, one or more polynucleotide or nucleic acid described herein is an isolated, recombinant, substantially pure, and/or non-naturally occurring polynucleotide or nucleic acid.

Some embodiments are directed to a synthetically derived nucleic acid comprising a nucleotide sequence encoding one or more subtilisin variant described herein. In some embodiments, one or more subtilisin variant described herein is expressed recombinantly with a homologous pro-peptide sequence (e.g., Bgi02446 pro-peptide).

Nucleic acids of the invention can be generated by using any suitable synthesis, manipulation, and/or isolation techniques, or combinations thereof. For example, a polynucleotide of the invention may be produced using standard nucleic acid synthesis techniques, such as solid-phase synthesis techniques that are well-known to those skilled in the art. In such techniques, fragments of up to 50 or more nucleotide bases are typically synthesized, then joined (e.g., by enzymatic or chemical ligation methods) to form essentially any desired continuous nucleic acid sequence. The synthesis of the nucleic acids of the invention can be also facilitated by any suitable method known in the art, including but not limited to chemical synthesis using the classical phosphoramidite method (See e.g., Beaucage et al. Tetrahedron Letters 22:1859-69 [1981]); or the method described by Matthes et al. (See, Matthes et al., EMBO J. 3:801-805 [1984]), as is typically practiced in automated synthetic methods. Nucleic acids of the invention also can be produced by using an automatic DNA synthesizer. Customized nucleic acids can be ordered from a variety of commercial sources (e.g., The Midland Certified Reagent Company, the Great American Gene Company, Operon Technologies Inc., and DNA2.0). Other techniques for synthesizing nucleic acids and related principles are known in the art (See e.g., Itakura et al., Ann. Rev. Biochem. 53:323 [1984]; and Itakura et al., Science 198:1056 [1984]).

In another embodiment, one or more polynucleotide described herein encodes a subtilisin variant comprises an aspartic acid (D) amino acid substitution at a position corresponding to position N242 of SEQ ID NO:1, wherein the amino acid positions of the variant are numbered by correspondence with the amino acid sequence of SEQ ID NO:1. In still another embodiment, one or more polynucleotide described herein encodes a subtilisin variant comprising a 242D substitution, wherein said subtilisin variant comprises a productivity performance index (PI) greater than 1.0, which productivity PI is relative to a subtilisin variant polypeptide that does not comprise an aspartic acid (D) amino acid substitution at a position corresponding to position N242 of SEQ ID NO:1, wherein the amino acid positions of the variant are numbered by correspondence with the amino acid sequence of SEQ ID NO:1. In yet still another embodiment, one or more polynucleotide described herein is an expression construct comprising in the 5' to 3' direction: a promoter sequence which is upstream (5') and operably linked to a signal peptide sequence, a pro-peptide sequence which is downstream (3') and operably linked to the 5' signal peptide sequence, a nucleic acid sequence encoding the variant that comprises the aspartic acid (D) amino acid substitution at the position that corresponds to the N242 position of SEQ ID NO:1 which nucleic acid sequence is downstream (3') and operably linked to the 5' pro-peptide sequence and an optional terminator sequence which is downstream (3') and operably linked to the nucleic acid sequence encoding the variant that comprises the aspartic acid (D) amino acid substitution at the position that corresponds to the N242 position of SEQ ID NO:1, wherein the amino acid positions of the variant are numbered by correspondence with the amino acid sequence of SEQ ID NO:1. In even yet still another embodiment, one or more polynucleotide described herein is an expression construct comprising in the 5' to 3' direction: a promoter sequence which is upstream (5') and operably linked to a signal peptide sequence, a pro-peptide sequence which is downstream (3') and operably linked to the 5' signal peptide sequence, a nucleic acid sequence encoding the variant that comprises the aspartic acid (D) amino acid substitution at the position that corresponds to the N242 position of SEQ ID NO:1 which nucleic acid sequence is downstream (3') and operably linked to the 5' pro-peptide sequence and an optional terminator sequence which is downstream (3') and operably linked to the nucleic acid sequence encoding the variant that comprises the aspartic acid (D) amino acid substitution at the position that corresponds to the N242 position of SEQ ID NO:1, wherein (i) the promoter sequence comprises a *Bacillus* spp. ribosomal RNA promoter, wherein *Bacillus* spp. ribosomal RNA promoter is a *Bacillus subtilis* rrnI promoter; (ii) the signal peptide sequence comprises SEQ ID NO:3; (iii) the pro-peptide sequence comprises SEQ ID NO:4; (iv) the nucleic acid sequence that encodes said variant encodes a polypeptide comprising an amino acid sequence selected from a subtilisin variant provided herein having an aspartic acid (D) amino acid substitution at a position that corresponds to 242 of SEQ ID NO:1; and/or (v) the optional terminator sequence comprises SEQ ID NO:6, wherein the amino acid positions of the variant are numbered by correspondence with the amino acid sequence of SEQ ID NO:1.

As indicated above, recombinant DNA techniques useful in modification of nucleic acids are well known in the art. For example, techniques such as restriction endonuclease digestion, ligation, reverse transcription and cDNA production, and polymerase chain reaction (e.g., PCR) are known and readily employed by those of skill in the art. One or more nucleotide described herein may also be obtained by screening cDNA libraries using one or more oligonucleotide probes that can hybridize to or PCR-amplify polynucleotides which encode one or more subtilisin variant described herein. Procedures for screening and isolating cDNA clones and PCR amplification procedures are well known to those of skill in the art and described in standard references known to those skilled in the art. Some nucleic acids described herein can be obtained by altering a naturally occurring polynucleotide backbone (e.g., that encodes an enzyme or parent protease) by, for example, a known mutagenesis procedure (e.g., site-directed mutagenesis, site saturation mutagenesis, and in vitro recombination). A variety of methods are known in the art that are suitable for generating modified polynucleotides that can encode one or more subtilisin variant described herein, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches.

Some embodiments provide one or more vector comprising one or more polynucleotide described herein; one or more expression vector or expression cassette comprising one or more nucleic acid or polynucleotide described herein; one or more isolated, substantially pure, or recombinant DNA construct comprising one or more nucleic acid or polynucleotide described herein; one or more isolated or recombinant cell comprising one or more polynucleotide described herein; and one or more composition comprising one or more such vector, nucleic acid, expression vector, expression cassette, DNA construct, cell, cell culture, or any combination or mixture thereof.

Some embodiments provide one or more recombinant cell comprising one or more vector (e.g., expression vector or DNA construct) described herein which comprise one or more nucleic acid or polynucleotide described herein. Some such recombinant cells are transformed or transfected with such one or more vector, although other methods are available and known in the art. Such cells are typically referred to as host cells. Some such cells comprise bacterial cells, including, but are not limited to *Bacillus* sp. cells, such as *B. subtilis* cells. The invention also provides recombinant cells (e.g., recombinant host cells) comprising one or more subtilisin variant described herein.

Other embodiments provide one or more vector comprising one or more nucleic acid or polynucleotide described herein. In some embodiments, the vector is an expression vector or expression cassette in which one or more polynucleotide sequence described herein is operably linked to one or more additional nucleic acid segment required for efficient gene expression (e.g., a promoter operably linked to a polynucleotide described herein). A vector may include a transcription terminator and/or a selection gene, such as an antibiotic resistance gene, that enables continuous cultural maintenance of plasmid-infected host cells by growth in antimicrobial-containing media.

Another embodiment is directed to a method for increasing the production of a subtilisin variant in a Gram positive bacterial host cell, the method comprising: (a) introducing into a host cell a polynucleotide construct encoding a subtilisin variant comprising one or more substitutions at one or more positions corresponding to SEQ ID NO:1, wherein the position corresponding to N242 of SEQ ID NO:1 is substituted with an aspartic acid (D) (N242D), and (b) growing the host cell under conditions suitable for the production of the encoded subtilisin variant, wherein the host cell produces an increased amount of the subtilisin variant of (a) relative to a Gram positive host cell of the same genus, species and genetic background comprising an introduced polynucleotide construct encoding a subtilisin variant that does not comprise a substitution at the position corresponding to N242 of SEQ ID NO:1; and wherein the amino acid positions of the variant are numbered by correspondence with the amino acid sequence of SEQ ID NO:1. In still another embodiment, the method for increasing the production of a subtilisin variant in a Gram positive bacterial host cell described hereinabove increases the yield of the subtilisin variant of (a) by at least 2.5%. In still another embodiment, the subtilisin variant of (a) in the method for increasing the production of a subtilisin variant in a Gram positive bacterial host cell described hereinabove has a productivity performance index (PI)>1.0 relative to the subtilisin variant that does not have an aspartic acid (D) substitution at the position corresponding to N242 of SEQ ID NO:1. In still another embodiment, the polynucleotide construct of the method for increasing the production of a subtilisin variant in a Gram positive bacterial host cell described hereinabove is an expression construct comprising in the 5' to 3' direction: a promoter sequence which is upstream (5') and operably linked to a signal peptide sequence, a pro-peptide sequence which is downstream (3') and operably linked to the 5' signal peptide sequence, a nucleic acid sequence encoding the variant that comprises the aspartic acid (D) amino acid substitution at the position that corresponds to the N242 position of SEQ ID NO:1 which nucleic acid sequence is downstream (3') and operably linked to the 5' pro-peptide sequence, and an optional terminator sequence which is downstream (3') and operably linked to the nucleic acid sequence encoding the variant that comprises the aspartic acid (D) amino acid substitution at the position that corresponds to the N242 position of SEQ ID NO:1, wherein the amino acid positions of the variant are numbered by correspondence with the amino acid sequence of SEQ ID NO:1. In an even still further embodiment, the polynucleotide construct of the method for increasing the production of a subtilisin variant in a Gram positive bacterial host cell described hereinabove is an expression construct comprising in the 5' to 3' direction: a promoter sequence which is upstream (5') and operably linked to a signal peptide sequence, a pro-peptide sequence which is downstream (3') and operably linked to the 5' signal peptide sequence, a nucleic acid sequence encoding the variant that comprises the aspartic acid (D) amino acid substitution at the position that corresponds to the N242 position of SEQ ID NO:1 which nucleic acid sequence is downstream (3') and operably linked to the 5' pro-peptide sequence, and an optional terminator sequence which is downstream (3') and operably linked to the nucleic acid sequence encoding the variant that comprises the aspartic acid (D) amino acid substitution at the position that corresponds to the N242 position of SEQ ID NO:1, wherein (i) the promoter sequence comprises a *Bacillus* spp. ribosomal RNA promoter, wherein *Bacillus* spp. ribosomal RNA promoter is a *Bacillus subtilis* rrnI promoter; (ii) the signal peptide sequence comprises SEQ ID NO:3; (iii) the pro-peptide sequence comprises SEQ ID NO:4; (iv) the nucleic acid sequence that encodes said variant encodes a polypeptide comprising an amino acid sequence selected from a subtilisin variant provided herein having an aspartic acid (D) amino acid substitution at a position that corresponds to 242 of SEQ ID NO:1; and/or (v) the optional terminator sequence comprises SEQ ID NO:6, wherein the amino acid positions of the variant are numbered by correspondence with the amino acid sequence of SEQ ID NO:1.

In yet another embodiment, the subtilisin variant of (a) in the method for increasing the production of a subtilisin variant in a Gram positive bacterial host cell described hereinabove further comprises one or more substitutions at one or more positions corresponding to SEQ ID NO:1 positions selected from 9, 37, 39, 42, 43, 47, 54, 56, 74, 80, 85, 87, 99, 114, 126, 127, 128, 199, 200, 203, 211, 253, 255, and 256, wherein the amino acid positions of the variant are numbered by correspondence with the amino acid sequence of SEQ ID NO:1. In still yet a further embodiment, the subtilisin variant of (a) in the method for increasing the production of a subtilisin variant in a Gram positive bacterial host cell described hereinabove further comprises an amino acid sequence comprising one or more substitutions corresponding to SEQ ID NO:1 positions selected from: I043V-A047V-T056Y-T114Q, S039E-I043V-E087D-S099R-T114Q, S039E-I043V-A047V-E087D-S099R, S039E-I043V-T056Y-E087D-S099R-T114Q, S039E-A047V-T056Y-N085S-E087D-S099R-T114Q, S039E-A047V-T056Y-I080V-N085S-S099R-T114Q, A037T-S039E-I043V-N085S-E087D-S099R-T114Q, T056Y-S099R-S126A-D127E-F128G, S039E-I080V-S099R-S126A-D127E-F128G-M211L, S039E-P054T-S099R-S126A-D127E-F128G-M211L, S039E-I043V-S099R-S126A-D127E-F128G-M211L, S039E-N042R-S099R-S126A-D127E-F128G, S039E-I080V-S099R-S126A-D127E-F128G, S039E-S099R-5126A-D127E-F128G-M211L, S039E-N085S-S099R-S126A-D127E-F128G-M211L, S039E-T056Y-S099R-S126A-D127E-F128G-M211L, S039E-A047V-S099R-S126A-D127E-F128G-M211L, S039E-S099R-S126A-D127E-F128G-Y203W, A037T-S039E-S099R-S126A-D127E-F128G-M211L, S039E-S099R-S126A-D127E-F128G-V199I, S039E-I043V-S099R-S126A-D127E-F128G, S039E-S099R-S126A-D127E-F128G-N253D, T009E-S039E-S099R-S126A-D127E-F128G, S039E-S099R-S126A-D127E-F128G-S255W, S039E-T056Y-S099R-S126A-D127E-F128G, S039E-N085S-S099R-S126A-D127E-F128G, S039E-S099R-T114Q-S126A-D127E-F128G, S039E-A047V-S099R-S126A-D127E-F128G, S039E-P054T-S099R-S126A-D127E-F128G, S039E-E087D-S099R-S126A-D127E-F128G, A037T-S039E-S099R-S126A-D127E-F128G, S039E-S099R-S126A-D127E-F128G, S039E-S099R-S126A-D127E-F128G-Q256E, S039E-S099R-S126A-D127E-F128G-Q200L, S039E-N074D-I080V-S099R-S126A-D127E-F128G, A037T-S039E-I043V-A047V, S039E-P054T-N074D-S099R-S126A-D127E-F128G, S039E-A047V-N074D-S099R-S126A-D127E-F128G, S039E-N074D-S099R-T114Q-S126A-D127E-F128G, S039E-N074D-N085S-S099R-S126A-D127E-F128G, S039E-N074D-E087D-S099R-S126A-D127E-F128G, S039E-I043V-N074D-S099R-S126A-D127E-F128G, S039E-T056Y-N074D-S099R-S126A-D127E-F128G, T056Y-S099R-S126A-D127E-F128G, S039E-I080V-S099R-S126A-D127E-F128G-M211L, S039E-P054T-S099R-S126A-D127E-F128G-M211L, S039E-I043V-S099R-S126A-D127E-F128G-M211L, S039E-N042R-S099R-S126A-D127E-F128G, S039E-I080V-S099R-S126A-D127E-F128G, S039E-S099R-S126A-D127E-F128G-M211L, S039E-N085S-S099R-S126A-D127E-F128G-M211L, S039E-T056Y-S099R-S126A-D127E-F128G-M211L, S039E-A047V-S099R-S126A-D127E-F128G-M211L, S039E-S099R-S126A-D127E-F128G-Y203W, A037T-S039E-S099R-S126A-D127E-F128G-M211L, S039E-S099R-S126A-D127E-F128G-V199I, S039E-I043V-S099R-S126A-D127E-F128G, S039E-S099R-S126A-D127E-F128G-N253D, T009E-S039E-S099R-S126A-D127E-F128G, S039E-S099R-S126A-D127E-F128G-S255W, S039E-T056Y-S099R-S126A-D127E-F128G, S039E-N085S-S099R-S126A-D127E-F128G, S039E-S099R-T114Q-S126A-D127E-F128G, S039E-A047V-S099R-S126A-D127E-F128G, S039E-P054T-S099R-S126A-D127E-F128G, S039E-E087D-S099R-S126A-D127E-F128G, A037T-S039E-S099R-S126A-D127E-F128G, S039E-S099R-S126A-D127E-F128G, S039E-S099R-S126A-D127E-F128G-Q256E, S039E-S099R-S126A-D127E-F128G-Q200L, S039E-N074D-I080V-S099R-S126A-D127E-F128G, A037T-S039E-I043V-A047V, S039E-P054T-N074D-S099R-S126A-D127E-F128G, S039E-A047V-N074D-S099R-S126A-D127E-F128G, S039E-N074D-S099R-T114Q-S126A-D127E-F128G, S039E-N074D-N085 S-S099R-S126A-D127E-F128G, S039E-N074D-E087D-S099R-S126A-D127E-F128G, S039E-I043V-N074D-S099R-S126A-D127E-F128G, and S039E-T056Y-N074D-S099R-S126A-D127E-F128G, and combinations thereof; wherein the amino acid positions of the variant are numbered by correspondence with the amino acid sequence of SEQ ID NO:1. In even still yet a further embodiment, the subtilisin variant of (a) in the method for increasing the production of a subtilisin variant in a Gram positive bacterial host cell described hereinabove comprises an amino acid sequence with (i) 70%, 75%, 80%, 85%, 86%, 87%, 88%, 89%, 90%, 91%, 92%, 93%, 94%, 95%, 96%, 97%, 98%, 99% or less than 100% amino acid sequence identity to the amino acid sequence of SEQ ID NO:1; (ii) 85%, 86%, 87%, 88%, 89%, 90%, 91%, 92%, 93%, 94%, 95%, 96%, 97%, 98%, 99% or less than 100% amino acid sequence identity to the amino acid sequence of SEQ ID NO:1; or (iii) 94%, 95%, 96%, 97%, 98%, 99%, or less than 100% amino acid sequence identity to the amino acid sequence of SEQ ID NO:1.

An expression vector may be derived from plasmid or viral DNA, or in alternative embodiments, contains elements of both. Exemplary vectors include, but are not limited to pC194, pJH101, pE194, pHP13 (See, Harwood and Cutting [eds.], Chapter 3, Molecular Biological Methods for *Bacillus*, John Wiley & Sons [1990]; suitable replicating plasmids for *B. subtilis* include those listed on p. 92) See also, Perego, Integrational Vectors for Genetic Manipulations in *B. subtilis*, in Sonenshein et al., [eds.] *B. subtilis* and Other Gram-Positive Bacteria: Biochemistry, Physiology and Molecular Genetics, American Society for Microbiology, Washington, D.C. [1993], pp. 615-624), and p2JM103BBI.

For expression and production of a protein of interest (e.g., serine protease polypeptide) in a cell, at least one expression vector comprising at least one copy of a polynucleotide encoding the serine protease polypeptide, and in some instances comprising multiple copies, is transformed into the cell under conditions suitable for expression of the serine protease. In some embodiments, one or more polynucleotide sequence described herein (as well as other sequences included in the vector) is integrated into the genome of the host cell; while in other embodiments, a plasmid vector comprising one or more polynucleotide sequence described herein remains as autonomous extra-chromosomal element within the cell. The invention provides both extrachromosomal nucleic acid elements as well as incoming nucleotide sequences that are integrated into the host cell genome. One or more vector described herein is useful for producing one or more subtilisin variant described herein. In some embodiments, a polynucleotide construct encoding one or more subtilisin variant described herein is present on an integrating vector that enables the integration and optionally the amplification of the polynucleotide into the host chromosome. Examples of sites for integration are well known to those skilled in the art. In some embodiments, transcription of one or more polynucleotide described herein is effectuated by a promoter that is the wild-type promoter for the selected precursor protease. In other embodiments, the promoter is heterologous to the precursor protease, but is functional in the host cell. Examples of suitable promoters for use in bacterial host cells include, but are not limited to the amyE, amyQ, amyL, pstS, sacB, pSPAC, pAprE, pVeg, pHpaII promoters; the promoter of the *B. stearothermophilus* maltogenic amylase gene; the *B. amyloliquefaciens* (BAN) amylase gene; the *B. subtilis* alkaline protease gene; the *B. clausii* alkaline protease gene the *B. pumilis* xylosidase gene; the *B. thuringiensis* cryIIIA; and the *B. licheniformis* alpha-amylase gene. Additional promoters include, but are not limited to, the A4 promoter, as well as phage Lambda PR or PL promoters, and the *E. coli* lac, trp or tac promoters.

One or more subtilisin variant described herein can be produced in host cells of any suitable microorganism, including bacteria and fungi. In some embodiments, one or more subtilisin variant described herein can be produced in Gram-positive bacteria. In some embodiments, the host cells are *Bacillus* spp., *Streptomyces* spp., *Escherichia* spp., *Aspergillus* spp., *Trichoderma* spp., *Pseudomonas* spp., *Corynebacterium* spp., *Saccharomyces* spp., or *Pichia* spp. In some embodiments, one or more subtilisin variant described herein is produced by *Bacillus* sp. host cells. Examples of *Bacillus* sp. host cells include, but are not limited to *B. licheniformis, B. lentus, B. subtilis, B. amyloliquefaciens, B. lentus, B. brevis, B. stearothermophilus, B. alkalophilus, B. coagulans, B. circulans, B. pumilis, B. thuringiensis, B. clausii, B. megaterium, Myceliopthera* spp, and *Yarrowia* spp, as well as other organisms within the genus *Bacillus*. In some embodiments, *B. subtilis* host cells are used for production of serine protease polypeptides. U.S. Pat. Nos. 5,264,366 and 4,760,025 (RE 34,606) describe various *Bacillus* host strains that can be used for producing one or more subtilisin variant described herein, although other suitable strains can be used.

Several bacterial strains that can be used to produce one or more subtilisin variant described herein include non-recombinant (i.e., wild-type) *Bacillus* sp. strains, as well as variants of naturally-occurring strains and/or recombinant strains. In some embodiments, the host strain is a recombinant strain, wherein a polynucleotide encoding a polypeptide of interest has been introduced into the host. In some embodiments, the host strain is a *B. subtilis* host strain and particularly a recombinant *B. subtilis* host strain. Numerous *B. subtilis* strains are known, including, but not limited to for example, 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211strain (See e.g., Hoch et al., Genetics 73:215-228 [1973]; See also, U.S. Pat. Nos. 4,450,235 and 4,302,544, and EP 0134048). The use of *B. subtilis* as an expression host cell is well known in the art (See e.g., Palva et al., Gene 19:81-87 [1982]; Fahnestock and Fischer, J. Bacteriol., 165:796-804 [1986]; and Wang et al., Gene 69:39-47 [1988]).

In some embodiments, the *Bacillus* host cell is a *Bacillus* sp. that includes a mutation or deletion in at least one of the following genes, degU, degS, degR and degQ. In some embodiments, the mutation is in a degU gene, and in some embodiments the mutation is degU(Hy)32 (See e.g., Msadek et al., J. Bacteriol. 172:824-834 [1990]; and Olmos et al., Mol. Gen. Genet. 253:562-567 [1997]). In some embodiments, the *Bacillus* host comprises a mutation or deletion in scoC4 (See e.g., Caldwell et al., J. Bacteriol. 183:7329-7340 [2001]); spoIIE (See e.g., Arigoni et al., Mol. Microbiol. 31:1407-1415 [1999]); and/or oppA or other genes of the opp operon (See e.g., Perego et al., Mol. Microbiol. 5:173-185 [1991]). Indeed, it is contemplated that any mutation in the opp operon that causes the same phenotype as a mutation in the oppA gene will find use in some embodiments of the altered *Bacillus* strain of the invention. In some embodiments, these mutations occur alone, while in other embodiments, combinations of mutations are present. In some embodiments, an altered *Bacillus* host cell strain that can be used to produce one or more subtilisin variant described herein is a *Bacillus* host strain that already includes a mutation in one or more of the above-mentioned genes. In addition, *Bacillus* sp. host cells that comprise mutation(s) and/or deletions of endogenous protease genes find use. In some embodiments, the *Bacillus* host cell comprises a deletion of the aprE and the nprE genes. In other embodiments, the *Bacillus* sp. host cell comprises a deletion of 5 protease genes, while in other embodiments, the *Bacillus* sp. host cell comprises a deletion of 9 protease genes (See e.g., US2005/0202535).

Host cells are transformed with one or more nucleic acid described herein using any suitable method known in the art. Methods for introducing a nucleic acid (e.g., DNA) into *Bacillus* cells or *E. coli* cells utilizing plasmid DNA constructs or vectors and transforming such plasmid DNA constructs or vectors into such cells are well known. In some embodiments, the plasmids are subsequently isolated from *E. coli* cells and transformed into *Bacillus* cells. However, it is not essential to use intervening microorganisms such as *E. coli*, and in some embodiments, a DNA construct or vector is directly introduced into a *Bacillus* host.

Those of skill in the art are well aware of suitable methods for introducing one or more nucleic acid sequence described herein into *Bacillus* cells (See e.g., Ferrari et al., "Genetics," in Harwood et al. [eds.], *Bacillus*, Plenum Publishing Corp. [1989], pp. 57-72; Saunders et al., J. Bacteriol. 157:718-726 [1984]; Hoch et al., J. Bacteriol. 93:1925-1937 [1967]; Mann et al., Current Microbiol. 13:131-135 [1986]; Holubova, Folia Microbiol. 30:97 [1985]; Chang et al., Mol. Gen. Genet. 168:11-115 [1979]; Vorobjeva et al., FEMS Microbiol. Lett. 7:261-263 [1980]; Smith et al., Appl. Env. Microbiol. 51:634 [1986]; Fisher et al., Arch. Microbiol. 139:213-217 [1981]; and McDonald, J. Gen. Microbiol. 130:203 [1984]). Indeed, such methods as transformation, including protoplast transformation and transfection, transduction, and protoplast fusion are well known and suited for use herein. Methods known in the art to transform *Bacillus* cells include such methods as plasmid marker rescue transformation, which involves the uptake of a donor plasmid by competent cells carrying a partially homologous resident plasmid (See, Contente et al., Plasmid 2:555-571 [1979]; Haima et al., Mol. Gen. Genet. 223:185-191 [1990]; Weinrauch et al., J. Bacteriol. 154:1077-1087 [1983]; and Weinrauch et al., J. Bacteriol. 169:1205-1211 [1987]). In this method, the incoming donor plasmid recombines with the homologous region of the resident "helper" plasmid in a process that mimics chromosomal transformation.

In addition to commonly used methods, in some embodiments, host cells are directly transformed with a DNA construct or vector comprising one or more nucleic acid described herein (i.e., an intermediate cell is not used to amplify, or otherwise process, the DNA construct or vector prior to introduction into the host cell). Introduction of one or more DNA construct or vector described herein into the host cell includes those physical and chemical methods known in the art to introduce a nucleic acid sequence (e.g., DNA sequence) into a host cell without insertion into the host genome. Such methods include, but are not limited to calcium chloride precipitation, electroporation, naked DNA, liposomes and the like. In additional embodiments, DNA constructs or vector are co-transformed with a plasmid, without being inserted into the plasmid. In further embodiments, a selective marker is deleted from the altered *Bacillus* strain by methods known in the art (See, Stahl et al., J. Bacteriol. 158:411-418 [1984]; and Palmeros et al., Gene 247:255-264 [2000]).

In some embodiments, the transformed cells described herein are cultured in conventional nutrient media. The suitable specific culture conditions, such as temperature, pH and the like are known to those skilled in the art and are well described in the scientific literature. In some embodiments, the invention provides a culture (e.g., cell culture) comprising one or more subtilisin variant described herein or one or more nucleic acid described herein.

In some embodiments, host cells transformed with one or more polynucleotide sequence described herein are cultured in a suitable nutrient medium under conditions permitting the expression of one or more subtilisin variant described herein, after which the resulting variant is recovered from the culture. In some embodiments, the variant produced by the cells is recovered from the culture medium by conventional procedures, including, but not limited to for example, separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.).

In some embodiments, a serine protease polypeptide produced by a recombinant host cell is secreted into the culture medium. A nucleic acid sequence that encodes a purification facilitating domain may be used to facilitate purification of proteins. A vector or DNA construct comprising a polynucleotide sequence encoding a serine protease polypeptide may further comprise a nucleic acid sequence encoding a purification facilitating domain to facilitate purification of the serine protease polypeptide (See e.g., Kroll et al., DNA Cell Biol. 12:441-53 [1993]). Such purification facilitating domains include, but are not limited to, for example, metal chelating peptides such as histidine-tryptophan modules that allow purification on immobilized metals (See, Porath, Protein Expr. Purif. 3:263-281 [1992]), protein A domains that allow purification on immobilized immunoglobulin, and the domain utilized in the FLAGS extension/affinity purification system. The inclusion of a cleavable linker sequence such as Factor XA or enterokinase (e.g., sequences available from Invitrogen, San Diego, CA) between the purification domain and the heterologous protein also find use to facilitate purification.

Assays for detecting and measuring the enzymatic activity of an enzyme, such as one or more subtilisin variant described herein, are well known. Various assays for detecting and measuring activity of proteases (e.g., one or more subtilisin variant described herein), are also known to those of ordinary skill in the art. In particular, assays are available for measuring protease activity that are based on the release of acid-soluble peptides from casein or hemoglobin, measured as absorbance at 280 nm or colorimetrically using the Folin method. Other exemplary assays involve the solubilization of chromogenic substrates (See e.g., Ward, "Proteinases," in Fogarty (ed.), Microbial Enzymes and Biotechnology, Applied Science, London, [1983], pp. 251-317). Other exemplary assays include, but are not limited to succinyl-Ala-Ala-Pro-Phe-para nitroanilide assay (suc-AAPF-pNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem. 223:119-129 [1994]; and Hsia et al., Anal Biochem. 242:221-227 [1999]).

A variety of methods can be used to determine the level of production of a mature protease (e.g., one or more mature subtilisin variant described herein) in a host cell. Such methods include, but are not limited to, for example, methods that utilize either polyclonal or monoclonal antibodies specific for the protease. Exemplary methods include, but are not limited to enzyme-linked immunosorbent assays (ELISA), radioimmunoassays (MA), fluorescent immunoassays (FIA), and fluorescent activated cell sorting (FACS). These and other assays are well known in the art (See e.g., Maddox et al., J. Exp. Med. 158:1211 [1983]).

Some other embodiments provide methods for making or producing one or more mature subtilisin variant described herein. A mature serine protease polypeptide does not include a signal peptide or a propeptide sequence. Some methods comprise making or producing one or more subtilisin variant described herein in a recombinant bacterial host cell, such as for example, a *Bacillus* sp. cell (e.g., a *B. subtilis* cell). Some embodiments provide a method of producing one or more subtilisin variant described herein comprising cultivating a recombinant host cell comprising a recombinant expression vector comprising a nucleic acid encoding one or more subtilisin variant described herein under conditions conducive to the production of the variant. Some such methods further comprise recovering the variant from the culture.

Some embodiments provide one or more method of producing one or more subtilisin variant described herein, comprising: (a) introducing a recombinant expression vector comprising a nucleic acid encoding one or more subtilisin variant described herein into a population of cells (e.g., bacterial cells, such as *B. subtilis* cells); and (b) culturing the cells in a culture medium under conditions conducive to produce the variant encoded by the expression vector. Some such methods further comprise: (c) isolating variant from the cells or the culture medium.

Unless otherwise noted, all component or composition levels provided herein are made in reference to the active level of that component or composition, and are exclusive of impurities, for example, residual solvents or by-products, which may be present in commercially available sources. Enzyme component weights are based on total active protein. All percentages and ratios are calculated by weight unless otherwise indicated. All percentages and ratios are calculated based on the total composition unless otherwise indicated. Compositions of the invention include cleaning compositions, such as detergent compositions. In the exemplified detergent compositions, the enzymes levels are expressed by pure enzyme by weight of the total composition and unless otherwise specified, the detergent ingredients are expressed by weight of the total compositions.

While not essential for the purposes of the present invention, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. One embodiment is directed to a composition comprising one or more adjunct material and one or more subtilisin variant described herein. The precise nature of the adjunct materials that re employed in any particular composition, and levels of incorporation thereof, will depend on the physical form of the composition and the nature of the cleaning operation for which it is to be used.

Suitable adjunct materials include, but are not limited to, bleach catalysts, an additional enzyme, enzyme stabilizers (including, for example, an enzyme stabilizing system), chelants, optical brighteners, soil release polymers, dye transfer agents, dispersants, suds suppressors, dyes, perfumes, colorants, filler salts, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. Suitable examples of other adjunct materials and levels of use can be found in U.S. Pat. Nos. 5,576,282; 6,306,812; 6,326,348; 6,610,642; 6,605,458; 5,705,464; 5,710,115; 5,698,504; 5,695,679; 5,686,014; and 5,646,101. In embodiments in which one or more adjunct material is not compatible with one or more subtilisin variant described herein suitable methods of keeping the adjunct material(s) and variant(s) separated (i.e., not in contact with each other) can be employed until combination of the two components is appropriate. Such separation methods include any suitable method known in the art (e.g., gelcaps, encapsulation, tablets, physical separation, etc.). The aforementioned adjunct materials may constitute the balance of the cleaning compositions described herein.

One or more cleaning composition described herein is advantageously employed for example, in laundry applications, hard surface cleaning applications, dishwashing applications, including automatic dishwashing and hand dishwashing, as well as cosmetic applications such as dentures, teeth, hair and skin cleaning and disinfecting applications, such as, for example, but not limited to, disinfecting an automatic dishwashing or laundry machine. The enzymes of the present invention are also suited for use in contact lens cleaning and wound debridement applications. In addition, due to the unique advantages of increased effectiveness in lower temperature solutions, the enzymes of the present invention are ideally suited for laundry applications. Furthermore, the enzymes of the present invention find use in granular and liquid compositions.

Another embodiment is directed to a composition comprising one or more subtilisin variant described herein. In some embodiments, the composition is a cleaning composition. In other embodiments, the composition is a detergent composition. In yet other embodiments, the composition is selected from a laundry detergent composition, an automatic dishwashing (ADW) composition, a hand (manual) dishwashing detergent composition, a hard surface cleaning composition, an eyeglass cleaning composition, a medical instrument cleaning composition, a disinfectant (e.g., malodor or microbial) composition, and a personal care cleaning composition. In still other embodiments, the composition is a laundry detergent composition, an ADW composition, or a hand (manual) dishwashing detergent composition. Even still further embodiments are directed to fabric cleaning compositions, while other embodiments are directed to non-fabric cleaning compositions. In some embodiments, the cleaning composition is boron-free. In other embodiments, the cleaning composition is phosphate-free. In still other embodiments, the composition comprises one or more subtilisin variant described herein and one or more of an excipient, adjunct material, and/or additional enzyme.

In yet still a further embodiment, the composition described herein contains phosphate, is phosphate-free, contains boron, is boron-free, or combinations thereof. In other embodiments, the composition is a boron-free composition. In some embodiments, a boron-free composition is a composition to which a borate stabilizer has not been added. In another embodiment, a boron-free composition is a composition that contains less than 5.5% boron. In a still further embodiment, a boron-free composition is a composition that contains less than 4.5% boron. In yet still another embodiment, a boron-free composition is a composition that contains less than 3.5% boron. In yet still a further embodiment, a boron-free composition is a composition that contains less than 2.5% boron. In even further embodiments, a boron-free composition is a composition that contains less than 1.5% boron. In another embodiment, a boron-free composition is a composition that contains less than 1.0% boron. In still further embodiments, a boron-free composition is a composition that contains less than 0.5% boron. In still further embodiments, a boron-free composition is a composition substantially-free of boron. In other embodiments, the composition is a composition free or substantially-free of enzyme stabilizers or peptide inhibitors.

One or more subtilisin variant described herein also finds use in cleaning additive products. In some embodiments, low temperature solution cleaning applications find use. Some embodiments provide cleaning additive products comprising one or more subtilisin variant described herein, which additive is ideally suited for inclusion in a wash process when additional bleaching effectiveness is desired. Such instances include, but are not limited to low temperature solution cleaning applications. In some embodiments, the additive product is in its simplest form, one or more subtilisin variant described herein. In some embodiments, the additive is packaged in dosage form for addition to a cleaning process. In some embodiments, the additive is packaged in dosage form for addition to a cleaning process where a source of peroxygen is employed and increased bleaching effectiveness is desired.

Exemplary fillers or carriers for granular compositions include, but are not limited to, for example, various salts of sulfate, carbonate and silicate; talc; and clay. Exemplary fillers or carriers for liquid compositions include, but are not limited to, for example, water or low molecular weight primary and secondary alcohols including polyols and diols (e.g., methanol, ethanol, propanol and isopropanol). In some embodiments, the compositions contain from about 5% to about 90% of such filler or carrier. Acidic fillers may be included in such compositions to reduce the pH of the resulting solution in the cleaning method or application.

In another embodiment, one or more composition described herein is in a form selected from gel, tablet, powder, granular, solid, liquid, unit dose, and combinations thereof. In yet another embodiment, one or more composition described herein is in a form selected from a low water compact formula, low water HDL or UD, or high water formula or HDL. In some embodiments, the cleaning composition describe herein is in a unit dose form. In other embodiments, the unit does form is selected from pills, tablets, capsules, gelcaps, sachets, pouches, multi-compartment pouches, and pre-measured powders or liquids. In some embodiments, the unit dose format is designed to provide controlled release of the ingredients within a multi-compartment pouch (or other unit dose format). Suitable unit dose and controlled release formats are described, for example, in EP2100949; WO 02/102955; U.S. Pat. Nos. 4,765,916; 4,972,017; and WO 04/111178. In some embodiments, the unit dose form is a tablet or powder contained in a water-soluble film or pouch.

The present cleaning compositions or cleaning additives comprise an effective amount of one or more subtilisin variant described herein, alone or in combination with one or more additional enzyme. Typically, the present cleaning compositions comprise at least about 0.0001 weight percent, from about 0.0001 to about 10, from about 0.001 to about 1, or from about 0.01 to about 0.1 weight percent of one or more subtilisin variant described herein. In another embodiment, one or more cleaning composition described herein comprises from about 0.01 to about 10 mg, about 0.01 to about 5 mg, about 0.01 to about 2 mg, about 0.01 to about 1 mg, about 0.05 to about 1 mg, about 0.5 to about 10 mg, about 0.5 to about 5 mg, about 0.5 to about 4 mg, about 0.5 to about 4 mg, about 0.5 to about 3 mg, about 0.5 to about 2 mg, about 0.5 to about 1 mg, about 0.1 to about 10 mg, about 0.1 to about 5 mg, about 0.1 to about 4 mg, about 0.1 to about 3 mg, about 0.1 to about 2 mg, about 0.1 to about 2 mg, about 0.1 to about 1 mg, or about 0.1 to about 0.5 mg of one or more subtilisin variant described herein per gram of composition.

In some embodiments, one or more subtilisin variant described herein cleans at low temperatures. In other embodiments, one or more composition described herein cleans at low temperatures. In other embodiments, one or more composition described herein comprises an effective amount of one or more subtilisin variant described herein as useful or effective for cleaning a surface in need of proteinaceous stain removal.

The cleaning compositions herein are typically formulated such that, during use in aqueous cleaning operations, the wash water will have a pH of from about 4.0 to about 11.5, or even from about 5.0 to about 11.5, or even from about 5.0 to about 8.0, or even from about 7.5 to about 10.5. Liquid product formulations are typically formulated to have a pH from about 3.0 to about 9.0 or even from about 3 to about 5. Granular laundry products are typically formulated to have a pH from about 8 to about 11. Some embodiments provide one or more cleaning composition formulated to have an alkaline pH under wash conditions, such as a pH of from about 8.0 to about 12.0, or from about 8.5 to about 11.0, or from about 9.0 to about 11.0. In some embodiments, one or more cleaning composition described herein is formulated to have a neutral pH under wash conditions, such as a pH of from about 5.0 to about 8.0, or from about 5.5 to about 8.0, or from about 6.0 to about 8.0, or from about 6.0 to about 7.5. In some embodiments, the neutral pH conditions can be measured when the cleaning composition is dissolved 1:100 (wt:wt) in de-ionised water at 20° C., measured using a conventional pH meter. Techniques for controlling pH at recommended usage levels include the use of buffers, alkalis, acids, etc., and are well known to those skilled in the art.

In some embodiments, when one or more subtilisin variant described herein is employed in a granular composition or liquid, it is desirable for the variant to be in the form of an encapsulated particle to protect the variant from other components of the granular composition during storage. In addition, encapsulation is also a means of controlling the availability of the variant during the cleaning process. In some embodiments, encapsulation enhances the performance of variant and/or additional enzymes. In this regard, one or more subtilisin variant described herein is encapsulated with any suitable encapsulating material known in the art. In some embodiments, the encapsulating material typically encapsulates at least part of the variant. Typically, the encapsulating material is water-soluble and/or water-dispersible. In some embodiments, the encapsulating material has a glass transition temperature (Tg) of 0° C. or higher. Tg is described in more detail in WO97/11151. The encapsulating material is typically selected from carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See e.g., EP0922499; U.S. Pat. Nos. 4,977,252; 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof; commercially available microspheres that find use include, but are not limited to those supplied by EXPANCEL® (Stockviksverken, Sweden), and PM6545, PM6550, PM7220, PM7228, EXTENDOSPHERES®, LUXSIL®, Q-CEL®, and SPHERICEL® (PQ Corp., Valley Forge, PA).

There are a variety of wash conditions including varying detergent formulations, wash water volumes, wash water temperatures, and lengths of wash time, to which proteases involved in washing are exposed. A low detergent concentration system includes detergents where less than about 800 ppm of the detergent components are present in the wash water. A medium detergent concentration includes detergents where between about 800 ppm and about 2000 ppm of the detergent components are present in the wash water. A high detergent concentration system includes detergents where greater than about 2000 ppm of the detergent components are present in the wash water. In some embodiments, the "cold water washing" of the present invention utilizes "cold water detergent" suitable for washing at temperatures from about 10° C. to about 50° C., or from about 20° C. to about 40° C., or from about 15° C. to about 25° C., as well as all other combinations within the range of about 15° C. to about 35° C., and all ranges within 10° C. to 50° C.

Different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million.

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than about 10.5 (for example about 10.5 to about 20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between about 3 to about 10 grains, about 3 to about 8 grains or about 6 grains. Japanese water hardness is typically lower than North American water hardness, usually less than about 4, for example about 3 grains per gallon mixed $Ca^{2+}/Mg^{2+}$.

Other embodiments are directed to one or more cleaning composition comprising from about 0.00001% to about 10% by weight composition of one or more subtilisin variant described herein and from about 99.999% to about 90.0% by weight composition of one or more adjunct material. In another embodiment, the cleaning composition comprises from about 0.0001% to about 10%, about 0.001% to about 5%, about 0.001% to about 2%, or about 0.005% to about 0.5% by weight composition of one or more subtilisin variant and from about 99.9999% to about 90.0%, about 99.999% to about 98%, about 99.995% to about 99.5% by weight composition of one or more adjunct material.

In other embodiments, the composition described herein comprises one or more subtilisin variant described herein and one or more additional enzyme. The one or more additional enzyme is selected from acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, metalloproteases, nucleases, oxidases, pectate lyases, pectin acetyl esterases, pectinases, pentosanases, peroxidases, phenoloxidases, phosphatases, phospholipases, phytases, polygalacturonases, additional proteases, pullulanases, reductases, rhamnogalacturonases, beta-glucanases, tannases, transglutaminases, xylan acetyl-esterases, xylanases, xyloglucanases, xylosidases, and any combination or mixture thereof. Some embodiments are directed to a combination of enzymes (i.e., a "cocktail") comprising conventional enzymes like amylase, lipase, cutinase, mannanase, and/or cellulase in conjunction with one or more subtilisin variant described herein and/or one or more additional protease.

In another embodiment, one or more composition described herein comprises one or more subtilisin variant described herein and one or more additional protease. In one embodiment, the additional protease is a serine protease. Suitable additional proteases include those of animal, vegetable or microbial origin. In some embodiments, the additional protease is a microbial protease. In other embodiments, the additional protease is a chemically or genetically modified mutant. In another embodiment, the additional protease is a metalloprotease, a fungal subtilisin, an alkaline microbial protease or a trypsin-like protease. Exemplary alkaline proteases include subtilisins derived from, for example, *Bacillus* (e.g., subtilisin, *lentus, amyloliquefaciens*, subtilisin Carlsberg, subtilisin 309, subtilisin 147 and subtilisin 168). Exemplary additional proteases include but are not limited to those described in WO92/21760, WO95/23221, WO2008010925, WO09/149200, WO09/149144, WO09/149145, WO 10/056640, WO10/056653, WO2010 0566356, WO11/072099, WO2011013022, WO11/140364, WO12/151534, WO2015038792, WO2015089447, WO2015089441, WO2015143360, WO2016061438, WO2016069548, WO 2016069544, WO2016069557, WO2016069563, WO2016069569, WO2016069552, WO2016 145428, WO2016183509, US Publ. No. 2008/0090747, U.S. Pat. Nos. 5,801,039, 5,340,735, 5,500,364, 5,855,625, RE34606, U.S. Pat. Nos. 5,955,340, 5,700,676, 6,312,936, 6,482,628, 8,530,219, U.S. Provisional Appl Nos. 62/331,282, 62/332,417, 62/343,618, and 62/351,649, and International Appl No. PCT/US2016/038245, as well as metalloproteases described in WO1999014341, WO 1999033960, WO1999014342, WO1999034003, WO2007044993, WO2009058303, WO2009 058661, WO2014071410, WO2014194032, WO2014194034, WO2014194054, and WO2014 194117. Exemplary additional proteases include, but are not limited to trypsin (e.g., of porcine or bovine origin) and the *Fusarium* protease described in WO89/06270.

Exemplary commercial proteases include, but are not limited to MAXATASE®, MAXACAL™, MAXAPEM™, OPTICLEAN®, OPTIMASE®, PROPERASE®, PURAFECT®, PURAFECT® OXP, PURAMAX™, EXCELLASE™, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST™ (DuPont); ALCALASE®, ALCALASE® ULTRA, BLAZE®, BLAZE® variants, BLAZE® EVITY®, BLAZE® EVITY® 16L, CORONASE®, SAVINASE®, SAVINASE® ULTRA, SAVINASE® EVITY®, SAVINASE® EVERTS®, PRIMASE®, DURAZYM™, POLARZYME®, OVOZYME®, KANNASE®, LIQUANASE®, LIQUANASE EVERTS®, NEUTRASE®, PROGRESS UNO®, RELASE®, and ESPERASE® (Novozymes); BLAP™ and BLAP™ variants (Henkel); LAVERGY™ PRO 104 L (BASF), KAP (*B. alkalophilus* subtilisin (Kao)) and BIOTOUCH® (AB Enzymes).

Another embodiment is directed to a composition comprising one or more subtilisin variant described herein and one or more lipase. In some embodiments, the composition comprises from about 0.00001% to about 10%, about 0.0001% to about 10%, about 0.001% to about 5%, about 0.001% to about 2%, or about 0.005% to about 0.5% lipase by weight composition. An exemplary lipase can be a chemically or genetically modified mutant. Exemplary lipases include, but are not limited to, e.g., those of bacterial or fungal origin, such as, e.g., *H. lanuginosa* lipase (see, e.g., EP 258068 and EP 305216), *T. lanuginosus* lipase (see, e.g., WO 2014/059360 and WO2015/010009), *Rhizomucor miehei* lipase (see, e.g., EP 238023), *Candida* lipase, such as *C. antarctica* lipase (e.g., *C. antarctica* lipase A or B) (see, e.g., EP 214761), *Pseudomonas* lipases such as *P. alcaligenes* and *P. pseudoalcaligenes* lipase (see, e.g., EP 218272), *P. cepacia* lipase (see, e.g., EP 331376), *P. stutzeri* lipase (see, e.g., GB 1,372,034), *P. fluorescens* lipase, *Bacillus* lipase (e.g., *B. subtilis* lipase (Dartois et al., Biochem. Biophys. Acta 1131: 253-260 (1993)), *B. stearothermophilus* lipase (see, e.g., JP 64/744992), and *B. pumilus* lipase (see, e.g., WO 91/16422)). Exemplary cloned lipases include, but not limited to *Penicillium camembertii* lipase (See, Yamaguchi et al., Gene 103:61-67 (1991)), *Geotricum candidum* lipase (See, Schimada et al., J. Biochem., 106:383-388 (1989)), and various *Rhizopus* lipases, such as, *R. delemar* lipase (See, Hass et al., Gene 109:117-113 (1991)), *R. niveus* lipase (Kugimiya et al., Biosci. Biotech. Biochem. 56:716-719 (1992)) and *R. oryzae* lipase. Other lipolytic enzymes, such as cutinases, may also find use in one or more composition describe herein, including, but not limited to, e.g., cutinase derived from *Pseudomonas mendocina* (see, WO 88/09367) and/or *Fusarium solani pisi* (see, WO90/09446). Exemplary commercial lipases include, but are not limited to M1 LIPASE™, LUMA FAST™, and LIPOMAX™ (DuPont);

LIPEX®, LIPOCLEAN®, LIPOLASE® and LIPOLASE® ULTRA (Novozymes); and LIPASE P™ (Amano Pharmaceutical Co. Ltd).

A still further embodiment is directed to a composition comprising one or more subtilisin variant described herein and one or more amylase. In one embodiment, the composition comprises from about 0.00001% to about 10%, about 0.0001% to about 10%, about 0.001% to about 5%, about 0.001% to about 2%, or about 0.005% to about 0.5% amylase by weight composition. Any amylase (e.g., alpha and/or beta) suitable for use in alkaline solutions may be useful to include in such composition. An exemplary amylase can be a chemically or genetically modified mutant. Exemplary amylases include, but are not limited to those of bacterial or fungal origin, such as, for example, amylases described in GB 1,296,839, WO9100353, WO9402597, WO94183314, WO9510603, WO9526397, WO9535382, WO9605295, WO9623873, WO9623874, WO 9630481, WO9710342, WO9741213, WO9743424, WO9813481, WO 9826078, WO9902702, WO 9909183, WO9919467, WO9923211, WO9929876, WO9942567, WO 9943793, WO9943794, WO 9946399, WO0029560, WO0060058, WO0060059, WO0060060, WO 0114532, WO0134784, WO 0164852, WO0166712, WO0188107, WO0196537, WO02092797, WO 0210355, WO0231124, WO 2004055178, WO2004113551, WO2005001064, WO2005003311, WO 2005018336, WO2005019443, WO2005066338, WO2006002643, WO2006012899, WO2006012902, WO2006031554, WO 2006063594, WO2006066594, WO2006066596, WO2006136161, WO 2008000825, WO2008088493, WO2008092919, WO2008101894, WO2008/112459, WO2009061380, WO2009061381, WO 2009100102, WO2009140504, WO2009149419, WO 2010/059413, WO 2010088447, WO2010091221, WO2010104675, WO2010115021, WO10115028, WO2010117511, WO 2011076123, WO2011076897, WO2011080352, WO2011080353, WO 2011080354, WO2011082425, WO2011082429, WO 2011087836, WO2011098531, WO2013063460, WO2013184577, WO 2014099523, WO2014164777, and WO2015077126. Exemplary commercial amylases include, but are not limited to AMPLIFY®, AMPLIFY PRIME®, BAN™, DURAMYL®, TERMAMYL®, TERMAMYL® ULTRA, FUNGAMYL®, STAINZYME®, STAINZYME PLUS®, STAINZYME ULTRA®, and STAINZYME EVITY® (Novozymes); EFFECTENZ™ S1000, POWERASE™, PREFERENZ™ S 100, PREFERENZ™ S110, EXCELLENZ™ S2000, RAPIDASE® and MAXAMYL® P (DuPont).

Yet a still further embodiment is directed to a composition comprising one or more subtilisin variant described herein and one or more cellulase. In one embodiment, the composition comprises from about 0.00001% to about 10%, 0.0001% to about 10%, about 0.001% to about 5%, about 0.001% to about 2%, or about 0.005% to about 0.5% cellulase by weight of composition. Any suitable cellulase may find used in a composition described herein. An exemplary cellulase can be a chemically or genetically modified mutant. Exemplary cellulases include but are not limited, to those of bacterial or fungal origin, such as, for example, is described in WO2005054475, WO2005056787, U.S. Pat. Nos. 7,449,318, 7,833,773, 4,435,307; EP 0495257; and U.S. Provisional Appl. No. 62/296,678. Exemplary commercial cellulases include, but are not limited to, CELLUCLEAN®, CELLUZYME®, CAREZYME®, ENDOLASE®, RENOZYME®, and CAREZYME® PREMIUM (Novozymes); REVITALENZ™ 100, REVITALENZ™ 200/220, and REVITALENZ® 2000 (DuPont); and KAC-500(B)™ (Kao Corporation). In some embodiments, cellulases are incorporated as portions or fragments of mature wild-type or variant cellulases, wherein a portion of the N-terminus is deleted (see, e.g., U.S. Pat. No. 5,874,276).

An even still further embodiment is directed to a composition comprising one or more subtilisin variant described herein and one or more mannanase. In one embodiment, the composition comprises from about 0.00001% to about 10%, about 0.0001% to about 10%, about 0.001% to about 5%, about 0.001% to about 2%, or about 0.005% to about 0.5% mannanase by weight composition. An exemplary mannanase can be a chemically or genetically modified mutant. Exemplary mannanases include, but are not limited to, those of bacterial or fungal origin, such as, for example, as is described in WO2016007929, U.S. Pat. Nos. 6,566,114, 6,602,842, and 6,440,991, and International Appl Nos. PCT/US2016/060850 and PCT/US2016/060844. Exemplary commercial mannanases include, but are not limited to MANNAWAY® (Novozymes) and EFFECTENZ™ M 1000, PREFERENZ® M 100, MANNASTAR®, and PURABRITE™ (DuPont).

A yet even still further embodiment is directed to a composition comprising one or more subtilisin variant described herein and one or more peroxidase and/or oxidase enzyme. In one embodiment, the composition comprises from about 0.00001% to about 10%, about 0.0001% to about 10%, about 0.001% to about 5%, about 0.001% to about 2%, or about 0.005% to about 0.5% peroxidase or oxidase by weight composition. A peroxidase may be used in combination with hydrogen peroxide or a source thereof (e.g., a percarbonate, perborate or persulfate) and an oxidase may be used in combination with oxygen. Peroxidases and oxidases are used for "solution bleaching" (i.e., to prevent transfer of a textile dye from a dyed fabric to another fabric when the fabrics are washed together in a wash liquor), alone or in combination with an enhancing agent (see, e.g., WO94/12621 and WO95/01426). An exemplary peroxidase and/or oxidase can be a chemically or genetically modified mutant. Exemplary peroxidases/oxidases include, but are not limited to those of plant, bacterial, or fungal origin.

Another embodiment is directed to a composition comprising one or more subtilisin variant described herein, and one or more perhydrolase, such as, for example, is described in WO2005/056782, WO2007/106293, WO 2008/063400, WO2008/106214, and WO2008/106215.

In yet another embodiment, the one or more subtilisin variant described herein and one or more additional enzyme contained in one or more composition described herein may each independently range to about 10%, wherein the balance of the cleaning composition is one or more adjunct material.

In some embodiments, one or more composition described herein finds use as a detergent additive, wherein said additive is in a solid or liquid form. Such additive products are intended to supplement and/or boost the performance of conventional detergent compositions and can be added at any stage of the cleaning process. In some embodiments, the density of the laundry detergent composition ranges from about 400 to about 1200 g/liter, while in other embodiments it ranges from about 500 to about 950 g/liter of composition measured at 20° C.

Some embodiments are directed to a laundry detergent composition comprising one or more subtilisin variant described herein and one or more adjunct material selected from surfactants, enzyme stabilizers, builder compounds, polymeric compounds, bleaching agents, additional enzymes, suds suppressors, dispersants, lime-soap dispersants, soil suspension agents, anti-redeposition agents, corrosion inhibitors, and combinations thereof. In some embodiments, the laundry compositions also contain softening agents.

Further embodiments are directed to manual dishwashing composition comprising one or more subtilisin variant described herein and one or more adjunct material selected from surfactants, organic polymeric compounds, suds enhancing agents, group II metal ions, solvents, hydrotropes, and additional enzymes.

Other embodiments are directed to one or more composition described herein, wherein said composition is a compact granular fabric cleaning composition that finds use in laundering colored fabrics or provides softening through the wash capacity, or is a heavy duty liquid (HDL) fabric cleaning composition. Exemplary fabric cleaning compositions and/or processes for making are described in U.S. Pat. Nos. 6,610,642 and 6,376,450. Other exemplary cleaning compositions are described, for example, in U.S. Pat. Nos. 6,605,458; 6,294,514; 5,929,022; 5,879,584; 5,691,297; 5,565,145; 5,574,005; 5,569,645; 5,565,422; 5,516,448; 5,489,392; and 5,486,303; 4,968,451; 4,597,898; 4,561,998; 4,550,862; 4,537,706; 4,515,707; and 4,515,705.

In some embodiments, the cleaning compositions comprise an acidifying particle or an amino carboxylic builder. Examples of an amino carboxylic builder include aminocarboxylic acids, salts and derivatives thereof. In some embodiment, the amino carboxylic builder is an aminopolycarboxylic builder, such as glycine-N,N-diacetic acid or derivative of general formula MOOC—CHR—N(CH$_2$COOM)$_2$ where R is C$_{1-12}$alkyl and M is alkali metal. In some embodiments, the amino carboxylic builder can be methylglycine diacetic acid (MGDA), GLDA (glutamic-N,N-diacetic acid), iminodisuccinic acid (IDS), carboxymethyl inulin and salts and derivatives thereof, aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl)aspartic acid (SEAS), N-(2-sulfomethyl)glutamic acid (SMGL), N-(2-sulfoethyl) glutamic acid (SEGL), IDS (iminodiacetic acid) and salts and derivatives thereof such as N-methyliminodiacetic acid (MIDA), alpha-alanine-N,N-diacetic acid (alpha-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts and derivative thereof. In some embodiments, the acidifying particle has a weight geometric mean particle size of from about 400μ to about 1200μ and a bulk density of at least 550 g/L. In some embodiments, the acidifying particle comprises at least about 5% of the builder.

In some embodiments, the acidifying particle can comprise any acid, including organic acids and mineral acids. Organic acids can have one or two carboxyls and in some instances up to 15 carbons, especially up to 10 carbons, such as formic, acetic, propionic, capric, oxalic, succinic, adipic, maleic, fumaric, sebacic, malic, lactic, glycolic, tartaric and glyoxylic acids. In some embodiments, the acid is citric acid. Mineral acids include hydrochloric and sulphuric acid. In some instances, the acidifying particle is a highly active particle comprising a high level of amino carboxylic builder. Sulphuric acid has also been found to further contribute to the stability of the final particle.

Additional embodiments are directed to a cleaning composition comprising one or more subtilisin variant and one or more surfactant and/or surfactant system, wherein the surfactant is selected from nonionic surfactants, anionic surfactants, cationic surfactants, ampholytic surfactants, zwitterionic surfactants, semi-polar nonionic surfactants, and mixtures thereof. In some embodiments, the surfactant is present at a level of from about 0.1 to about 60%, while in alternative embodiments the level is from about 1 to about 50%, while in still further embodiments the level is from about 5 to about 40%, by weight of the cleaning composition.

In some embodiments, one or more composition described herein comprises one or more detergent builders or builder systems. In one embodiment, the composition comprises from about 1%, from about 0.1% to about 80%, from about 3% to about 60%, from about 5% to about 40%, or from about 10% to about 50% builder by weight composition. Exemplary builders include, but are not limited to alkali metal; ammonium and alkanolammonium salts of polyphosphates; alkali metal silicates; alkaline earth and alkali metal carbonates; aluminosilicates; polycarboxylate compounds; ether hydroxypolycarboxylates; copolymers of maleic anhydride with ethylene or vinyl methyl ether, 1, 3, 5-trihydroxy benzene-2, 4, 6-trisulphonic acid, and carboxymethyloxysuccinic acid; ammonium and substituted ammonium salts of polyacetic acids such as ethylenediamine tetraacetic acid and nitrilotriacetic acid; polycarboxylates such as mellitic acid, succinic acid, citric acid, oxydisuccinic acid, polymaleic acid, benzene 1,3,5-tricarboxylic acid, carboxymethyloxysuccinic acid; and soluble salts thereof. In some such compositions, the builders form water-soluble hardness ion complexes (e.g., sequestering builders), such as citrates and polyphosphates, e.g., sodium tripolyphosphate, sodium tripolyphospate hexahydrate, potassium tripolyphosphate, and mixed sodium and potassium tripolyphosphate. Exemplary builders are described in, e.g., EP 2100949. In some embodiments, the builders include phosphate builders and non-phosphate builders. In some embodiments, the builder is a phosphate builder. In some embodiments, the builder is a non-phosphate builder. In some embodiments, the builder comprises a mixture of phosphate and non-phosphate builders. Exemplary phosphate builders include, but are not limited to mono-phosphates, di-phosphates, tri-polyphosphates or oligomeric-polyphosphates, including the alkali metal salts of these compounds, including the sodium salts. In some embodiments, a builder can be sodium tripolyphosphate (STPP). Additionally, the composition can comprise carbonate and/or citrate. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include the ammonium and/or alkali metal salts, i.e. the lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

In some embodiments, one or more composition described herein comprises one or more chelating agent. In one embodiment, the composition comprises from about 0.1% to about 15% or about 3% to about 10% chelating agent by weight composition. Exemplary chelating agents include, but are not limited to, e.g., copper, iron, manganese, and mixtures thereof.

In some embodiments, one or more composition described herein comprises one or more deposition aid. Exemplary deposition aids include, but are not limited to, e.g., polyethylene glycol; polypropylene glycol; polycarboxylate; soil release polymers, such as, e.g., polytelephthalic acid; clays such as, e.g., kaolinite, montmorillonite, atapulgite, illite, bentonite, and halloysite; and mixtures thereof.

In other embodiments, one or more composition described herein comprises one or more anti-redeposition agent or non-ionic surfactant (which can prevent the re-deposition of soils) (see, e.g., EP 2100949). For example, in ADW compositions, non-ionic surfactants find use for surface modification purposes, in particular for sheeting, to avoid filming and spotting and to improve shine. These non-ionic surfactants also find use in preventing the re-deposition of soils. In some embodiments, the non-ionic surfactant can be ethoxylated nonionic surfactants, epoxy-capped poly(oxyalkylated) alcohols and amine oxides surfactants.

In some embodiments, one or more composition described herein comprises one or more dye transfer inhibiting agent. Exemplary polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones, polyvinylimidazoles, and mixtures thereof. In one embodiment, the composition comprises from about 0.0001% to about 10%, about 0.01% to about 5%, or about 0.1% to about 3% dye transfer inhibiting agent by weight composition.

In some embodiments, one or more composition described herein comprises one or more silicate. Exemplary silicates include, but are not limited to, sodium silicates, e.g., sodium disilicate, sodium metasilicate, and crystalline phyllosilicates. In some embodiments, silicates are present at a level of from about 1% to about 20% or about 5% to about 15% by weight of the composition.

In some still additional embodiments, one or more composition described herein comprises one or more dispersant. Exemplary water-soluble organic materials include, but are not limited to, e.g., homo- or co-polymeric acids or their salts, in which the polycarboxylic acid comprises at least two carboxyl radicals separated from each other by not more than two carbon atoms.

In some further embodiments, one or more composition described herein comprises one or more non-peptidic enzyme stabilizer. In some embodiments, the enzyme stabilizer is water-soluble sources of calcium and/or magnesium ions. In some embodiments, the enzyme stabilizers include oligosaccharides, polysaccharides, and inorganic divalent metal salts, including alkaline earth metals, such as calcium salts. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), tin (II), cobalt (II), copper (II), nickel (II), and oxovanadium (IV)). Chlorides and sulfates also find use in some embodiments. Exemplary oligosaccharides and polysaccharides (e.g., dextrins) are described, for example, in WO 07/145964. In some embodiments, reversible protease inhibitors also find use, such as boron-containing compounds (e.g., borate, 4-formyl phenyl boronic acid, and phenyl-boronic acid derivatives (such for example, those described in WO96/41859) and/or a peptide aldehyde, such as, for example, is further described in WO2009/118375 and WO2013004636.

Peptide aldehydes may be used as protease stabilizers in detergent formulations as previously described (WO199813458, WO2011036153, US20140228274). Examples of peptide aldehyde stabilizers are peptide aldehydes, ketones, or halomethyl ketones and might be 'N-capped' with for instance a ureido (EP2358857B1), a carbamate, or a urea moiety, or 'doubly N-capped' with for instance a carbonyl, a ureido, an oxiamide, a thioureido, a dithiooxamide, or a thiooxamide moiety. The molar ratio of these inhibitors to the protease may be 0.1:1 to 100:1, e.g. 0.5:1-50:1, 1:1-25:1 or 2:1-10:1. Other examples of protease stabilizers are benzophenone or benzoic acid anilide derivatives, which might contain carboxyl groups (U.S. Pat. No. 7,968,508 B2). The molar ratio of these stabilizers to protease is preferably in the range of 1:1 to 1000:1 in particular 1:1 to 500:1 especially preferably from 1:1 to 100:1, most especially preferably from 1:1 to 20:1.

In some embodiments, one or more composition described herein comprises one or more bleach, bleach activator, and/or bleach catalyst. In some embodiments, one or more composition described herein comprises one or more inorganic and/or organic bleaching compound. Exemplary inorganic bleaches include, but are not limited to perhydrate salts, e.g., perborate, percarbonate, perphosphate, persulfate, and persilicate salts. In some embodiments, inorganic perhydrate salts are alkali metal salts. In some embodiments, inorganic perhydrate salts are included as the crystalline solid, without additional protection, although in some other embodiments, the salt is coated. Bleach activators are typically organic peracid precursors that enhance the bleaching action in the course of cleaning at temperatures of 60° C. and below. Exemplary bleach activators include compounds which, under perhydrolysis conditions, give aliphatic peroxoycarboxylic acids having from about 1 to about 10 carbon atoms or about 2 to about 4 carbon atoms, and/or optionally substituted perbenzoic acid. Exemplary bleach activators are described, for example, in EP 2100949. Exemplary bleach catalysts include, but are not limited to, manganese triazacyclononane and related complexes, as well as cobalt, copper, manganese, and iron complexes. Additional exemplary bleach catalysts are described, for example, in U.S. Pat. Nos. 4,246,612; 5,227,084; 4,810,410; WO 99/06521; and EP 2100949.

In some embodiments, one or more composition described herein comprises one or more catalytic metal complexes. In some embodiments, a metal-containing bleach catalyst finds use. In some embodiments, the metal bleach catalyst comprises a catalyst system comprising a transition metal cation of defined bleach catalytic activity (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof (see, e.g., U.S. Pat. No. 4,430,243). In some embodiments, one or more composition described herein is catalyzed by means of a manganese compound. Such compounds and levels of use are described, for example, in U.S. Pat. No. 5,576,282. In additional embodiments, cobalt bleach catalysts find use and are included in one or more composition described herein. Various cobalt bleach catalysts are described, for example, in U.S. Pat. Nos. 5,597,936 and 5,595,967.

In some additional embodiments, one or more composition described herein includes a transition metal complex of a macropolycyclic rigid ligand (MRL). As a practical matter, and not by way of limitation, in some embodiments, the compositions and cleaning processes described herein are adjusted to provide on the order of at least one part per hundred million, from about 0.005 ppm to about 25 ppm, about 0.05 ppm to about 10 ppm, or about 0.1 ppm to about 5 ppm of active MRL in the wash liquor. Exemplary MRLs include, but are not limited to special ultra-rigid ligands that are cross-bridged, such as, e.g., 5,12-diethyl-1,5,8,12-tetraazabicyclo(6.6.2)hexadecane. Exemplary metal MRLs are described, for example, in WO 2000/32601 and U.S. Pat. No. 6,225,464.

In another embodiment, one or more composition described herein comprises one or more metal care agent. In some embodiments, the composition comprises from about 0.1% to about 5% metal care agent by weight composition. Exemplary metal care agents include, for example, aluminum, stainless steel, and non-ferrous metals (e.g., silver and copper). Additional exemplary metal care agents are described, for example, in EP 2100949, WO 94/26860, and WO 94/26859. In some compositions, the metal care agent is a zinc salt.

In some embodiments, the cleaning composition is a heavy-duty liquid (HDL) composition comprising one or more subtilisin variant described herein. The HDL liquid laundry detergent can comprise a detersive surfactant (10-40%) comprising anionic detersive surfactant selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof; and optionally non-ionic surfactant selected from a group of linear or branched or random chain, substituted or unsubstituted alkyl alkoxylated alcohol, for example, a $C_8$-$C_{18}$alkyl ethoxylated alcohol and/or $C_6$-$C_{12}$alkyl phenol alkoxylates, optionally wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from alkanolamine sulpho-betaines); ampholytic surfactants; semi-polar non-ionic surfactants; and mixtures thereof.

In another embodiment, the cleaning composition is a liquid or gel detergent, which is not unit dosed, that may be aqueous, typically containing at least 20% and up to 95% water by weight, such as up to about 70% water by weight, up to about 65% water by weight, up to about 55% water by weight, up to about 45% water by weight, or up to about 35% water by weight. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

The composition can comprise optionally, a surfactancy boosting polymer consisting of amphiphilic alkoxylated grease cleaning polymers selected from a group of alkoxylated polymers having branched hydrophilic and hydrophobic properties, such as alkoxylated polyalkylenimines in the range of 0.05 wt %-10 wt % and/or random graft polymers typically comprising a hydrophilic backbone comprising monomers selected from the group consisting of: unsaturated $C_1$-$C_6$carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: $C_4$-$C_{25}$alkyl group, polypropylene, polybutylene, vinyl ester of a saturated $C_2$-$C_6$mono-carboxylic acid, $C_1$-$C_6$alkyl ester of acrylic or methacrylic acid, and mixtures thereof.

The composition can comprise additional polymers such as soil release polymers including, for example, anionically end-capped polyesters, for example SRP1; polymers comprising at least one monomer unit selected from saccharide, dicarboxylic acid, polyol and combinations thereof, in random or block configuration; ethylene terephthalate-based polymers and co-polymers thereof in random or block configuration, for example, Repel-o-tex SF, SF-2 and SRP6, Texcare SRA100, SRA300, SRN100, SRN170, SRN240, SRN300 and SRN325, Marloquest SL; anti-redeposition polymers (0.1 wt % to 10 wt %, including, for example, carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof; vinylpyrrolidone homopolymer; and/or polyethylene glycol with a molecular weight in the range of from 500 to 100,000 Da); cellulosic polymer (including, for example, alkyl cellulose; alkyl alkoxyalkyl cellulose; carboxyalkyl cellulose; alkyl carboxyalkyl cellulose, examples of which include carboxymethyl cellulose, methyl cellulose, methyl hydroxyethyl cellulose, methyl carboxymethyl cellulose; and mixtures thereof); and polymeric carboxylate (such as, for example, maleate/acrylate random copolymer or polyacrylate homopolymer).

The composition can further comprise saturated or unsaturated fatty acid, preferably saturated or unsaturated $C_{12}$-$C_{24}$fatty acid (0-10 wt %); deposition aids (including, for example, polysaccharides, cellulosic polymers, polydiallyl dimethyl ammonium halides (DADMAC), and copolymers of DADMAC with vinyl pyrrolidone, acrylamides, imidazoles, imidazolinium halides, and mixtures thereof, in random or block configuration; cationic guar gum; cationic cellulose such as cationic hydoxyethyl cellulose; cationic starch; cationic polyacylamides; and mixtures thereof.

The composition can further comprise dye transfer inhibiting agents examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

The composition can further comprise silicone or fatty-acid based suds suppressors; an enzyme stabilizer; hueing dyes, calcium and magnesium cations, visual signaling ingredients, anti-foam (0.001 to about 4.0 wt %), and/or structurant/thickener (0.01-5 wt %) selected from the group consisting of diglycerides, triglycerides, ethylene glycol distearate, microcrystalline cellulose, cellulose based materials, microfiber cellulose, biopolymers, xanthan gum, gellan gum, and mixtures thereof.

In some embodiments, the cleaning composition is a heavy duty powder (HDD) composition comprising one or more subtilisin variant described herein. The HDD powder laundry detergent can comprise a detersive surfactant including anionic detersive surfactants (selected from linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (selected from 1 linear or branched or random chain, substituted or unsubstituted $C_8$-$C_{18}$ alkyl ethoxylates, and/or $C_6$-$C_{12}$ alkyl phenol alkoxylates), cationic detersive surfactants (selected from alkyl pyridinium compounds, alkyl quaternary ammonium compounds, alkyl quaternary phosphonium compounds, alkyl ternary sulphonium compounds, and mixtures thereof); zwitterionic and/or amphoteric detersive surfactants (selected from alkanolamine sulpho-betaines); ampholytic surfactants; semi-polar non-ionic surfactants and mixtures thereof; builders (phosphate free builders, e.g., zeolite builders examples of which include zeolite A, zeolite X, zeolite P and zeolite MAP in the range of 0 to less than 10 wt %); phosphate builders, e.g., sodium tripolyphosphate in the range of 0 to less than 10 wt %; citric acid, citrate salts and nitrilotriacetic acid or salt thereof in the range of less than 15 wt %; silicate salt (sodium or potassium silicate or sodium meta-silicate in the range of 0 to less than 10 wt % or layered silicate (SKS-6)); carbonate salt (sodium carbonate and/or sodium bicarbonate in the range of 0 to less than 10 wt %); and bleaching agents (photobleaches, e.g., sulfonated zinc phthalocyanines, sulfonated aluminum phthalocyanines, xanthenes dyes, and mixtures thereof); hydrophobic or hydrophilic bleach activators (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, and nonanoyloxybenzene sulfonate-NOBS, nitrile quats, and mixtures thereof); hydrogen peroxide; sources of hydrogen peroxide (inorganic perhydrate salts, e.g., mono or tetra hydrate sodium salt of perborate, percarbonate, persulfate, perphosphate, or persilicate); preformed hydrophilic and/or hydrophobic peracids (selected from percarboxylic acids and salts, percarbonic acids and salts, perimidic acids and salts, peroxymonosulfuric acids and salts, and mixtures thereof); and/or bleach catalyst (e.g., imine bleach boosters, such as iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof), metal-containing bleach catalyst (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid) and water-soluble salts thereof).

The composition can further comprise additional detergent ingredients including perfume microcapsules, starch encapsulated perfume accord, an enzyme stabilizer, hueing agents, additional polymers including fabric integrity and cationic polymers, dye lock ingredients, fabric-softening agents, brighteners (for example C.I. Fluorescent brighteners), flocculating agents, chelating agents, alkoxylated polyamines, fabric deposition aids, and/or cyclodextrin.

In some embodiments, the cleaning composition is an ADW detergent composition comprising one or more subtilisin variant described herein. The ADW detergent composition can comprise two or more non-ionic surfactants selected from ethoxylated non-ionic surfactants, alcohol alkoxylated surfactants, epoxy-capped poly(oxyalkylated) alcohols, and amine oxide surfactants present in amounts from 0-10% by wt; builders in the range of 5-60% by wt. comprising either phosphate (mono-phosphates, di-phosphates, tri-polyphosphates or oligomeric-poylphosphates), sodium tripolyphosphate-STPP or phosphate-free builders (amino acid based compounds, e.g., MGDA (methyl-glycine-diacetic acid) and salts and derivatives thereof, GLDA (glutamic-N,Ndiacetic acid) and salts and derivatives thereof, IDS (iminodisuccinic acid) and salts and derivatives thereof, carboxy methyl inulin and salts and derivatives thereof and mixtures thereof, nitrilotriacetic acid (NTA), diethylene triamine penta acetic acid (DTPA), and B-alaninediacetic acid (B-ADA) and their salts), homopolymers and copolymers of polycarboxylic acids and their partially or completely neutralized salts, monomeric polycarboxylic acids and hydroxycarboxylic acids and their salts in the range of 0.5-50% by wt; sulfonated/carboxylated polymers (provide dimensional stability to the product) in the range of about 0.1 to about 50% by wt; drying aids in the range of about 0.1 to about 10% by wt (selected from polyesters, especially anionic polyesters optionally together with further monomers with 3-6 functionalities which are conducive to polycondensation, specifically acid, alcohol or ester functionalities, polycarbonate-, polyurethane- and/or polyurea-polyorganosiloxane compounds or precursor compounds thereof of the reactive cyclic carbonate and urea type); silicates in the range from about 1 to about 20% by wt (sodium or potassium silicates, e.g., sodium disilicate, sodium meta-silicate and crystalline phyllosilicates); bleach-inorganic (e.g., perhydrate salts such as perborate, percarbonate, perphosphate, persulfate and persilicate salts) and organic (e.g., organic peroxyacids including diacyl and tetraacylperoxides, especially diperoxydodecanedioc acid, diperoxytetradecanedioc acid, and diperoxyhexadecanedioc acid); bleach activator-organic peracid precursors in the range from about 0.1 to about 10% by wt; bleach catalysts (selected from manganese triazacyclononane and related complexes, Co, Cu, Mn and Fe bispyridylamine and related complexes, and pentamine acetate cobalt(III) and related complexes); metal care agents in the range from about 0.1-5% by wt (selected from benzatriazoles, metal salts and complexes, and silicates); enzymes in the range from about 0.01-5.0 mg of active enzyme per gram of ADW detergent composition (acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, nucleases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, xylosidases, and mixtures thereof); and enzyme stabilizer components (selected from oligosaccharides, polysaccharides and inorganic divalent metal salts).

More embodiments are directed to compositions and methods of treating fabrics (e.g., to desize a textile) using one or more subtilisin variant described herein. Fabric-treating methods are well known in the art (see, e.g., U.S. Pat. No. 6,077,316). For example, the feel and appearance of a fabric can be improved by a method comprising contacting the fabric with a variant described herein in a solution. The fabric can be treated with the solution under pressure.

One or more subtilisin variant described herein can be applied during or after weaving a textile, during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. One or more subtilisin variant described herein can be applied during or after weaving to remove the sizing starch or starch derivatives. After weaving, the variant can be used to remove the size coating before further processing the fabric to ensure a homogeneous and wash-proof result. One or more subtilisin variant described herein can be used alone or with other desizing chemical reagents and/or desizing enzymes to desize fabrics, including cotton-containing fabrics, as detergent additives, e.g., in aqueous compositions. An amylase also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of proteolytic enzymes to provide softness to the fabric and make the cotton more accessible to the subsequent enzymatic finishing steps. One or more subtilisin variant described herein can be used in methods of finishing denim garments (e.g., a “bio-stoning process”), enzymatic desizing and providing softness to fabrics, and/or finishing process.

One or more subtilisin variant described herein can be used to remove proteins from animals and their subsequent degradation or disposal, such as, e.g., feathers, skin, hair, and hide. In some instances, immersion of the animal carcass in a solution comprising one or more subtilisin variant described herein can act to protect the skin from damage in comparison to the traditional immersion in scalding water or the defeathering process. In one embodiment, feathers can be sprayed with one or more subtilisin variant described herein under conditions suitable for digesting or initiating degradation of the plumage. In some embodiments, the variant can be used in combination with an oxidizing agent.

In some embodiments, the removal of the oil or fat associated with raw feathers can be assisted by one or more subtilisin variant described herein. In some embodiments, one or more subtilisin variant described herein is used in compositions for cleaning the feathers as well as to sanitize and partially dehydrate the fibers. In yet other embodiments, one or more subtilisin variant described herein finds use in recovering protein from plumage. In some other embodiments, one or more subtilisin variant described herein is applied in a wash solution in combination with 95% ethanol or other polar organic solvent with or without a surfactant at about 0.5% (v/v). In other embodiments, one or more subtilisin variant described herein may be used alone or in combination in suitable feather processing and proteolytic methods, such as those disclosed in PCT/EP2013/065362, PCT/EP2013/065363, and PCT/EP2013/065364. In some embodiments, the recovered protein can be subsequently used in animal or fish feed.

In still another embodiment, one or more animal feed composition, animal feed additive and/or pet food comprises one or more subtilisin variant described herein. Other embodiments are directed to methods for preparing such an animal feed composition, animal feed additive composition and/or pet food comprising mixing one or more subtilisin variant described herein with one or more animal feed ingredients and/or animal feed additive ingredients and/or pet food ingredients.

The term “animal” includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment, the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term “pet food” is understood to mean a food for a household animal such as, but not limited to, dogs, cats, gerbils, hamsters, chinchillas, fancy rats, guinea pigs; avian pets, such as canaries, parakeets, and parrots; reptile pets, such as turtles, lizards and snakes; and aquatic pets, such as tropical fish and frogs.

The terms “animal feed composition,” “feedstuff” and “fodder” are used interchangeably and can comprise one or more feed materials selected from a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; and e) minerals and vitamins.

One or more subtilisin variant described herein finds further use in the enzyme aided bleaching of paper pulps such as chemical pulps, semi-chemical pulps, kraft pulps, mechanical pulps or pulps prepared by the sulfite method. In general terms, paper pulps are incubated with one or more subtilisin variant described herein under conditions suitable for bleaching the paper pulp.

In some embodiments, the pulps are chlorine free pulps bleached with oxygen, ozone, peroxide or peroxyacids. In some embodiments, one or more subtilisin variant described herein is used in enzyme aided bleaching of pulps produced by modified or continuous pulping methods that exhibit low lignin contents. In some other embodiments, one or more subtilisin variant described herein is applied alone or preferably in combination with xylanase and/or endoglucanase and/or alpha-galactosidase and/or cellobiohydrolase enzymes.

In other embodiments, one or more subtilisin variant described herein finds further use in the enzyme aided debridement of tissue. This involves the removal of dead or damaged tissue, for example, removal from wounds to aid in healing.

In even further embodiments, one or more subtilisin variant described herein finds further use in tissue culture. In particular, one or more subtilisin variant described herein can be used to suspend or resuspend cells adherent to a cell culture wall, such as during the process of harvesting cells. In another embodiment, one or more subtilisin variant described herein can be used to cleave protein bonds between cultured cells and the dish, allowing cells to become suspended in solution.

In yet another embodiment, one or more subtilisin variant described herein finds further use as a food additive, a digestive aide, and/or a food processing aid.

In still yet another embodiment, one or more subtilisin variant described herein finds further use in leather processing by removing hair from animal hides, soaking, degreasing, or bating, which is a process involving degradation of non-structural proteins during leather making.

EXAMPLES

The following examples are provided to demonstrate and illustrate certain preferred embodiments and aspects of the present disclosure and should not be construed as limiting.

Example 1

Expression of *B. gibsonii*-Clade Subtilisin Variants

DNA manipulations to generate *B. gibsonii*-clade subtilisin variants were carried out using conventional molecular biology techniques (see, e.g., Sambrook et al, Molecular Cloning: Cold Spring Harbor Laboratory Press). A series of artificial DNA sequences were generated, coding for mature *B. gibsonii*-clade subtilisin sequences that introduce multiple amino acid modifications into the sequence of the wildtype *B. gibsonii*-clade Bgi02446 protease (accession number AGS78407.1). All subtilisin variants were expressed and recovered as described below. The *B. gibsonii*-Glade is more fully described in International Patent Application No. PCT/US2014/070107, filed Jun. 17, 2016.

An artificial DNA sequence was generated coding for mature wildtype *B. gibsonii*-clade Bgi02446 protease (SEQ ID NO:1) and expressed in a suitable *B. subtilis* strain as described below.

For the expression of the WALB SP-2983 subtilisin (SEQ ID NO:8), a DNA fragment comprising: a 5'AprE flanking region that contains the *B. subtilis* P1 rrnI promoter sequence (SEQ ID NO:2) (the *B. subtilis* P1 rrnI promoter is more fully described in US-2014-0329309), the aprE signal peptide sequence (SEQ ID NO:3), the pro sequence from *B. lentus* (SEQ ID NO:4), the sequence corresponding to the gene for the *B. gibsonii*-Glade subtilisin variant WALBSP-2983 (SEQ ID NO:5), the BPN' terminator (SEQ ID NO:6), the chloramphenicol acetyl transferase (CAT) gene expression cassette from *S. aureus* (SEQ ID NO:7) and the 3'AprE flanking sequence (SEQ ID NO:9), in consecutive order was assembled using standard molecular techniques. The amino acid sequence of the *B. subtilis* aprE signal peptide encoded by SEQ ID NO:3 is set forth as SEQ ID NO:10. The amino acid sequence of the pro sequence encoded by SEQ ID NO:4 is set forth as SEQ ID NO:11. The amino acid sequence of the protein encoded by the WALBSP-2983 gene is set forth as SEQ ID NO:8. This linear WALBSP-2983 expression cassette was used to transform 200 uL of competent *B. subtilis* cells of a suitable strain. The transformed cells were incubated at 37° C. for 1 hour while shaking at 250 rpm. The transformation mixture was plated onto LA plates containing 1.6% skim milk and 5 ppm chloramphenicol (CMP) and incubated overnight at 37° C. Single colonies were picked and grown in Luria broth+5 ppm CMP at 37° C. Strain samples were frozen at −80° C. with 20% glycerol for storage. Other *B. gibsonii*-Glade subtilisin variants were expressed by using the appropriate gene of interest in place of (SEQ ID NO:5).

For the expression of certain *B. gibsonii* Glade variants, the genomic DNA of the *B. subtilis* strain expressing WALBSP-2983 was isolated and used as a template to generate variants of the WALB SP-2983 mature protease region. A library of variants containing specific amino acid substitutions was created using a polymerase chain reaction with appropriate primer pairs, DNA template, and Q5 polymerase (New England Biolabs). These assembled fragments were used to transform competent *B. subtilis* cells and the transformants were handled as described above.

In some instances, the *B. gibsonii*-Glade subtilisins were produced in *B. subtilis* using an expression cassette consisting of the *B. subtilis* aprE promoter (SEQ ID NO:12), the *B. subtilis* aprE signal peptide sequence (SEQ ID NO:3), the *B. lentus* pro-sequence (SEQ ID NO:4), the mature protease sequences for each of the artificial sequences, and a BPN' terminator (SEQ ID NO:6). The expression cassettes were cloned into replicating shuttle vectors and transformed into a suitable *B. subtilis* strain. The *B. subtilis* host strains transformed with the various pHYT plasmids, as described in WO2016205755 patent application, were cultivated in an enriched semi-defined media based on MOPs buffer, with urea as major nitrogen source, glucose as the main carbon source, and supplemented with 1% soytone for robust cell growth. After incubation, the secreted proteases were isolated from the growth medium by centrifugation and filtration. Clarified culture supernatants were used for assays and purification as described below.

The sequence of each *B. gibsonii*-clade subtilisin variant was confirmed by DNA sequence analysis. Protease samples for the studies described below were generated by culturing cells in selective growth medium in a 96-well MTP at 31° C. for 68 hours. Culture supernatant was prepared by centrifugation and filtration.

Example 2

Assays

Protein Determination

The concentration of the *B. gibsonii*-clade proteases in culture supernatant was determined by UHPLC using a Zorbax 300 SB-C3 column and linear gradient of 0.1% Trifluoroacetic acid (Buffer A) and 0.07% Trifluoroacetic acid in Acetonitrile (Buffer B) and detection at 220 nm. Culture supernatants were diluted in 10 mM NaCl, 0.1 mM $CaCl_2$), 0.005% TWEEN®-80 surfactant for loading onto column. The protein concentration of the samples was calculated using a standard curve of the purified parent enzyme.

Protease Activity

The protease activity of parent and variants thereof was tested by measuring the hydrolysis of AAPF-pNA synthetic peptidic substrate or dimethyl casein (DMC). For the AAPF assay, the reagent solutions used were: 100 mM Tris pH 8.6, 10 mM $CalCl_2$, 0.005% Tween®-80 (Tris/Ca buffer) and 160 mM suc-AAPF-pNA in DMSO (suc-AAPF-pNA stock solution) (Sigma: S-7388). To prepare a working solution, 1 mL suc-AAPF-pNA stock solution was added to 100 mL Tris/Ca buffer and mixed. An enzyme sample was added to a microtiter plate (MTP) containing 1 mg/mL suc-AAPF-pNA working solution and assayed for activity at 405 nm over 3-5 min using a SpectraMax plate reader in kinetic mode at RT. The protease activity was expressed as mOD/min.

The reagent solutions used for the DMC assay were: 2.5% w/v DMC (Sigma C-9801) in 100 mM sodium carbonate buffer pH 9.5, 0.075% TNBSA (Thermo Scientific) in Reagent A. Reagent A: 45.4 g $Na_2B_4O_7{\cdot}10H_2O$ in 15 mL 4 N NaOH to reach a final volume of 1000 mL in deionized water. Equal volumes of DMS substrate and TNBSA in Reagent A were mixed in MTPs and protease samples were added with slow missing. Activity was measured at 405 nm over 3 min using a SpectraMax plate reader in kinetic mode at RT.

Stability Assay in Tris-EDTA

Enzyme stability was measured in Tris-EDTA (50 mM Tris pH9; 1-5 mM EDTA; 0.005% Tween) buffered conditions. Percent residual activities were calculated by taking a ratio of the stressed to unstressed activity and multiplying by 100. Stability PIs were obtained by dividing the residual activity of the *B. gibsonii*-clade variant protease by that of the parent protease Bgi02446.

Automatic Dishwashing Cleaning Assays

Crème Brûlée stain: The cleaning performance of *B. gibsonii*-clade subtilisin variants on crème brûlée stain was tested by using DM10 melamine tiles prepared by CFT in Vlaardingen, the Netherlands as set forth herein. Crème brûlée on melamine tiles were prepared by CFT according to the IKW method set forth in "Recommendations for the Quality Assessment of the Cleaning Performance of Dishwasher Detergents (Part B, Update 2015)", 9. Crème Brûlée, IKW p46, Sofw Journal—142-06/16. (see, www.ikw.org/fileadmin/content/downloads/Haushaltspflege/2016_EQ_Dishwasher_Detergents_Part_B_Update_2015.pdf (last visited Dec. 14, 2016)) using either 1.7 or 2.5 g of material per tile.

The melamine tiles were used as a lid and tightly pressed onto a microtiter plate (MTP). 3 g/L of ADW detergent solution adjusted to 374 ppm water hardness and each enzyme sample were added to the MTP prior to attaching the melamine tile lid to the MTP. The volume capacity of the MTP, and therefore the volume of solution added thereto, may vary, wherein a minimal volume of solution that enables contact between solution and stain surface should be added to the MTP. In this example, a volume of 3004, of detergent containing enzyme was added to each well of an aluminum 96-well MTP. The MTPs were incubated in an Infors thermal shaker for 45 min at 40° C., unless otherwise specified, at 250 rpm. After incubation, the tiles were removed from the MTP and air-dried.

In some instances, stain removal was quantified using red, green and blue (RGB) measurements taken with a scanner (MiCrotek Scan Maker 900). Images were imported into Photoshop CSII to extract the RGB values from the stain areas using IPTK 5.0 software from Reindeer Graphics. In other instances, stain removal was quantified by photographing the plates and measuring the RGB values from each stain area using custom software.

Percent Soil removal (% SRI) values of the washed tiles were calculated by using the RGB values in the following formula:

$$\%\ SRI=(\Delta E/\Delta E_{initial})*100$$

$$\text{Where } \Delta E=\text{SQR}((R_{after}-R_{before})^2+(G_{after}-G_{before})^2+(B_{after}-B_{before})^2)$$

$$\text{Where } \Delta E=\text{SQR}((R_{white}-R_{before})^2+(G_{white}-G_{before})^2+(B_{white}-B_{before})^2)$$

Cleaning performance was obtained by subtracting the value of a blank control (no enzyme) from each sample value (hereinafter "blank subtracted cleaning"). For each condition and *B. gibsonii*-clade subtilisin variant, a performance index (PI) was calculated by dividing the blank subtracted cleaning by that of the parent protease at the same concentration. The value for the parent protease PI was determined from a standard curve of the parent protease which was included in the test and which was fitted to a Langmuir fit or Hill Sigmoidal fit.

Egg yolk stain: The cleaning performance of *B. gibsonii*-clade subtilisin variants on egg yolk microswatches (PAS-38, Center for Testmaterials BV, Vlaardingen, Netherlands) was measured on pre-rinsed or unrinsed swatches. To prepare rinsed PAS38 swatches, 180 µl 10 mM CAPS buffer of pH 11 was added to MTPs containing PAS38 microswatches. The plates were sealed and incubated in an iEMS incubator for 30 min at 60° C. and 1100 rpm shaking. After this incubation, the buffer was removed and the swatches were rinsed with deionized water to remove any residual buffer. The plates were then air dried prior to use in the performance assay. The microswatch plates were filled with 3 g/l ADW detergent solution in 374 ppm water hardness prior to enzyme addition with a final enzyme concentration between 0.05 and 10 ppm.

Following incubation of PAS-38 swatches with detergents and enzymes for 30 minutes at 40° C., the absorbance was read at 405 nm using a SpectraMax plate reader. Absorbance results were obtained by subtracting the value for a blank control (no enzyme) from each sample value (hereinafter "blank subtracted absorbance"). For each condition and *B. gibsonii*-clade protease, a performance index (PI) was calculated by dividing the blank subtracted absorbance by that of the Bgi02446 parent protease at the same concentration.

Liquid Laundry Cleaning Assays

Variants were tested for cleaning performance relative to parent on various technical soils: BMI (EMPA-116, blood/milk/ink on cotton) stain. The BMI swatches were pre-rinsed with deionized water for 20 minutes and dried overnight at room temperature. Pre-punched swatches in MTP plates (Costar 9017 or Greiner 655101) were prepared by Center for Testmaterials BV, Vlaardingen, Netherlands. These microswatch-containing plates were filled with detergent prior to enzyme addition. Aliquots of enzyme were added to detergent-filled MTPs containing microswatches to reach a final volume of 180 microliters for laundry assays with a final enzyme concentration between 0.05-10 ppm. Laundry cleaning assays were carried out at 25° C. for 20 min. Following incubation, 100-150 uL of supernatant was transferred to a fresh MTP and absorbance was read at 600 nm using a SpectraMax plate reader. Absorbance results were obtained by subtracting the value for a blank control (no enzyme) from each sample value. The cleaning PI for each assay condition was obtained by dividing the absorbance values for a given variant by that of the Parent, tested at the same concentration. The Parent PI value was determined by fitting the standard curve of the purified Parent sample to a Langmuir fit.

Detergents

Various detergent formulas were used as listed below. Automatic dishwashing (ADW) cleaning assays were performed using the following detergents at the final concentrations shown in brackets: GSM-B detergent (3 g/L) (GSM-B Phosphate-free ADW detergent purchased without enzymes from WFK Testgewebe GmbH, Brüggen, Deutschland (www.testgewebe.de), composition shown on Table 1), MGDA detergent (3 g/L) (composition shown on Table 2), ADW model detergent A (3.34 g/L) (composition shown on Table 3), ADW model detergent B (3.18 g/L) (composition shown on Table 4) and ADW model detergent C (3.26 g/L) (composition shown on Table 5).

Laundry (HDL) cleaning assays were performed using Persil Small & Mighty Non-Bio Liquid Detergent "Persil Non-Bio" (PNB, Unilever) purchased in 2014 from local supermarkets. The HDL detergents Persil Non-Bio, and CNS are considered boron-free since they contained ≤5 mg/Kg of boron, when tested for elemental boron content. HDL assays were conducted at a final detergent concentration of 2.7 g/L, at 200-500 ppm water hardness and pH was adjusted to 8.2 using 5 mM HEPES buffer.

TABLE 1

GSM-B pH 10.5 Phosphate-Free ADW Detergent Ingredients

| Component | Weight % |
|---|---|
| Sodium citrate dehydrate | 30.0 |
| Maleic acid/acrylic acid copolymer sodium salt (SOKALAN ® CP5; BASF) | 12.0 |
| Sodium perborate monohydrate | 5.0 |
| TAED | 2.0 |
| Sodium disilicate: Protil A (Cognis) | 25.0 |
| Linear fatty alcohol ethoxylate | 2.0 |
| Sodium carbonate anhydrous | add to 100 |

TABLE 2

MGDA ADW Detergent Ingredients

| Component | Weight % |
|---|---|
| MGDA | 64.6 |
| Plurafac SLF 18-45D | 4.4 |
| Bismuthcitrate | 0.4 |
| Phosphonates (Bayhibit S) | 0.4 |
| Acusol 420/Acosul 587 | 1.6 |
| PEG6000 | 2.4 |
| PEG1500 | 5.9 |
| Sodium percarbonate | 16.1 |
| TAED | 4.1 |

TABLE 3

ADW model detergent formula A

| | (Active weight %) |
|---|---|
| Solid Ingredients | |
| Sodium carbonate | 41.7 |
| Sodium sulphate | 0.00 |
| MGDA (Three-sodium Methyl glycine diacetate supplied by BASF) | 21.0 |
| TAED (Tetraacetylethylenediamine) | 1.68 |
| Sodium percarbonate | 12.6 |
| Sulfonated polymer (Acusol 588 supplied by Dow Chemicals) | 2.5 |
| Bleach catalyst (MnTACN, Manganese 1,4,7-Triazacyclononane) | 1.2 |
| Amylase (Stainzyme ® Plus supplied by Novozymes) | 0.11 |
| Liquid ingredients | |
| Lutensol TO7 (Nonionic surfactant supplied by BASF) | 19.3 |

TABLE 4

ADW model detergent formula B

| | (Active weight %) |
|---|---|
| Solid Ingredients | |
| Sodium carbonate | 41.7 |
| Sodium sulphate | 1.68 |
| Citrate | 19.2 |
| TAED (Tetraacetylethylenediamine) | 1.68 |
| Sodium percarbonate | 12.6 |
| Sulfonated polymer (Acusol 588 supplied by Dow Chemicals) | 2.5 |
| Bleach catalyst (MnTACN, Manganese 1,4,7-Triazacyclononane) | 1.2 |
| Amylase (Stainzyme ® Plus supplied by Novozymes) | 0.11 |
| Liquid ingredients | |
| Lutensol TO7 (Nonionic surfactant supplied by BASF) | 19.3 |

TABLE 5

ADW model detergent formula C

| | (Active weight %) |
|---|---|
| Solid Ingredients | |
| Sodium carbonate | 41.7 |
| Sodium sulphate | 2.03 |
| MGDA (Three-sodium Methyl glycine diacetate supplied by BASF) | 10.1 |
| Citrate | 10.1 |
| TAED (Tetraacetylethylenediamine) | 1.68 |
| Sodium percarbonate | 12.6 |
| Sulfonated polymer (Acusol 588 supplied by Dow Chemicals) | 2.5 |
| Bleach catalyst MnTACN (Manganese 1,4,7-Triazacyclononane) | 1.2 |
| Amylase (Stainzyme ® Plus supplied by Novozymes) | 0.11 |
| Liquid ingredients | |
| Lutensol TO7 (Nonionic surfactant supplied by BASF) | 19.3 |

Example 3

The Productivity of Various *B. gibsonii*-Clade Subtilisin Variants

*B. gibsonii*-clade subtilisin variants listed below in Table 6 were produced as set forth for WALB SP-2983 in Example 1. The amino acid substitutions of the variants are set forth relative to *B. gibsonii*-clade Bgi02446 wild-type (SEQ ID NO:1). The concentration of each variant in culture supernatant was determined by UHPLC as described above in Example 2. The protein concentration of the samples was calculated based on a standard curve of the purified parent enzyme (Bgi02446 wild-type). The protein concentration of each variant containing the N242D mutation is set forth in Table 6, expressed as a PI value. The PI value was calculated by dividing the protein concentration of the variant containing the N242D mutation by the protein concentration of the variant without the N242D mutation.

TABLE 6

| Bgi02446 variants containing the N242D mutation, with improved productivity | | |
|---|---|---|
| *B. gibsonii*-clade Subtilisin | Substitutions With Respect to Bgi02446 | PI |
| WALBSP-03627 | A37T-S39E-A47V-T56Y-E87D-S99R-T114A-F128A-N242D | 1.33 |
| WALBSP-03657 | A37T-S39E-I43V-I80V-N85S-E87D-S99R-T114Q-N242D | 1.14 |
| WALBSP-03549 | A37T-S39E-I43V-N85S-E87D-S99R-T114Q-N242D | 1.33 |
| WALBSP-03307 | I43V-A47V-N242D | 1.15 |
| WALBSP-03303 | I43V-A47V-S99R-F128A-N242D | 1.36 |
| WALBSP-03376 | I43V-A47V-S99R-S126T-N242D | 1.48 |
| WALBSP-03322 | I43V-A47V-T56Y-T114Q-N242D | 1.56 |
| WALBSP-03612 | S39E-A47V-T56Y-N85S-S99R-T114Q-F128A-N242D | 1.36 |
| WALBSP-03337 | S39E-E87D-N242D | 1.54 |
| WALBSP-03378 | S39E-E87D-S99R-F128A-N242D | 1.55 |
| WALBSP-03357 | S39E-E87D-S99R-S126T-N242D | 1.45 |
| WALBSP-03319 | S39E-I43V-A47V-E87D-N242D | 1.40 |
| WALBSP-03632 | S39E-I43V-A47V-T56Y-I80V-E87D-S99R-T114Q-S126T-N242D | 1.27 |
| WALBSP-03533 | S39E-I43V-T56Y-S99R-T114Q-F128A-N242D | 1.34 |
| WALBSP-03339 | S39E-T56Y-E87D-T114Q-N242D | 1.52 |
| WALBSP-03372 | S99R-F128A-N242D | 1.61 |
| WALBSP-03511 | S99R-S126T-N242D | 1.54 |
| WALBSP-03323 | T56Y-S99R-T114Q-F128A-N242D | 1.33 |
| WALBSP-03353 | T56Y-S99R-T114Q-S126T-N242D | 1.50 |
| WALBSP-03343 | T56Y-T114Q-N242D | 1.40 |
| WALBSP-02983 | A37T-S39E-I43V-A47V-T56Y-I80V-N85S-E87D-S99R-T114Q-S126T-F128A-N242D | 1.54 |
| WALBSP-04903 | N242D | 1.27 |

Example 4

Automatic Dish Cleaning Performance and Stability of *B. gibsonii*-Clade Subtilisins The ADW cleaning performance and stability of *B. gibsonii*-clade subtilisin variants was measured using detergents and assays described on Example 2, and is reported on Tables 7, 8, 9, 10, and 11 where cleaning benefit is expressed as PI values versus the parent enzyme Bgi02446 Wild-type and stability is reported as percent remaining activity or as PI values versus the parent enzyme Bgi02446 Wild-type. ND denotes instances when results were Not Determined. The performance tests reported on Table 7 were carried out at 40° C.

TABLE 7

Crème Brûlée Cleaning Performance of *B. Gibsonii*-clade Subtilisin Variants, Expressed as PI versus Bgi02446 Wild-type

| | | PI versus Bgi02446 Wild-type | |
|---|---|---|---|
| *B. gibsonii*-Subtilisin | Amino Acid Substitutions With Respect to Bgi02446 Wild-type | MGDA detergent | GSM-B detergent |
| Bgi02446-WT | none | 1.0 | 1.0 |
| WALBSP-02983 | A37T-S39E-I43V-A47V-T56Y-I80V-N85S-E87D-S99R-T114Q-S126T-F128A-N242D | 1.3 | 1.2 |
| WALBSP-03779 | A37T-S39E-I43V-A47V-T56Y-I80V-N85S-E87D-S99T-T114Q-S126G-N242D | 1.4 | 2 |
| WALBSP-03780 | A37T-S39E-I43V-A47V-T56Y-I80V-N85S-E87D-S99R-T114Q-S126V-D127G-A128E-F128A-N242D | 1.3 | 1.6 |
| WALBSP-03789 | A37T-S39E-I43V-A47V-T56Y-I80V-N85S-E87D-S99I-T114Q-S126T-D127E-F128I-N242D | 1.5 | 1.9 |
| WALBSP-03794 | A37T-S39E-I43V-A47V-T56Y-I80V-N85S-E87D-S99H-T114Q-D127S-F128Q-N242D | 1.5 | 1.6 |
| WALBSP-03800 | A37T-S39E-I43V-A47V-T56Y-I80V-N85S-E87D-S99N-T114Q-S126T-D127Q-N242D | 0.9 | 1.1 |
| WALBSP-03806 | A37T-S39E-I43V-A47V-T56Y-I80V-N85S-E87D-S99H-T114Q-D127Q-F128N-N242D | 1.2 | 1.3 |
| WALBSP-03807 | A37T-S39E-I43V-A47V-T56Y-I80V-N85S-E87D-S99T-T114Q-S126G-D127G-F128V-N242D | 1.0 | 1.1 |
| WALBSP-03808 | A37T-S39E-I43V-A47V-T56Y-I80V-N85S-E87D-S99K-T114Q-S126G-D127G-F128G-N242D | 1.3 | 1.2 |
| WALBSP-03810 | A37T-S39E-I43V-A47V-T56Y-I80V-N85S-E87D-T114Q-D127L-F128V-N242D | 1.3 | 1.4 |
| WALBSP-03816 | A37T-S39E-I43V-A47V-T56Y-I80V-N85S-E87D-S99M-T114Q-D127G-F128S-N242D | 1.9 | 1.4 |
| WALBSP-03817 | A37T-S39E-I43V-A47V-T56Y-I80V-N85S-E87D-S99K-T114Q-D127L-F128C-N242D | 1.4 | 0.6 |
| WALBSP-03820 | A37T-S39E-I43V-A47V-T56Y-I80V-N85S-E87D-S99M-T114Q-S126E-D127A-F128S-N242D | 1.2 | 0.9 |

TABLE 7-continued

Crème Brûlée Cleaning Performance of *B. Gibsonii*-clade Subtilisin Variants, Expressed as PI versus Bgi02446 Wild-type

| | | PI versus Bgi02446 Wild-type | |
|---|---|---|---|
| *B. gibsonii*-Subtilisin | Amino Acid Substitutions With Respect to Bgi02446 Wild-type | MGDA detergent | GSM-B detergent |
| WALBSP-03822 | A37T-S39E-I43V-A47V-T56Y-I80V-N85S-E87D-T114Q-D127P-F128E-N242D | 2.5 | 1.5 |
| WALBSP-03829 | A37T-S39E-I43V-A47V-T56Y-I80V-N85S-E87D-S99A-T114Q-S126M-D127S-F128A-N242D | 1.1 | 0.8 |
| WALBSP-03832 | A37T-S39E-I43V-A47V-T56Y-I80V-N85S-E87D-S99H-T114Q-D127G-F128G-N242D | 1.7 | 1.5 |
| WALBSP-03840 | A37T-S39E-I43V-A47V-T56Y-I80V-N85S-E87D-S99T-T114Q-S126V-D127E-F128K-N242D | 1.1 | 0.8 |
| WALBSP-03844 | A37T-S39E-I43V-A47V-T56Y-I80V-N85S-E87D-S99T-T114Q-S126G-D127G-F128T-N242D | 1.1 | 0.8 |
| WALBSP-03845 | A37T-S39E-I43V-A47V-T56Y-I80V-N85S-E87D-S99Q-T114Q-S126T-D127V-F128D-N242D | 1.7 | 1.0 |
| WALBSP-04018 | A37T-S39E-I43V-A47V-T56Y-I80V-N85S-E87D-T114Q-S126T-D127L-F128S-N242D | 1.4 | 1.2 |
| WALBSP-04019 | A37T-S39E-I43V-A47V-T56Y-I80V-N85S-E87D-T114Q-S126T-D127G-F128V-N242D | 1.2 | 1.2 |
| WALBSP-04026 | A37T-S39E-I43V-A47V-T56Y-I80V-N85S-E87D-T114Q-S126R-F128A-N242D | 1.1 | 0.9 |
| WALBSP-04027 | A37T-S39E-I43V-A47V-T56Y-I80V-N85S-E87D- T114Q-S126A-D127S-F128A-N242D | 1.6 | 1.5 |
| WALBSP-04029 | A37T-S39E-I43V-A47V-T56Y-I80V-N85S-E87D-T114Q-D127G-F128L-N242D | 1.3 | 1.2 |
| WALBSP-04034 | A37T-S39E-I43V-A47V-T56Y-I80V-N85S-E87D-T114Q-S126G-D127A-F128G-N242D | 1.3 | 1.4 |
| WALBSP-04035 | A37T-S39E-I43V-A47V-T56Y-I80V-N85S-E87D- T114Q-D127G-F128Q-N242D | 1.8 | 1.6 |
| WALBSP-04037 | A37T-S39E-I43V-A47V-T56Y-I80V-N85S-E87D-T114Q-S126M-D127S-F128A-N242D | 1.3 | 1.2 |
| WALBSP-04038 | A37T-S39E-I43V-A47V-T56Y-I80V-N85S-E87D- T114Q-S126M-D127A-F128W-N242D | 1.5 | 1.5 |
| WALBSP-04039 | A37T-S39E-I43V-A47V-T56Y-I80V-N85S-E87D-T114Q-S126A-D127H-F128V-N242D | 1.2 | 1.0 |
| WALBSP-04042 | A37T-S39E-I43V-A47V-T56Y-I80V-N85S-E87D-T114Q-D127T-F128T-N242D | 1.2 | 1.2 |
| WALBSP-04047 | A37T-S39E-I43V-A47V-T56Y-I80V-N85S-E87D-T114Q-S126A-D127V-F128T-N242D | 1.4 | 1.4 |
| WALBSP-04048 | A37T-S39E-I43V-A47V-T56Y-I80V-N85S-E87D- T114Q-S126A-D127L-F128N-N242D | 1.4 | 1.4 |
| WALBSP-04050 | A37T-S39E-I43V-A47V-T56Y-I80V-N85S-E87D- T114Q-D127Q-F128M-N242D | 1.2 | 1.3 |
| WALBSP-04054 | A37T-S39E-I43V-A47V-T56Y-I80V-N85S-E87D-T114Q-S126G-D127T-F128E-N242D | 1.9 | 2.3 |
| WALBSP-04058 | A37T-S39E-I43V-A47V-T56Y-I80V-N85S-E87D- T114Q-D127Q-F128S-N242D | 1.1 | 1.5 |
| WALBSP-04061 | A37T-S39E-I43V-A47V-T56Y-I80V-N85S-E87D-T114Q-D127N-F128G-N242D | 1.8 | 1.8 |
| WALBSP-04065 | A37T-S39E-I43V-A47V-T56Y-I80V-N85S-E87D-T114Q-D127L-F128N-N242D | 1.2 | 1.2 |
| WALBSP-04067 | A37T-S39E-I43V-A47V-T56Y-I80V-N85S-E87D-T114Q-D127V-F128T-N242D | 1.3 | 1.4 |
| WALBSP-04069 | A37T-S39E-I43V-A47V-T56Y-I80V-N85S-E87D-T114Q-D127V-F128S-N242D | 1.2 | 1.3 |
| WALBSP-04071 | A37T-S39E-I43V-A47V-T56Y-I80V-N85S-E87D-T114Q-S126M-D127V-F128G-N242D | 1.0 | 1.1 |
| WALBSP-04075 | A37T-S39E-I43V-A47V-T56Y-I80V-N85S-E87D-T114Q-S126A-D127G-F128N-N242D | 1.5 | 1.5 |
| WALBSP-04076 | A37T-S39E-I43V-A47V-T56Y-I80V-N85S-E87D-T114Q-S126L-D127F-F128R-N242D | 1.0 | 1.2 |
| WALBSP-04077 | A37T-S39E-I43V-A47V-T56Y-I80V-N85S-E87D-T114Q-S126G-D127V-F128G-N242D | 1.4 | 1.6 |
| WALBSP-04081 | A37T-S39E-I43V-A47V-T56Y-I80V-N85S-E87D-T114Q-S126V-D127M-F128S-N242D | 0.9 | 1.1 |
| WALBSP-04083 | A37T-S39E-I43V-A47V-T56Y-I80V-N85S-E87D-T114Q-S126A-D127W-F128G-N242D | 0.8 | 1.2 |
| WALBSP-04084 | A37T-S39E-I43V-A47V-T56Y-I80V-N85S-E87D-T114Q-S126A-D127S-F128S-N242D | 1.1 | 1.7 |
| WALBSP-04087 | A37T-S39E-I43V-A47V-T56Y-I80V-N85S-E87D-T114Q-S126M-D127S-F128T-N242D | 1.4 | 1.2 |
| WALBSP-04092 | A37T-S39E-I43V-A47V-T56Y-I80V-N85S-E87D-T114Q-D127A-F128V-N242D | 0.9 | 1.4 |

TABLE 7-continued

Crème Brûlée Cleaning Performance of *B. Gibsonii*-clade Subtilisin Variants, Expressed as PI versus Bgi02446 Wild-type

| *B. gibsonii*-Subtilisin | Amino Acid Substitutions With Respect to Bgi02446 Wild-type | PI versus Bgi02446 Wild-type MGDA detergent | PI versus Bgi02446 Wild-type GSM-B detergent |
|---|---|---|---|
| WALBSP-04093 | A37T-S39E-I43V-A47V-T56Y-I80V-N85S-E87D-T114Q-S126Q-D127L-F128H-N242D | 0.8 | 1.2 |
| WALBSP-04113 | A37T-S39E-I43V-A47V-T56Y-I80V-N85S-E87D-S99R-T114Q-S126M-D127P-F128E-N242D | 1.1 | 1.0 |
| WALBSP-04134 | A37T-S39E-I43V-A47V-T56Y-I80V-N85S-E87D-S99R-T114Q-F128E-N242D | 2.7 | 2.2 |
| WALBSP-04137 | A37T-S39E-I43V-A47V-T56Y-I80V-N85S-E87D-S99R-T114Q-S126L-D127H-F128E-N242D | 1.1 | 0.8 |
| WALBSP-04141 | A37T-S39E-I43V-A47V-T56Y-I80V-N85S-E87D-S99R-T114Q-S126M-D127L-F128E-N242D | 1.1 | 0.9 |
| WALBSP-04170 | A37T-S39E-I43V-A47V-T56Y-I80V-N85S-E87D-S99R-T114Q-D127E-F128G-N242D | 1.8 | 1.9 |
| WALBSP-04176 | A37T-S39E-I43V-A47V-T56Y-I80V-N85S-E87D-S99R-T114Q-S126E-D127A-F128S-N242D | 1.5 | 0.8 |
| WALBSP-04177 | A37T-S39E-I43V-A47V-T56Y-I80V-N85S-E87D-S99R-T114Q-S126Q-D127V-F128C-N242D | 1.4 | 0.8 |
| WALBSP-04181 | A37T-S39E-I43V-A47V-T56Y-I80V-N85S-E87D-S99R-T114Q-S126N-D127G-F128G-N242D | 1.3 | 1.2 |
| WALBSP-04197 | A37T-S39E-I43V-A47V-T56Y-I80V-N85S-E87D-S99R-T114Q-S126T-D127E-F128E-N242D | 2.9 | 1.8 |
| WALBSP-04217 | A37T-S39E-I43V-A47V-T56Y-I80V-N85S-E87D-S99R-T114Q-S126D-D127S-F128A-N242D | 1.8 | 0.8 |
| WALBSP-04227 | A37T-S39E-I43V-A47V-T56Y-I80V-N85S-E87D-S99R-T114Q-S126W-D127N-F128D-N242D | 1.3 | 0.5 |
| WALBSP-04251 | A37T-S39E-I43V-A47V-T56Y-I80V-N85S-E87D-S99R-T114Q-S126A-D127E-F128G-N242D | 1.5 | 1.9 |
| WALBSP-04254 | A37T-S39E-I43V-A47V-T56Y-I80V-N85S-E87D-S99R-T114Q-D127A-F128C-N242D | 2.0 | 1.7 |
| WALBSP-04261 | A37T-S39E-I43V-A47V-P54T-T56Y-I80V-N85S-E87D-S99R-T114Q-S126T-D127E-F128A-N242D | 2.4 | 1.5 |
| WALBSP-04286 | A37T-S39E-I43V-A47V-P54T-T56Y-I80V-N85S-E87D-S99R-T114Q-D127I-F128T-N242D | 1.2 | 0.5 |
| WALBSP-04288 | A37T-S39E-I43V-A47V-P54T-T56Y-I80V-N85S-E87D-S99R-T114Q-S126L-D127G-F128E-N242D | 1.6 | 1.0 |
| WALBSP-04297 | A37T-S39E-I43V-A47V-P54T-T56Y-I80V-N85S-E87D-S99R-T114Q-S126V-D127A-F128T-N242D | 2.1 | 1.1 |
| WALBSP-04304 | A37T-S39E-I43V-A47V-P54T-T56Y-I80V-N85S-E87D-S99R-T114Q-S126L-F128H-N242D | 1.6 | 0.8 |
| WALBSP-04309 | A37T-S39E-I43V-A47V-P54T-T56Y-I80V-N85S-E87D-S99R-T114Q-S126Q-D127A-F128D-N242D | 1.3 | 0.6 |
| WALBSP-04310 | A37T-S39E-I43V-A47V-P54T-T56Y-I80V-N85S-E87D-S99R-T114Q-S126L-D127T-F128Q-N242D | 1.4 | 0.8 |
| WALBSP-04317 | A37T-S39E-I43V-A47V-P54T-T56Y-I80V-N85S-E87D-S99R-T114Q-S126L-D127P-F128G-N242D | 1.6 | 0.9 |
| WALBSP-04352 | A37T-S39E-I43V-A47V-P54T-T56Y-I80V-N85S-E87D-S99R-T114Q-S126I-D127E-F128T-N242D | 1.1 | 0.8 |
| WALBSP-04363 | A37T-S39E-I43V-A47V-P54T-T56Y-I80V-N85S-E87D-S99R-T114Q-S126G-D127E-F128D-N242D | 2.5 | 1.5 |
| WALBSP-04386 | A37T-S39E-I43V-A47V-P54T-T56Y-I80V-N85S-E87D-S99R-T114Q-S126T-F128E-N242D | 1.4 | 1.1 |
| WALBSP-04390 | A37T-S39E-I43V-A47V-P54T-T56Y-I80V-N85S-E87D-S99R-T114Q-S126L-F128A-N242D | 1.6 | 0.4 |
| WALBSP-04416 | A37T-S39E-I43V-A47V-P54T-T56Y-I80V-N85S-E87D-S99R-T114Q-S126G-D127P-F128C-N242D | 1.6 | 1.4 |
| WALBSP-04418 | A37T-S39E-I43V-A47V-P54T-T56Y-I80V-N85S-E87D-S99R-T114Q-D127S-F128S-N242D | 0.8 | 1.3 |
| WALBSP-04427 | A37T-S39E-I43V-A47V-P54T-T56Y-I80V-N85S-E87D-S99R-T114Q-S126D-D127G-F128A-N242D | 1.2 | 0.9 |
| WALBSP-04457 | A37T-S39E-I43V-A47V-P54T-T56Y-I80V-N85S-E87D-S99R-T114Q-S126A-D127W-F128E-N242D | 1.5 | 1.2 |
| WALBSP-04498 | A37T-S39E-I43V-A47V-P54T-T56Y-I80V-N85S-E87D-S99R-T114Q-S126A-D127N-F128C-N242D | 1.4 | 0.8 |
| WALBSP-04501 | A37T-S39E-I43V-A47V-P54T-T56Y-I80V-N85S-E87D-S99R-T114Q-S126Y-F128L-N242D | 1.1 | 1.6 |
| WALBSP-04507 | A37T-S39E-I43V-A47V-P54T-T56Y-I80V-N85S-E87D-S99R-T114Q-S126A-D127S-F128S-N242D | 0.4 | 1.2 |
| WALBSP-04508 | A37T-S39E-I43V-A47V-P54T-T56Y-I80V-N85S-E87D-S99R-T114Q-D127I-F128S-N242D | ND | 1.3 |
| WALBSP-04516 | A37T-S39E-I43V-A47V-P54T-T56Y-I80V-N85S-E87D-S99R-T114Q-D127G-F128P-N242D | ND | 2.7 |

TABLE 7-continued

| Crème Brûlée Cleaning Performance of *B. Gibsonii*-clade Subtilisin Variants, Expressed as PI versus Bgi02446 Wild-type | | | |
|---|---|---|---|
| | | PI versus Bgi02446 Wild-type | |
| *B. gibsonii*-Subtilisin | Amino Acid Substitutions With Respect to Bgi02446 Wild-type | MGDA detergent | GSM-B detergent |
| WALBSP-04558 | A37T-S39E-I43V-A47V-P54T-T56Y-I80V-N85S-E87D-S99R-T114Q-D127G-F128E-N242D | ND | 2.7 |
| WALBSP-04566 | A37T-S39E-I43V-A47V-P54T-T56Y-I80V-N85S-E87D-S99R-T114Q-D127T-F128A-N242D | ND | 1.1 |
| WALBSP-04596 | A37T-S39E-I43V-A47V-P54T-T56Y-I80V-N85S-E87D-S99R-T114Q-S126T-D127Y-F128D-N242D | ND | 1.8 |
| WALBSP-04618 | A37T-S39E-I43V-A47V-P54T-T56Y-I80V-N85S-E87D-S99R-T114Q-S126M-D127A-F128D-N242D | ND | 1.3 |
| WALBSP-04621 | A37T-S39E-I43V-A47V-P54T-T56Y-I80V-N85S-E87D-S99R-T114Q-D127N-F128D-N242D | ND | 1.1 |
| WALBSP-04627 | A37T-S39E-I43V-A47V-P54T-T56Y-I80V-N85S-E87D-S99R-T114Q-S126V-D127E-F128V-N242D | ND | 1.7 |
| WALBSP-04654 | A37T-S39E-I43V-A47V-P54T-T56Y-I80V-N85S-E87D-S99R-T114Q-S126N-D127G-F128L-N242D | 0.7 | 1.1 |
| WALBSP-04678 | A37T-S39E-I43V-A47V-P54T-T56Y-I80V-N85S-E87D-S99R-T114Q-S126T-D127E-F128L-N242D | 1.1 | 1.4 |
| WALBSP-04704 | A37T-S39E-I43V-A47V-P54T-T56Y-I80V-N85S-E87D-S99R-T114Q-S126A-F128G-N242D | 1.9 | 2.4 |
| WALBSP-04708 | A37T-S39E-I43V-A47V-P54T-T56Y-I80V-N85S-E87D-S99R-T114Q-S126T-D127G-F128G-N242D | 0.6 | 1.2 |
| WALBSP-04715 | A37T-S39E-I43V-A47V-P54T-T56Y-I80V-N85S-E87D-S99R-T114Q-F128E-N242D | 2.2 | 2.4 |
| WALBSP-04802 | A37T-S39E-I43V-A47V-P54T-T56Y-I80V-N85S-E87D-S99R-T114Q-S126Y-D127E-F128G-N242D | 1.1 | 1.6 |
| WALBSP-04806 | A37T-S39E-I43V-A47V-P54T-T56Y-I80V-N85S-E87D-S99R-T114Q-S126A-F128Q-N242D | 1.0 | 1.5 |
| WALBSP-04815 | A37T-S39E-I43V-A47V-P54T-T56Y-I80V-N85S-E87D-S99R-T114Q-S126A-D127E-F128G-N242D | 1.5 | 2.9 |
| WALBSP-04899 | A37T-S39E-I43V-A47V-P54T-T56Y-I80V-N85S-E87D-S99R-T114Q-S126T-F128A-N242D | 1.3 | 1.0 |
| WALBSP-04901 | A37T-S39E-I43V-A47V-P54T-T56Y-I80V-N85S-E87D-S99E-T114Q-S126T-F128A-N242D | 2.0 | 1.1 |
| WALBSP-04902 | A37T-S39E-I43V-A47V-T56Y-I80V-N85S-E87D-S99E-T114Q-D127E-F128G-N242D | 2.3 | 1.3 |

The performance tests reported on Table 8 were carried out at 40° C., using pre-rinsed or unrinsed PAS-38 swatches, and the enzyme stability was measured as described on Example 2, on Tris buffer containing 1 mM EDTA, with samples incubated at 52° C. for 5 minutes.

TABLE 8

| ADW cleaning performance and stability (reported as performance indices (PI)values) for various *B gibsonii*-clade variants compared to Bgi02446 parent. | | | | | | |
|---|---|---|---|---|---|---|
| | | Cleaning performance on PA-S-38 | | | | Stability |
| *B gibsonii*-variants | Substitutions with respect to Bgi02446 | GSM-B wildtype | GSM-B Rinsed | MGDA Unrinsed | MGDA Rinsed | TRIS-EDTA Unrinsed |
| WALBSP-03320 | I043V-A047V-T056Y-T114Q | 1.0 | 1.1 | 1.0 | 1.1 | 0.9 |
| WALBSP-03485 | S039E-I080V-S099R-T114Q-N242D | 1.3 | 3.1 | 1.4 | 3.3 | 2.8 |
| WALBSP-03551 | S039E-I043V-E087D-S099R-T114Q | 1.1 | 1.4 | 1.0 | 1.3 | 2.6 |
| WALBSP-03554 | S039E-I043V-A047V-E087D-S099R | 1.1 | 1.4 | 1.1 | 1.3 | 2.6 |
| WALBSP-03589 | S039E-A047V-N085S-S099R-T114Q-N242D | 1.0 | 1.3 | 0.9 | 1.2 | 3.2 |
| WALBSP-03601 | S039E-I043V-T056Y-E087D-S099R-T114Q | 1.0 | 1.3 | 1.0 | 1.3 | 2.5 |
| WALBSP-03684 | S039E-I043V-T056Y-E087D-S099R-N242D | 1.1 | 1.2 | 1.2 | 1.2 | 3.1 |
| WALBSP-03472 | S039E-I043V-A047V-S099R-T114Q-N242D | 1.2 | 2.9 | 1.3 | 3.0 | 3.0 |

TABLE 8-continued

ADW cleaning performance and stability (reported as performance indices (PI)values) for various *B gibsonii*-clade variants compared to Bgi02446 parent.

| | | Cleaning performance on PA-S-38 | | | | Stability |
|---|---|---|---|---|---|---|
| *B gibsonii*-variants | Substitutions with respect to Bgi02446 | GSM-B wildtype | GSM-B Rinsed | MGDA Unrinsed | MGDA Rinsed | TRIS-EDTA Unrinsed |
| WALBSP-03666 | A037T-S039E-I043V-S099R-T114Q-N242D | 1.1 | 1.2 | 1.2 | 1.1 | 3.0 |
| WALBSP-03633 | S039E-A047V-T056Y-N085S-E087D-S099R-T114Q | 1.1 | 1.4 | 1.1 | 1.3 | 2.5 |
| WALBSP-03541 | S039E-A047V-T056Y-I080V-N085S-S099R-T114Q | 1.0 | 1.4 | 0.9 | 1.3 | 2.4 |
| WALBSP-03596 | S039E-I043V-N085S-E087D-S099R-T114Q-N242D | 1.0 | 1.2 | 1.2 | 1.2 | 3 |
| WALBSP-03659 | A037T-S039E-A047V-I080V-N085S-S099R-N242D | 1.0 | 1.4 | 1.1 | 1.3 | 2.7 |
| WALBSP-03681 | A037T-S039E-I043V-N085S-E087D-S099R-T114Q | 0.9 | 1.2 | 1.0 | 1.2 | 2.5 |
| WALBSP-03625 | S039E-I043V-T056Y-I080V-N085S-S099R-T114Q-N242D | 1.0 | 1.3 | 1.0 | 1.2 | 2.7 |
| WALBSP-03695 | A037T-S039E-I043V-I080V-N085S-E087D-S099R-T114Q | 0.9 | 1.3 | 1.0 | 1.2 | 2.3 |
| WALBSP-03622 | A037T-S039E-I043V-A047V-N085S-E087D-S099R-T114Q-N242D | 1.0 | 1.2 | 1.0 | 1.2 | 3.1 |

The performance tests reported on Table 9 were carried out at 40° C., using DM10 melamine tiles as described on Example 2, using MGDA and GSM-B detergents.

TABLE 9

ADW cleaning Derformance indices (PI values) on Crème Brûlée (DM10 soil) for various *B gibsonii*-clade variants compared to Bgi02446 parent.

| *B gibsonii*-variant | Substitutions with respect to Bgi02446 wildtype | GSM-B detergent | MGDA detergent |
|---|---|---|---|
| WALBSP-04914 | A37T-S39E-I43V-A47V-T56Y-I80V-N85S-E87D-S99R-T114Q-M122L-S126A-D127E-F128G-N242D | 1.6 | 1.4 |
| WALBSP-04910 | A37T-S39E-I43V-A47V-T56Y-I80V-N85S-E87D-S99R-T114Q-S126A-D127E-F128G-M211L-N242D | 2.2 | 2.0 |
| WALBSP-04911 | A37T-S39E-I43V-A47V-T56Y-I80V-N85S-E87D-S99R-T114Q-M117I-S126A-D127E-F128G-M211L-N242D | 1.9 | 1.5 |
| WALBSP-04912 | A37T-S39E-I43V-A47V-T56Y-I80V-N85S-E87D-S99R-T114Q-S126A-D127E-F128G-M211L-M122L-N242D | 2.0 | 1.9 |
| WALBSP-04913 | A37T-S39E-I43V-A47V-T56Y-I80V-N85S-E87D-S99R-T114Q-M117I-S126A-D127E-F128G-M211L-M122L-N242D | 2.2 | 1.7 |
| WALBSP-04915 | A37T-S39E-I43V-A47V-P54T-T56Y-I80V-N85S-E87D-S99R-T114Q-M122L-S126A-D127E-F128G-N242D | 1.8 | 1.6 |
| WALBSP-04916 | A37T-S39E-I43V-A47V-P54T-T56Y-I80V-N85S-E87D-S99R-T114Q-S126A-D127E-F128G-M211L-N242D | 2.5 | 2.1 |
| WALBSP-04917 | A37T-S39E-I43V-A47V-P54T-T56Y-I80V-N85S-E87D-S99R-T114Q-M117I-M122L-S126A-D127E-F128G-N242D | 1.6 | 1.5 |
| WALBSP-04918 | A37T-S39E-I43V-A47V-P54T-T56Y-I80V-N85S-E87D-S99R-T114Q-M122L-S126A-D127E-F128G-M211L-N242D | 1.9 | 1.9 |
| WALBSP-04919 | A37T-S39E-I43V-A47V-P54T-T56Y-I80V-N85S-E87D-S99R-T114Q-M117I-M122L-S126A-D127E-F128G-M211L-N242D | 2.0 | 1.9 |

The performance tests reported on Table 10 were carried out using unrinsed PAS-38 swatches at 40° C. with GSM-B detergent, and at 50° C. with ADW formulas A, B and C, or using DM10 stain and GSM-B detergent as described on Example 2. The stability reported on Table 10 was measured on Tris buffer containing 5 mM EDTA, with samples incubated at 56° C. for 5 minutes as described on Example 2.

TABLE 10

ADW Cleaning Performance on PAS38 and DM10 stains of *B. gibsonii*-clade Subtilisin Variants (expressed as PI compared to Bgi02446 parent) and Stability in Tris-EDTA reported as percent remaining activity.

| *B gibsonii*-variants | Substitutions with respect to Bgi02446 wildtype | Stability TRIS-EDTA | PAS-38 stain Cleaning in ADW formula A | B | C | GSM-B | DM10 cleaning GSM-B |
|---|---|---|---|---|---|---|---|
| Bgi02446-WT | none | <1 | 1.0 | 1.0 | 1.0 | 1.1 | 1.0 |
| WALBSP-07063 | T056Y-S099R-S126A-D127E-F128G | 9 | 1.7 | 2.2 | 2.6 | 1.6 | 0.9 |
| WALBSP-07078 | S039E-I080V-S099R-S126A-D127E-F128G-M211L | 21 | 2.2 | 3.5 | ND | 2.8 | 2.7 |
| WALBSP-07137 | S039E-P054T-S099R-S126A-D127E-F128G-M211L | 28 | 2.3 | 2.9 | ND | 3.0 | 3.5 |
| WALBSP-07117 | S039E-I043V-S099R-S126A-D127E-F128G-M211L | 28 | 2.3 | 3.0 | 3.7 | 4.0 | 3.2 |
| WALBSP-07119 | S039E-N042R-S099R-S126A-D127E-F128G | 28 | 2.3 | 3.1 | 3.9 | 3.7 | 1.6 |
| WALBSP-07052 | S039E-I080V-S099R-S126A-D127E-F128G | 29 | 2.1 | 2.5 | 2.8 | 1.4 | 2.1 |
| WALBSP-07097 | S039E-S099R-S126A-D127E-F128G-M211L | 29 | 2.4 | 2.6 | ND | 3.2 | 3.1 |
| WALBSP-07088 | S039E-N085S-S099R-S126A-D127E-F128G-M211L | 30 | 2.3 | 3.3 | 3.6 | 3.1 | 2.4 |
| WALBSP-07147 | S039E-T056Y-S099R-S126A-D127E-F128G-M211L | 31 | 2.0 | 3.5 | 3.8 | 2.2 | 7.9 |
| WALBSP-07127 | S039E-A047V-S099R-S126A-D127E-F128G-M211L | 31 | 2.2 | 2.6 | 3.9 | 3.0 | 2.4 |
| WALBSP-07149 | S039E-S099R-S126A-D127E-F128G-Y203W | 32 | 2.0 | 2.6 | ND | 2.4 | 5.7 |
| WALBSP-07107 | A037T-S039E-S099R-S126A-D127E-F128G-M211L | 32 | 2.3 | 3.3 | ND | 3.6 | 2.8 |
| WALBSP-07129 | S039E-S099R-S126A-D127E-F128G-V199I | 34 | 2.3 | 3.1 | 4.3 | 2.9 | 2.7 |
| WALBSP-07058 | A037T-S039E-I043V-A047V-P054T-T056Y-I080V-N085S-E087D-S099R-T114Q-S126A-D127E-F128G | 35 | 2.0 | 2.2 | 2.8 | 1.3 | 1.8 |
| WALBSP-07050 | S039E-I043V-A047V-P054T-T056Y-I080V-N085S-E087D-S099R-S126A-D127E-F128G-N242D | 35 | 2.0 | 2.4 | 2.9 | 1.3 | 2.5 |
| WALBSP-07040 | A037T-S039E-I043V-A047V-T056Y-I080V-N085S-E087D-S099R-T114Q-S126A-D127E-F128G | 36 | 2.0 | 2.7 | 3.1 | 1.3 | 1.9 |
| WALBSP-07014 | A037T-S039E-I043V-A047V-P054T-T056Y-I080V-N085S-E087D-S099R-S126A-D127E-F128G | 37 | 3.6 | 3.4 | 3.9 | 1.3 | 1.5 |
| WALBSP-07012 | S039E-I043V-S099R-S126A-D127E-F128G | 38 | 2.2 | 2.1 | 2.7 | 1.5 | 2.2 |
| WALBSP-07080 | S039E-S099R-S126A-D127E-F128G-N253D | 38 | 1.7 | 1.9 | ND | 0.2 | 0.9 |
| WALBSP-07109 | T009E-S039E-S099R-S126A-D127E-F128G | 38 | 2.1 | 3.0 | 3.4 | 2.4 | 5.5 |
| WALBSP-07090 | S039E-S099R-S126A-D127E-F128G-S255W | 38 | 2.4 | 2.9 | 3.8 | 3.3 | 1.6 |
| WALBSP-07041 | A037T-S039E-I043V-A047V-P054T-T056Y-I080V-N085S-S099R-S126A-D127E-F128G-N242D | 38 | 2.0 | 2.5 | 2.9 | 1.2 | 2.6 |
| WALBSP-07001 | A037T-S039E-I043V-P054T-T056Y-I080V-N085S-E087D-S099R-S126A-D127E-F128G-N242D | 38 | 1.9 | 2.4 | 3.0 | 1.3 | 2.6 |

TABLE 10-continued

ADW Cleaning Performance on PAS38 and DM10 stains of *B. gibsonii*-clade Subtilisin Variants (expressed as PI compared to Bgi02446 parent) and Stability in Tris-EDTA reported as percent remaining activity.

| *B gibsonii*-variants | Substitutions with respect to Bgi02446 wildtype | Stability TRIS-EDTA | PAS-38 stain Cleaning in ADW formula A | B | C | GSM-B | DM10 cleaning GSM-B |
|---|---|---|---|---|---|---|---|
| WALBSP-07024 | S039E-I043V-A047V-T056Y-I080V-N085S-E087D-S099R-S126A-D127E-F128G-N242D | 39 | 2.1 | 2.3 | 2.5 | 1.3 | 2.2 |
| WALBSP-07068 | S039E-I043V-A047V-T056Y-I080V-N085S-E087D-S099R-T114Q-S126A-D127E-F128G-N242D | 39 | 1.8 | 2.3 | 2.8 | 1.4 | 2.3 |
| WALBSP-07042 | S039E-T056Y-S099R-S126A-D127E-F128G | 39 | 2.1 | 2.3 | 2.6 | 1.4 | 1.6 |
| WALBSP-07065 | A037T-S039E-I043V-A047V-T056Y-I080V-N085S-E087D-S099R-S126A-D127E-F128G | 39 | 2.1 | 1.9 | 2.7 | 1.5 | 1.7 |
| WALBSP-07027 | A037T-S039E-I043V-P054T-T056Y-I080V-N085S-E087D-S099R-T114Q-S126A-D127E-F128G-N242D | 39 | 1.9 | 2.5 | 3.0 | 1.4 | 2.3 |
| WALBSP-07019 | A037T-S039E-I043V-T056Y-I080V-N085S-E087D-S099R-T114Q-S126A-D127E-F128G-N242D | 39 | 2.1 | 2.4 | 2.9 | 1.2 | 2.8 |
| WALBSP-07029 | A037T-S039E-I043V-A047V-I080V-N085S-E087D-S099R-T114Q-S126A-D127E-F128G-N242D | 39 | 1.9 | 2.5 | 3.0 | 1.3 | 2.7 |
| WALBSP-07011 | A037T-S039E-I043V-A047V-P054T-I080V-N085S-E087D-S099R-S126A-D127E-F128G-N242D | 39 | 2.0 | 2.2 | 2.8 | 1.2 | 2.5 |
| WALBSP-07055 | A037T-S039E-I043V-A047V-T056Y-I080V-N085S-E087D-S099R-S126A-D127E-N242D | 39 | 2.0 | 2.1 | 2.6 | 1.3 | 1.1 |
| WALBSP-07054 | A037T-S039E-I043V-T056Y-I080V-N085S-E087D-S099R-S126A-D127E-F128G-N242D | 39 | 2.0 | 2.1 | 2.7 | 1.3 | 2.4 |
| WALBSP-07030 | A037T-S039E-I043V-A047V-T056Y-I080V-N085S-E087D-S099R-T114Q-S126A-D127E-N242D | 39 | 2.0 | 2.4 | 3.0 | 1.1 | 1.1 |
| WALBSP-07062 | S039E-N085S-S099R-S126A-D127E-F128G | 40 | 2.0 | 2.5 | 2.7 | 1.6 | 2.0 |
| WALBSP-07047 | A037T-S039E-I043V-A047V-P054T-I080V-N085S-E087D-S099R-T114Q-S126A-D127E-F128G-N242D | 40 | 1.9 | 2.5 | 2.8 | 1.3 | 2.5 |
| WALBSP-06998 | A037T-S039E-I043V-A047V-P054T-T056Y-I080V-N085S-S099R-T114Q-S126A-D127E-F128G-N242D | 40 | 1.9 | 2.4 | 2.7 | 1.4 | 2.6 |
| WALBSP-07048 | A037T-S039E-I043V-A047V-P054T-T056Y-I080V-N085S-E087D-S099R-T114Q-S126A-D127E-N242D | 40 | 2.0 | 2.3 | 3.0 | 1.3 | 1.0 |
| WALBSP-07051 | A037T-S039E-I043V-A047V-P054T-T056Y-I080V-N085S-E087D-S126A-D127E-F128G-N242D | 40 | 0.7 | 0.7 | 0.8 | 0.7 | 3.6 |
| WALBSP-07045 | A037T-S039E-I043V-A047V-T056Y-I080V-N085S-E087D-S099R-S126A-F128G-N242D | 40 | 2.1 | 2.1 | 2.6 | 1.2 | 2.4 |
| WALBSP-07049 | A037T-S039E-I043V-A047V-T056Y-I080V-E087D-S099R-T114Q-S126A-D127E-F128G-N242D | 41 | 2.0 | 2.6 | 2.9 | 1.3 | 2.4 |
| WALBSP-07003 | S039E-S099R-T114Q-S126A-D127E-F128G | 41 | 2.1 | 2.3 | 2.8 | 1.6 | 2.0 |
| WALBSP-07004 | A037T-S039E-I043V-A047V-P054T-T056Y-I080V-N085S-E087D-S099R-S126A-D127E-N242D | 41 | 1.9 | 2.2 | 2.6 | 1.3 | 1.0 |

TABLE 10-continued

ADW Cleaning Performance on PAS38 and DM10 stains of *B. gibsonii*-clade Subtilisin Variants (expressed as PI compared to Bgi02446 parent) and Stability in Tris-EDTA reported as percent remaining activity.

| *B gibsonii*- variants | Substitutions with respect to Bgi02446 wildtype | Stability TRIS- EDTA | PAS-38 stain Cleaning in ADW formula A | B | C | GSM-B | DM10 cleaning GSM-B |
|---|---|---|---|---|---|---|---|
| WALBSP-07000 | A037T-S039E-I043V-A047V-T056Y-I080V-N085S-E087D-S099R-S126A-D127E-F128G-N242D | 41 | 1.9 | 2.2 | 2.7 | 1.3 | 2.3 |
| WALBSP-07028 | A037T-S039E-I043V-A047V-P054T-T056Y-I080V-N085S-E087D-S099R-T114Q-D127E-F128G-N242D | 41 | 2.1 | 2.2 | 2.7 | 1.1 | 2.4 |
| WALBSP-07059 | A037T-S039E-I043V-A047V-T056Y-I080V-N085S-S099R-T114Q-S126A-D127E-F128G-N242D | 41 | 2.0 | 2.3 | 3.0 | 1.3 | 2.6 |
| WALBSP-07022 | S039E-A047V-S099R-S126A-D127E-F128G | 41 | 2.1 | 2.5 | 2.5 | 1.4 | 2.4 |
| WALBSP-07015 | A037T-S039E-I043V-A047V-T056Y-I080V-N085S-S099R-S126A-D127E-F128G-N242D | 41 | 2.0 | 2.0 | 2.7 | 1.2 | 2.3 |
| WALBSP-07033 | A037T-S039E-I043V-A047V-T056Y-S099R-T114Q-S126A-D127E-F128G | 41 | 2.1 | 2.4 | 2.6 | 1.4 | 1.8 |
| WALBSP-07031 | A037T-S039E-I043V-A047V-P054T-T056Y-I080V-E087D-S099R-S126A-D127E-F128G-N242D | 41 | 2.0 | 2.3 | 2.8 | 1.2 | 2.7 |
| WALBSP-07032 | S039E-P054T-S099R-S126A-D127E-F128G | 41 | 3.6 | 4.1 | 4.6 | 1.3 | 2.4 |
| WALBSP-04815 | A37T-S39E-I43V-A47V-P54T-T56Y-I80V-N85S-E87D-S99R-T114Q-S126A-D127E-F128G-N242D | 36 | 2.0 | 2.3 | 2.6 | 1.2 | 2.4 |
| WALBSP-07064 | A037T-S039E-I043V-A047V-I080V-N085S-E087D-S099R-S126A-D127E-F128G-N242D | 42 | 2.0 | 1.9 | 2.4 | 1.3 | 2.3 |
| WALBSP-07005 | A037T-S039E-I043V-A047V-T056Y-I080V-E087D-S099R-S126A-D127E-F128G-N242D | 42 | 1.9 | 2.0 | 2.5 | 1.4 | 2.2 |
| WALBSP-04170 | A037T-S039E-I043V-A047V-T056Y-I080V-N085S-E087D-S099R-T114Q-D127E-F128G-N242D | 42 | 2.1 | 2.6 | 2.9 | 1.3 | 2.1 |
| WALBSP-07061 | A037T-S039E-I043V-A047V-P054T-T056Y-I080V-N0855-E087D-S099R-D127E-F128G-N242D | 42 | 2.0 | 2.1 | 2.9 | 1.3 | 2.2 |
| WALBSP-07072 | S039E-E087D-S099R-S126A-D127E-F128G | 42 | 2.0 | 1.9 | 2.8 | 1.6 | 1.5 |
| WALBSP-07035 | A037T-S039E-I043V-A047V-T056Y-I080V-N085S-E087D-S099R-D127E-F128G-N242D | 42 | 2.1 | 2.1 | 2.7 | 1.3 | 2.7 |
| WALBSP-04704 | A037T-S039E-I043V-A047V-P054T-T056Y-I080V-N0855-E087D-S099R-T114Q-S126A-F128G-N242D | 43 | 1.9 | 2.2 | 2.8 | 1.4 | 2.5 |
| WALBSP-07002 | A037T-S039E-S099R-S126A-D127E-F128G | 43 | 3.8 | 4.8 | 5.5 | 1.7 | 2.4 |
| WALBSP-07067 | A037T-S039E-I043V-A047V-P054T-T056Y-I080V-E087D-S099R-T114Q-S126A-D127E-F128G-N242D | 43 | 1.8 | 2.5 | 2.9 | 1.3 | 2.2 |
| WALBSP-07018 | A037T-S039E-I043V-A047V-P054T-T056Y-I080V-N085S-E087D-S099R-S126A-D127E-F128G-N242D | 43 | 1.9 | 2.2 | 2.8 | 1.2 | 2.5 |
| WALBSP-07020 | A037T-S039E-I043V-A047V-T056Y-I080V-N085S-E087D-S099R-T114Q-S126A-F128G-N242D | 43 | 2.0 | 2.7 | 3.1 | 1.1 | 2.4 |
| WALBSP-07043 | A037T-S039E-I043V-A047V-T056Y-S099R-S126A-D127E-F128G | 44 | 2.0 | 2.3 | 2.7 | 1.4 | 1.9 |

TABLE 10-continued

ADW Cleaning Performance on PAS38 and DM10 stains of *B. gibsonii*-clade Subtilisin Variants (expressed as PI compared to Bgi02446 parent) and Stability in Tris-EDTA reported as percent remaining activity.

| *B gibsonii*-variants | Substitutions with respect to Bgi02446 wildtype | Stability TRIS-EDTA | PAS-38 stain Cleaning in ADW formula A | B | C | GSM-B | DM10 cleaning GSM-B |
|---|---|---|---|---|---|---|---|
| WALBSP-07023 | A037T-S039E-I043V-A047V-P054T-T056Y-S099R-T114Q-S126A-D127E-F128G | 44 | 2.1 | 2.4 | 2.7 | 1.3 | 1.9 |
| WALBSP-07070 | A037T-S039E-A047V-P054T-T056Y-I080V-N085S-E087D-S099R-S126A-D127E-F128G-N242D | 44 | 2.0 | 2.1 | 2.9 | 1.4 | 2.1 |
| WALBSP-07071 | A037T-S039E-I043V-A047V-P054T-T056Y-I080V-N085S-E087D-S099R-S126A-F128G-N242D | 44 | 1.9 | 2.2 | 3.0 | 1.3 | 1.8 |
| WALBSP-07008 | A037T-S039E-I043V-A047V-P054T-T056Y-I080V-N085S-E087D-T114Q-S126A-D127E-F128G-N242D | 44 | 0.7 | 0.7 | 0.8 | 1.0 | 3.7 |
| WALBSP-07025 | A037T-S039E-I043V-A047V-T056Y-I080V-N085S-E087D-S126A-D127E-F128G-N242D | 45 | 0.8 | 0.5 | 0.7 | 1.0 | 3.5 |
| WALBSP-07009 | A037T-S039E-A047V-T056Y-I080V-N085S-E087D-S099R-T114Q-S126A-D127E-F128G-N242D | 45 | 2.1 | 2.6 | 3.2 | 1.3 | 2.7 |
| WALBSP-07075 | S039E-S099R-S126A-D127E-F128G | 45 | 1.9 | 2.3 | 2.8 | 1.6 | 2.1 |
| WALBSP-07017 | A037T-S039E-A047V-P054T-T056Y-I080V-N085S-E087D-S099R-T114Q-S126A-D127E-F128G-N242D | 45 | 2.0 | 2.4 | 2.8 | 1.4 | 2.8 |
| WALBSP-07069 | A037T-S039E-I043V-A047V-T056Y-I080V-N085S-E087D-T114Q-S126A-D127E-F128G-N242D | 46 | 0.8 | 0.3 | 1.0 | 1.0 | 3.0 |
| WALBSP-07044 | A037T-S039E-A047V-T056Y-I080V-N085S-E087D-S099R-S126A-D127E-F128G-N242D | 46 | 2.1 | 2.1 | 2.7 | 1.3 | 2.7 |
| WALBSP-07100 | S039E-S099R-S126A-D127E-F128G-Q256E | 47 | 2.3 | 3.0 | 3.8 | 2.0 | 6.7 |
| WALBSP-07013 | S039E-S099R-S126A-D127E-F128G-N242D | 47 | 2.1 | 2.2 | 2.6 | 1.3 | 2.6 |
| WALBSP-07139 | S039E-S099R-S126A-D127E-F128G-Q200L | 48 | 2.2 | 2.8 | 3.7 | 2.9 | 2.2 |
| WALBSP-07077 | A037T-S039E-I043V-A047V-P054T-T056Y-S099R-T114Q-S126A-D127E-F128G-N242D | 51 | 2.2 | 2.8 | 3.6 | 1.6 | 5.4 |
| WALBSP-07087 | A037T-S039E-I043V-A047V-P054T-T056Y-S099R-S126A-D127E-F128G-N242D | 51 | 2.1 | 2.8 | 3.6 | 1.9 | 4.6 |
| WALBSP-07138 | S039E-N074D-I080V-S099R-S126A-D127E-F128G | 53 | 2.3 | 2.8 | 3.8 | 2.1 | 3.7 |
| WALBSP-07021 | A037T-S039E-I043V-A047V-P054T-T056Y-N085S-E087D-S099R-S126A-D127E-F128G-N242D | 54 | 1.9 | 2.4 | 2.9 | 1.3 | 2.7 |
| WALBSP-07039 | A037T-S039E-I043V-A047V-T056Y-N085S-E087D-S099R-T114Q-S126A-D127E-F128G-N242D | 54 | 2.0 | 2.5 | 3.0 | 1.3 | 2.9 |
| WALBSP-07053 | A037T-S039E-I043V-A047V | 54 | 0.8 | 0.8 | 0.7 | 1.0 | 1.7 |
| WALBSP-07073 | A037T-S039E-I043V-A047V-N242D | 54 | 0.7 | 0.6 | 0.9 | 1.3 | 1.9 |
| WALBSP-07118 | S039E-P054T-N074D-S099R-S126A-D127E-F128G | 55 | 2.3 | 2.8 | 4.2 | 2.3 | 3.9 |
| WALBSP-07108 | S039E-A047V-N074D-S099R-S126A-D127E-F128G | 55 | 2.3 | 2.7 | 3.3 | 2.8 | 3.7 |
| WALBSP-07057 | A037T-S039E-I043V-A047V-P054T-T056Y-N085S-E087D-S099R-T114Q-S126A-D127E-F128G-N242D | 55 | 2.0 | 2.3 | 2.7 | 1.3 | 2.6 |

TABLE 10-continued

ADW Cleaning Performance on PAS38 and DM10 stains of *B. gibsonii*-clade Subtilisin Variants (expressed as PI compared to Bgi02446 parent) and Stability in Tris-EDTA reported as percent remaining activity.

| *B gibsonii*-variants | Substitutions with respect to Bgi02446 wildtype | Stability TRIS-EDTA | PAS-38 stain Cleaning in ADW formula A | B | C | GSM-B | DM10 cleaning GSM-B |
|---|---|---|---|---|---|---|---|
| WALBSP-07089 | S039E-N074D-S099R-T114Q-S126A-D127E-F128G | 55 | 2.5 | 2.8 | 3.8 | 2.5 | 4.2 |
| WALBSP-07148 | S039E-N074D-N085S-S099R-S126A-D127E-F128G | 56 | 2.3 | 3.0 | 3.4 | 1.8 | 10.6 |
| WALBSP-07074 | A037T-S039E-I043V-A047V-T056Y-N085S-E087D-S099R-S126A-D127E-F128G-N242D | 57 | 1.8 | 2.1 | 2.5 | 1.4 | 2.1 |
| WALBSP-07079 | S039E-N074D-E087D-S099R-S126A-D127E-F128G | 57 | 2.3 | 3.4 | ND | 2.2 | 3.4 |
| WALBSP-07098 | S039E-I043V-N074D-S099R-S126A-D127E-F128G | 57 | ND | 2.7 | 3.5 | 2.5 | 3.0 |
| WALBSP-07128 | S039E-T056Y-N074D-S099R-S126A-D127E-F128G | 58 | 2.2 | 3.0 | 3.6 | 2.5 | 3.8 |
| WALBSP-07099 | S039E-N074D-S099R-S126A-D127E-F128G-N242D | 77 | 2.2 | 3.0 | 3.8 | 2.0 | 6.1 |
| WALBSP-04134 | A037T-S039E-I043V-A047V-T056Y-I080V-N085S-E087D-S099R-T114Q-F128E-N242D | 36 | 2.3 | 3.5 | 3.5 | 1.7 | 1.6 |
| WALBSP-04363 | A037T-S039E-I043V-A047V-P054T-T056Y-I080V-N085S-E087D-S099R-T114Q-S126G-D127E-F128D-N242D | 41 | 2.3 | 2.3 | 2.3 | 2.0 | 2.7 |
| WALBSP-04386 | A037T-S039E-I043V-A047V-P054T-T056Y-I080V-N085S-E087D-S099R-T114Q-S126T-F128E-N242D | 39 | 2.2 | 2.7 | 2.8 | 3.4 | 1.4 |
| WALBSP-04715 | A037T-S039E-I043V-A047V-P054T-T056Y-I080V-N085S-E087D-S099R-T114Q-F128E-N242D | 42 | 2.4 | 3.0 | 3.4 | 3.5 | 3.5 |

The performance tests reported on Table 11 were carried out using unrinsed PAS-38 swatches or DM10 tiles, both at 40° C. with GSM-B detergent, as described on Example 2. The stability reported on Table 11 was measured on Tris buffer containing 1 mM EDTA, with samples incubated at 54° C. for 5 minutes, as described on Example 2 and results are reported as percent remaining activity.

TABLE 11

ADW Cleaning Performance of *B. gibsonii*-clade Subtilisin Variants measured on PAS-38 and DM10 stains using GSM-B detergent, expressed as PI compared to Bgi02446 parent, and stability in Tris-EDTA reported as percent remaining activity.

| *B gibsonii*-variants | Substitutions with respect to Bgi02446 wildtype | TRIS-EDTA | PAS-38 GSM-B | DM10 GSM-B |
|---|---|---|---|---|
| Bgi02446-WT | none | <1 | 1.0 | 1.0 |
| WALBSP-05031 | I021V-A037T-S039E-I043V-A047V-P054T-T056Y-I080V-N085S-E087D-S099R-T114Q-S126A-D127E-F128G-N242D | 49 | 1.1 | 2.8 |
| WALBSP-05037 | A037T-S039E-I043V-A047V-P054T-T056E-I080V-N085S-E087D-S099R-T114Q-S126A-D127E-F128G-N242D | 51 | 1.1 | 4.3 |
| WALBSP-05042 | A037T-S039E-I043V-A047V-P054T-T056K-I080V-N085S-E087D-S099R-T114Q-S126A-D127E-F128G-N242D | 37 | 1.0 | 3.5 |
| WALBSP-05047 | A037T-S039E-I043V-A047V-P054T-T056Q-I080V-N085S-E087D-S099R-T114Q-S126A-D127E-F128G-N242D | 45 | 1.3 | 4.0 |
| WALBSP-05034 | A037T-S039E-I043V-A047V-P054T-T056A-I080V-N085S-E087D-S099R-T114Q-S126A-D127E-F128G-N242D | 46 | 1.4 | 3.9 |
| WALBSP-05035 | A037T-S039E-I043V-A047V-P054T-T056C-I080V-N085S-E087D-S099R-T114Q-S126A-D127E-F128G-N242D | 51 | 0.9 | 4.0 |

TABLE 11-continued

ADW Cleaning Performance of *B. gibsonii*-clade Subtilisin Variants measured on PAS-38 and DM10 stains using GSM-B detergent, expressed as PI compared to Bgi02446 parent, and stability in Tris-EDTA reported as percent remaining activity.

| *B gibsonii*-variants | Substitutions with respect to Bgi02446 wildtype | TRIS-EDTA | PAS-38 GSM-B | DM10 GSM-B |
|---|---|---|---|---|
| WALBSP-05036 | A037T-S039E-I043V-A047V-P054T-T056D-I080V-N085S-E087D-S099R-T114Q-S126A-D127E-F128G-N242D | 52 | 1.1 | 5.4 |
| WALBSP-05038 | A037T-S039E-I043V-A047V-P054T-T056F-I080V-N085S-E087D-S099R-T114Q-S126A-D127E-F128G-N242D | 46 | 1.1 | 2.6 |
| WALBSP-05040 | A037T-S039E-I043V-A047V-P054T-T056H-I080V-N085S-E087D-S099R-T114Q-S126A-D127E-F128G-N242D | 46 | 1.2 | 2.8 |
| WALBSP-05041 | A037T-S039E-I043V-A047V-P054T-T056I-I080V-N085S-E087D-S099R-T114Q-S126A-D127E-F128G-N242D | 48 | 1.1 | 3.1 |
| WALBSP-05043 | A037T-S039E-I043V-A047V-P054T-T056L-I080V-N085S-E087D-S099R-T114Q-S126A-D127E-F128G-N242D | 45 | 1.1 | 3.2 |
| WALBSP-05044 | A037T-S039E-I043V-A047V-P054T-T056M-I080V-N085S-E087D-S099R-T114Q-S126A-D127E-F128G-N242D | 47 | 1.2 | 3.5 |
| WALBSP-05045 | A037T-S039E-I043V-A047V-P054T-T056N-I080V-N085S-E087D-S099R-T114Q-S126A-D127E-F128G-N242D | 43 | 1.4 | 4.3 |
| WALBSP-05046 | A037T-S039E-I043V-A047V-P054T-T056P-I080V-N085S-E087D-S099R-T114Q-S126A-D127E-F128G-N242D | 46 | 1.1 | 3.6 |
| WALBSP-05049 | A037T-S039E-I043V-A047V-P054T-T056S-I080V-N085S-E087D-S099R-T114Q-S126A-D127E-F128G-N242D | 47 | 1.1 | 3.2 |
| WALBSP-05051 | A037T-S039E-I043V-A047V-P054T-T056V-I080V-N085S-E087D-S099R-T114Q-S126A-D127E-F128G-N242D | 44 | 1.2 | 3.7 |
| WALBSP-05052 | A037T-S039E-I043V-A047V-P054T-T056W-I080V-N085S-E087D-S099R-T114Q-S126A-D127E-F128G-N242D | 48 | 1.1 | 2.7 |
| WALBSP-05093 | A037Y-S039E-I043V-A047V-P054T-T056Y-I080V-N085S-E087D-S099R-T114Q-S126A-D127E-F128G-N242D | 46 | 1.1 | 3.0 |
| WALBSP-05120 | A037T-S039E-I043V-A047H-P054T-T056Y-I080V-N085S-E087D-S099R-T114Q-S126A-D127E-F128G-N242D | 46 | 1.2 | 2.8 |
| WALBSP-05075 | A037C-S039E-I043V-A047V-P054T-T056Y-I080V-N085S-E087D-S099R-T114Q-S126A-D127E-F128G-N242D | 56 | 0.9 | 4.1 |
| WALBSP-05076 | A037D-S039E-I043V-A047V-P054T-T056Y-I080V-N085S-E087D-S099R-T114Q-S126A-D127E-F128G-N242D | 56 | 0.9 | 4.7 |
| WALBSP-05079 | A037G-S039E-I043V-A047V-P054T-T056Y-I080V-N085S-E087D-S099R-T114Q-S126A-D127E-F128G-N242D | 53 | 1.2 | 2.5 |
| WALBSP-05080 | A037H-S039E-I043V-A047V-P054T-T056Y-I080V-N085S-E087D-S099R-T114Q-S126A-D127E-F128G-N242D | 52 | 1.3 | 2.2 |
| WALBSP-05085 | A037N-S039E-I043V-A047V-P054T-T056Y-I080V-N085S-E087D-S099R-T114Q-S126A-D127E-F128G-N242D | 46 | 1.0 | 3.1 |
| WALBSP-05086 | A037P-S039E-I043V-A047V-P054T-T056Y-I080V-N085S-E087D-S099R-T114Q-S126A-D127E-F128G-N242D | 50 | 1.1 | 2.9 |
| WALBSP-05087 | A037Q-S039E-I043V-A047V-P054T-T056Y-I080V-N085S-E087D-S099R-T114Q-S126A-D127E-F128G-N242D | 51 | 1.0 | 2.9 |
| WALBSP-05091 | A037V-S039E-I043V-A047V-P054T-T056Y-I080V-N085S-E087D-S099R-T114Q-S126A-D127E-F128G-N242D | 52 | 1.3 | 2.7 |
| WALBSP-05092 | A037W-S039E-I043V-A047V-P054T-T056Y-I080V-N085S-E087D-S099R-T114Q-S126A-D127E-F128G-N242D | 45 | 1.2 | 2.5 |
| WALBSP-05096 | A037T-S039D-I043V-A047V-P054T-T056Y-I080V-N085S-E087D-S099R-T114Q-S126A-D127E-F128G-N242D | 43 | 1.0 | 2.5 |
| WALBSP-05116 | A037T-S039E-I043V-A047D-P054T-T056Y-I080V-N085S-E087D-S099R-T114Q-S126A-D127E-F128G-N242D | 54 | 1.3 | 4.3 |

TABLE 11-continued

ADW Cleaning Performance of *B. gibsonii*-clade Subtilisin Variants measured on PAS-38 and DM10 stains using GSM-B detergent, expressed as PI compared to Bgi02446 parent, and stability in Tris-EDTA reported as percent remaining activity.

| *B gibsonii*-variants | Substitutions with respect to Bgi02446 wildtype | TRIS-EDTA | PAS-38 GSM-B | DM10 GSM-B |
|---|---|---|---|---|
| WALBSP-05117 | A037T-S039E-I043V-A047E-P054T-T056Y-I080V-N085S-E087D-S099R-T114Q-S126A-D127E-F128G-N242D | 55 | 1.2 | 3.9 |
| WALBSP-05118 | A037T-S039E-I043V-A047F-P054T-T056Y-I080V-N085S-E087D-S099R-T114Q-S126A-D127E-F128G-N242D | 43 | 1.2 | 3.2 |
| WALBSP-05121 | A037T-S039E-I043V-A047I-P054T-T056Y-I080V-N085S-E087D-S099R-T114Q-S126A-D127E-F128G-N242D | 49 | 1.2 | 3.0 |
| WALBSP-05124 | A037T-S039E-I043V-A047M-P054T-T056Y-I080V-N085S-E087D-S099R-T114Q-S126A-D127E-F128G-N242D | 50 | 1.4 | 3.8 |
| WALBSP-05125 | A037T-S039E-I043V-A047N-P054T-T056Y-I080V-N085S-E087D-S099R-T114Q-S126A-D127E-F128G-N242D | 44 | 1.1 | 3.6 |
| WALBSP-05127 | A037T-S039E-I043V-A047Q-P054T-T056Y-I080V-N085S-E087D-S099R-T114Q-S126A-D127E-F128G-N242D | 44 | 1.0 | 2.9 |
| WALBSP-05129 | A037T-S039E-I043V-A047S-P054T-T056Y-I080V-N085S-E087D-S099R-T114Q-S126A-D127E-F128G-N242D | 45 | 1.4 | 3.7 |
| WALBSP-05132 | A037T-S039E-I043V-A047W-P054T-T056Y-I080V-N085S-E087D-S099R-T114Q-S126A-D127E-F128G-N242D | 47 | 1.4 | 2.5 |
| WALBSP-05133 | A037T-S039E-I043V-A047Y-P054T-T056Y-I080V-N085S-E087D-S099R-T114Q-S126A-D127E-F128G-N242D | 48 | 1.0 | 2.7 |
| WALBSP-05137 | A037T-S039E-I043V-A047V-P054E-T056Y-I080V-N085S-E087D-S099R-T114Q-S126A-D127E-F128G-N242D | 54 | 0.8 | 3.6 |
| WALBSP-05139 | A037T-S039E-I043V-A047V-P054G-T056Y-I080V-N085S-E087D-S099R-T114Q-S126A-D127E-F128G-N242D | 49 | 1.1 | 2.6 |
| WALBSP-05141 | A037T-S039E-I043V-A047V-P054I-T056Y-I080V-N085S-E087D-S099R-T114Q-S126A-D127E-F128G-N242D | 51 | 1.0 | 2.6 |
| WALBSP-05143 | A037T-S039E-I043V-A047V-P054L-T056Y-I080V-N085S-E087D-S099R-T114Q-S126A-D127E-F128G-N242D | 49 | 1.0 | 2.8 |
| WALBSP-05147 | A037T-S039E-I043V-A047V-P054Q-T056Y-I080V-N085S-E087D-S099R-T114Q-S126A-D127E-F128G-N242D | 49 | 1.2 | 2.5 |
| WALBSP-05149 | A037T-S039E-I043V-A047V-P054S-T056Y-I080V-N085S-E087D-S099R-T114Q-S126A-D127E-F128G-N242D | 50 | 1.2 | 2.8 |
| WALBSP-05151 | A037T-S039E-I043V-A047V-P054V-T056Y-I080V-N085S-E087D-S099R-T114Q-S126A-D127E-F128G-N242D | 50 | 0.9 | 2.7 |
| WALBSP-05230 | A037T-S039E-I043V-A047V-P054T-T056Y-N074T-I080V-N085S-E087D-S099R-T114Q-S126A-D127E-F128G-N242D | 41 | 1.2 | 2.2 |
| WALBSP-05215 | A037T-S039E-I043V-A047V-P054T-T056Y-N074C-I080V-N085S-E087D-S099R-T114Q-S126A-D127E-F128G-N242D | 49 | 1.4 | 4.6 |
| WALBSP-05216 | A037T-S039E-I043V-A047V-P054T-T056Y-N074D-I080V-N085S-E087D-S099R-T114Q-S126A-D127E-F128G-N242D | 52 | 1.1 | 4.3 |
| WALBSP-05217 | A037T-S039E-I043V-A047V-P054T-T056Y-N074E-I080V-N085S-E087D-S099R-T114Q-S126A-D127E-F128G-N242D | 48 | 1.0 | 3.9 |
| WALBSP-05220 | A037T-S039E-I043V-A047V-P054T-T056Y-N074H-I080V-N085S-E087D-S099R-T114Q-S126A-D127E-F128G-N242D | 47 | 1.3 | 3.1 |
| WALBSP-05229 | A037T-S039E-I043V-A047V-P054T-T056Y-N074S-I080V-N085S-E087D-S099R-T114Q-S126A-D127E-F128G-N242D | 49 | 1.2 | 2.9 |
| WALBSP-05335 | A037T-S039E-I043V-A047V-P054T-T056Y-I080C-N085S-E087D-S099R-T114Q-S126A-D127E-F128G-N242D | 43 | 1.2 | 2.5 |
| WALBSP-05343 | A037T-S039E-I043V-A047V-P054T-T056Y-I080L-N085S-E087D-S099R-T114Q-S126A-D127E-F128G-N242D | 56 | 1.0 | 3.0 |

TABLE 11-continued

ADW Cleaning Performance of *B. gibsonii*-clade Subtilisin Variants measured on PAS-38 and DM10 stains using GSM-B detergent, expressed as PI compared to Bgi02446 parent, and stability in Tris-EDTA reported as percent remaining activity.

| *B gibsonii*-variants | Substitutions with respect to Bgi02446 wildtype | TRIS-EDTA | PAS-38 GSM-B | DM10 GSM-B |
|---|---|---|---|---|
| WALBSP-05436 | A037T-S039E-I043V-A047V-P054T-T056Y-I080V-N085D-E087D-S099R-T114Q-S126A-D127E-F128G-N242D | 55 | 1.0 | 4.8 |
| WALBSP-05437 | A037T-S039E-I043V-A047V-P054T-T056Y-I080V-N085E-E087D-S099R-T114Q-S126A-D127E-F128G-N242D | 57 | 1.1 | 3.9 |
| WALBSP-05440 | A037T-S039E-I043V-A047V-P054T-T056Y-I080V-N085H-E087D-S099R-T114Q-S126A-D127E-F128G-N242D | 52 | 1.1 | 3.0 |
| WALBSP-05443 | A037T-S039E-I043V-A047V-P054T-T056Y-I080V-N085L-E087D-S099R-T114Q-S126A-D127E-F128G-N242D | 50 | 1.2 | 3.2 |
| WALBSP-05446 | A037T-S039E-I043V-A047V-P054T-T056Y-I080V-N085P-E087D-S099R-T114Q-S126A-D127E-F128G-N242D | 44 | 1.3 | 2.5 |
| WALBSP-05447 | A037T-S039E-I043V-A047V-P054T-T056Y-I080V-N085Q-E087D-S099R-T114Q-S126A-D127E-F128G-N242D | 50 | 1.0 | 3.4 |
| WALBSP-05450 | A037T-S039E-I043V-A047V-P054T-T056Y-I080V-N085T-E087D-S099R-T114Q-S126A-D127E-F128G-N242D | 50 | 1.2 | 3.4 |
| WALBSP-05451 | A037T-S039E-I043V-A047V-P054T-T056Y-I080V-N085V-E087D-S099R-T114Q-S126A-D127E-F128G-N242D | 51 | 1.1 | 3.5 |
| WALBSP-05452 | A037T-S039E-I043V-A047V-P054T-T056Y-I080V-N085W-E087D-S099R-T114Q-S126A-D127E-F128G-N242D | 48 | 1.3 | 3.0 |
| WALBSP-05434 | A037T-S039E-I043V-A047V-P054T-T056Y-I080V-N085A-E087D-S099R-T114Q-S126A-D127E-F128G-N242D | 49 | 1.2 | 4.2 |
| WALBSP-05674 | A037T-S039E-I043V-A047V-P054T-T056Y-I080V-N085S-E087D-N097A-S099R-T114Q-S126A-D127E-F128G-N242D | 51 | 1.0 | 2.0 |
| WALBSP-05679 | A037T-S039E-I043V-A047V-P054T-T056Y-I080V-N085S-E087D-N097G-S099R-T114Q-S126A-D127E-F128G-N242D | 48 | 1.1 | ND |
| WALBSP-05689 | A037T-S039E-I043V-A047V-P054T-T056Y-I080V-N085S-E087D-N097S-S099R-T114Q-S126A-D127E-F128G-N242D | 51 | 0.9 | 2.3 |
| WALBSP-05717 | A037T-S039E-I043V-A047V-P054T-T056Y-I080V-N085S-E087D-S099E-T114Q-S126A-D127E-F128G-N242D | 64 | 0.4 | 0.8 |
| WALBSP-05724 | A037T-S039E-I043V-A047V-P054T-T056Y-I080V-N085S-E087D-S099M-T114Q-S126A-D127E-F128G-N242D | 66 | 0.9 | 3.8 |
| WALBSP-05731 | A037T-S039E-I043V-A047V-P054T-T056Y-I080V-N085S-E087D-S099V-T114Q-S126A-D127E-F128G-N242D | 65 | 1.0 | 2.8 |
| WALBSP-05754 | A037T-S039E-I043V-A047V-P054T-T056Y-I080V-N085S-E087D-S099R-S101A-T114Q-S126A-D127E-F128G-N242D | 44 | 1.1 | 2.8 |
| WALBSP-05777 | A037T-S039E-I043V-A047V-P054T-T056Y-I080V-N085S-E087D-S099R-V102E-T114Q-S126A-D127E-F128G-N242D | 47 | ND | 0.7 |
| WALBSP-05781 | A037T-S039E-I043V-A047V-P054T-T056Y-I080V-N085S-E087D-S099R-V102I-T114Q-S126A-D127E-F128G-N242D | 61 | 1.1 | 1.9 |
| WALBSP-06016 | A037T-S039E-I043V-A047V-P054T-T056Y-I080V-N085S-E087D-S099R-T114D-S126A-D127E-F128G-N242D | 64 | 1.1 | 2.8 |
| WALBSP-06017 | A037T-S039E-I043V-A047V-P054T-T056Y-I080V-N085S-E087D-S099R-T114E-S126A-D127E-F128G-N242D | 67 | 1.0 | 2.8 |
| WALBSP-06018 | A037T-S039E-I043V-A047V-P054T-T056Y-I080V-N085S-E087D-S099R-T114F-S126A-D127E-F128G-N242D | 46 | 1.5 | 2.5 |
| WALBSP-06019 | A037T-S039E-I043V-A047V-P054T-T056Y-I080V-N085S-E087D-S099R-T114G-S126A-D127E-F128G-N242D | 49 | 1.2 | 3.0 |
| WALBSP-06020 | A037T-S039E-I043V-A047V-P054T-T056Y-I080V-N085S-E087D-S099R-T114H-S126A-D127E-F128G-N242D | 53 | 1.1 | 2.4 |

TABLE 11-continued

ADW Cleaning Performance of *B. gibsonii*-clade Subtilisin Variants measured on PAS-38 and DM10 stains using GSM-B detergent, expressed as PI compared to Bgi02446 parent, and stability in Tris-EDTA reported as percent remaining activity.

| *B gibsonii*-variants | Substitutions with respect to Bgi02446 wildtype | TRIS-EDTA | PAS-38 GSM-B | DM10 GSM-B |
|---|---|---|---|---|
| WALBSP-06021 | A037T-S039E-I043V-A047V-P054T-T056Y-I080V-N085S-E087D-S099R-T114I-S126A-D127E-F128G-N242D | 50 | 1.3 | 2.4 |
| WALBSP-06023 | A037T-S039E-I043V-A047V-P054T-T056Y-I080V-N085S-E087D-S099R-T114L-S126A-D127E-F128G-N242D | 50 | 1.2 | 2.4 |
| WALBSP-06031 | A037T-S039E-I043V-A047V-P054T-T056Y-I080V-N085S-E087D-S099R-T114V-S126A-D127E-F128G-N242D | 54 | 1.1 | 2.4 |
| WALBSP-06068 | A037T-S039E-I043V-A047V-P054T-T056Y-I080V-N085S-E087D-S099R-T114Q-N116R-S126A-D127E-F128G-N242D | 30 | 1.2 | 1.6 |
| WALBSP-04915 | A037T-S039E-I043V-A047V-P054T-T056Y-I080V-N085S-E087D-S099R-T114Q-M122L-S126A-D127E-F128G-N242D | 59 | 1.0 | 2.0 |
| WALBSP-06258 | A037T-S039E-I043V-A047V-P054T-T056Y-I080V-N085S-E087D-S099R-T114Q-S126F-D127E-F128G-N242D | 64 | 1.1 | 0.5 |
| WALBSP-06260 | A037T-S039E-I043V-A047V-P054T-T056Y-I080V-N085S-E087D-S099R-T114Q-S126H-D127E-F128G-N242D | 41 | 1.0 | 2.4 |
| WALBSP-06265 | A037T-S039E-I043V-A047V-P054T-T056Y-I080V-N085S-E087D-S099R-T114Q-S126N-D127E-F128G-N242D | 40 | 1.2 | 2.8 |
| WALBSP-06294 | A037T-S039E-I043V-A047V-P054T-T056Y-I080V-N085S-E087D-S099R-T114Q-S126A-D127E-F128A-N242D | 55 | 1.0 | 1.3 |
| WALBSP-06296 | A037T-S039E-I043V-A047V-P054T-T056Y-I080V-N085S-E087D-S099R-T114Q-S126A-D127E-F128D-N242D | 72 | 1.1 | 2.8 |
| WALBSP-06297 | A037T-S039E-I043V-A047V-P054T-T056Y-I080V-N085S-E087D-S099R-T114Q-S126A-D127E-F128E-N242D | 82 | 0.9 | 3.0 |
| WALBSP-06889 | A037T-S039E-I043V-A047V-P054T-T056Y-I080V-N085S-E087D-S099R-T114Q-S126A-D127E-F128G-G157S-N242D | 44 | 1.1 | 2.6 |

Example 5

Laundry Cleaning Performance of *B. gibsonii*-Clade Subtilisins

The liquid laundry (HDL) cleaning performance of *B. gibsonii*-clade variants was measured on BMI swatches and Persil Non-Bio (boron-free) detergent as described on Example 2. The results are reported as PI (performance index) compared to the Bgi02446 wildtype parent and are shown on Tables 12 and 13.

TABLE 12

Liquid Laundry Cleaning Performance on BMI swatches and Persil Non-Bio Detergent of *B. gibsonii*-clade Subtilisin Variants, Expressed as PI compared to Bgi02446 parent.

| *B gibsonii*-clade variants | Substitutions with respect to Bgi02446 wildtype | HDL PI |
|---|---|---|
| Bgi02446 WT | | 1.0 |
| WALBSP-07063 | T056Y-S099R-S126A-D127E-F128G | 1.8 |
| WALBSP-07078 | S039E-I080V-S099R-S126A-D127E-F128G-M211L | 0.6 |
| WALBSP-07137 | S039E-P054T-S099R-S126A-D127E-F128G-M211L | 1.0 |
| WALBSP-07117 | S039E-I043V-S099R-S126A-D127E-F128G-M211L | 0.9 |
| WALBSP-07119 | S039E-N042R-S099R-S126A-D127E-F128G | 0.6 |
| WALBSP-07052 | S039E-I080V-S099R-S126A-D127E-F128G | 2.8 |
| WALBSP-07097 | S039E-S099R-S126A-D127E-F128G-M211L | 0.6 |
| WALBSP-07088 | S039E-N085S-S099R-S126A-D127E-F128G-M211L | 0.9 |
| WALBSP-07147 | S039E-T056Y-S099R-S126A-D127E-F128G-M211L | 0.8 |
| WALBSP-07127 | S039E-A047V-S099R-S126A-D127E-F128G-M211L | 0.9 |
| WALBSP-07149 | S039E-S099R-S126A-D127E-F128G-Y203W | 0.7 |

TABLE 12-continued

Liquid Laundry Cleaning Performance on BMI swatches and Persil Non-Bio Detergent of *B. gibsonii*-clade Subtilisin Variants, Expressed as PI compared to Bgi02446 parent.

| *B gibsonii*-clade variants | Substitutions with respect to Bgi02446 wildtype | HDL PI |
|---|---|---|
| WALBSP-07107 | A037T-S039E-S099R-S126A-D127E-F128G-M211L | 0.8 |
| WALBSP-07129 | S039E-S099R-S126A-D127E-F128G-V199I | 1.0 |
| WALBSP-07058 | A037T-S039E-I043V-A047V-P054T-T056Y-I080V-N085S-E087D-S099R-T114Q-S126A-D127E-F128G | 2.4 |
| WALBSP-07050 | S039E-I043V-A047V-P054T-T056Y-I080V-N085S-E087D-S099R-S126A-D127E-F128G-N242D | 2.6 |
| WALBSP-07040 | A037T-S039E-I043V-A047V-T056Y-I080V-N085S-E087D-S099R-T114Q-S126A-D127E-F128G | 2.2 |
| WALBSP-07014 | A037T-S039E-I043V-A047V-P054T-T056Y-I080V-N085S-E087D-S099R-S126A-D127E-F128G | 2.2 |
| WALBSP-07012 | S039E-I043V-S099R-S126A-D127E-F128G | 2.6 |
| WALBSP-07080 | S039E-S099R-S126A-D127E-F128G-N253D | 0.7 |
| WALBSP-07109 | T009E-S039E-S099R-S126A-D127E-F128G | 2.9 |
| WALBSP-07090 | S039E-S099R-S126A-D127E-F128G-S255W | 0.9 |
| WALBSP-07041 | A037T-S039E-I043V-A047V-P054T-T056Y-I080V-N085S-S099R-S126A-D127E-F128G-N242D | 2.7 |
| WALBSP-07001 | A037T-S039E-I043V-P054T-T056Y-I080V-N085S-E087D-S099R-S126A-D127E-F128G-N242D | 2.9 |
| WALBSP-07024 | S039E-I043V-A047V-T056Y-I080V-N085S-E087D-S099R-S126A-D127E-F128G-N242D | 2.7 |
| WALBSP-07068 | S039E-I043V-A047V-T056Y-I080V-N085S-E087D-S099R-T114Q-S126A-D127E-F128G-N242D | 2.4 |
| WALBSP-07042 | S039E-T056Y-S099R-S126A-D127E-F128G | 2.3 |
| WALBSP-07065 | A037T-S039E-I043V-A047V-T056Y-I080V-N085S-E087D-S099R-S126A-D127E-F128G | 2.6 |
| WALBSP-07027 | A037T-S039E-I043V-P054T-T056Y-I080V-N085S-E087D-S099R-T114Q-S126A-D127E-F128G-N242D | 2.8 |
| WALBSP-07019 | A037T-S039E-I043V-T056Y-I080V-N085S-E087D-S099R-T114Q-S126A-D127E-F128G-N242D | 2.7 |
| WALBSP-07029 | A037T-S039E-I043V-A047V-I080V-N085S-E087D-S099R-T114Q-S126A-D127E-F128G-N242D | 2.7 |
| WALBSP-07011 | A037T-S039E-I043V-A047V-P054T-I080V-N085S-E087D-S099R-S126A-D127E-F128G-N242D | 3.0 |
| WALBSP-07055 | A037T-S039E-I043V-A047V-T056Y-I080V-N085S-E087D-S099R-S126A-D127E-N242D | 2.3 |
| WALBSP-07054 | A037T-S039E-I043V-T056Y-I080V-N085S-E087D-S099R-S126A-D127E-F128G-N242D | 2.8 |
| WALBSP-07030 | A037T-S039E-I043V-A047V-T056Y-I080V-N085S-E087D-S099R-T114Q-S126A-D127E-N242D | 2.2 |
| WALBSP-07062 | S039E-N085S-S099R-S126A-D127E-F128G | 2.4 |
| WALBSP-07047 | A037T-S039E-I043V-A047V-P054T-I080V-N085S-E087D-S099R-T114Q-S126A-D127E-F128G-N242D | 2.9 |
| WALBSP-06998 | A037T-S039E-I043V-A047V-P054T-T056Y-I080V-N085S-S099R-T114Q-S126A-D127E-F128G-N242D | 2.7 |
| WALBSP-07048 | A037T-S039E-I043V-A047V-P054T-T056Y-I080V-N085S-E087D-S099R-T114Q-S126A-D127E-N242D | 2.1 |
| WALBSP-07051 | A037T-S039E-I043V-A047V-P054T-T056Y-I080V-N085S-E087D-S126A-D127E-F128G-N242D | 2.7 |
| WALBSP-07045 | A037T-S039E-I043V-A047V-T056Y-I080V-N085S-E087D-S099R-S126A-F128G-N242D | 2.7 |
| WALBSP-07049 | A037T-S039E-I043V-A047V-T056Y-I080V-E087D-S099R-T114Q-S126A-D127E-F128G-N242D | 2.3 |
| WALBSP-07003 | S039E-S099R-T114Q-S126A-D127E-F128G | 2.6 |
| WALBSP-07004 | A037T-S039E-I043V-A047V-P054T-T056Y-I080V-N085S-E087D-S099R-S126A-D127E-N242D | 2.3 |
| WALBSP-07000 | A037T-S039E-I043V-A047V-T056Y-I080V-N085S-E087D-S099R-S126A-D127E-F128G-N242D | 2.7 |
| WALBSP-07028 | A037T-S039E-I043V-A047V-P054T-T056Y-I080V-N085S-E087D-S099R-T114Q-D127E-F128G-N242D | 2.3 |
| WALBSP-07059 | A037T-S039E-I043V-A047V-T056Y-I080V-N085S-S099R-T114Q-S126A-D127E-F128G-N242D | 2.6 |
| WALBSP-07022 | S039E-A047V-S099R-S126A-D127E-F128G | 2.3 |
| WALBSP-07015 | A037T-S039E-I043V-A047V-T056Y-I080V-N085S-S099R-S126A-D127E-F128G-N242D | 2.7 |
| WALBSP-07033 | A037T-S039E-I043V-A047V-T056Y-S099R-T114Q-S126A-D127E-F128G | 2.3 |
| WALBSP-07031 | A037T-S039E-I043V-A047V-P054T-T056Y-I080V-E087D-S099R-S126A-D127E-F128G-N242D | 2.7 |
| WALBSP-07032 | S039E-P054T-S099R-S126A-D127E-F128G | 2.6 |
| WALBSP-04815 | A37T-S39E-I43V-A47V-P54T-T56Y-I80V-N85S-E87D-S99R-T114Q-S126A-D127E-F128G-N242D | 2.6 |
| WALBSP-07064 | A037T-S039E-I043V-A047V-I080V-N085S-E087D-S099R-S126A-D127E-F128G-N242D | 2.7 |

TABLE 12-continued

Liquid Laundry Cleaning Performance on BMI swatches and Persil Non-Bio Detergent of *B. gibsonii*-clade Subtilisin Variants, Expressed as PI compared to Bgi02446 parent.

| *B gibsonii*-clade variants | Substitutions with respect to Bgi02446 wildtype | HDL PI |
|---|---|---|
| WALBSP-07005 | A037T-S039E-I043V-A047V-T056Y-I080V-E087D-S099R-S126A-D127E-F128G-N242D | 2.8 |
| WALBSP-04170 | A037T-S039E-I043V-A047V-T056Y-I080V-N085S-E087D-S099R-T114Q-D127E-F128G-N242D | 2.8 |
| WALBSP-07061 | A037T-S039E-I043V-A047V-P054T-T056Y-I080V-N085S-E087D-S099R-D127E-F128G-N242D | 2.5 |
| WALBSP-07072 | S039E-E087D-S099R-S126A-D127E-F128G | 2.2 |
| WALBSP-07035 | A037T-S039E-I043V-A047V-T056Y-I080V-N085S-E087D-S099R-D127E-F128G-N242D | 2.7 |
| WALBSP-04704 | A037T-S039E-I043V-A047V-P054T-T056Y-I080V-N085S-E087D-S099R-T114Q-S126A-F128G-N242D | 2.7 |
| WALBSP-07002 | A037T-S039E-S099R-S126A-D127E-F128G | 2.5 |
| WALBSP-07067 | A037T-S039E-I043V-A047V-P054T-T056Y-I080V-E087D-S099R-T114Q-S126A-D127E-F128G-N242D | 2.3 |
| WALBSP-07018 | A037T-S039E-I043V-A047V-P054T-T056Y-I080V-N085S-E087D-S099R-S126A-D127E-F128G-N242D | 2.6 |
| WALBSP-07020 | A037T-S039E-I043V-A047V-T056Y-I080V-N085S-E087D-S099R-T114Q-S126A-F128G-N242D | 2.6 |
| WALBSP-07043 | A037T-S039E-I043V-A047V-T056Y-S099R-S126A-D127E-F128G | 2.2 |
| WALBSP-07023 | A037T-S039E-I043V-A047V-P054T-T056Y-S099R-T114Q-S126A-D127E-F128G | 2.8 |
| WALBSP-07070 | A037T-S039E-A047V-P054T-T056Y-I080V-N085S-E087D-S099R-S126A-D127E-F128G-N242D | 2.5 |
| WALBSP-07071 | A037T-S039E-I043V-A047V-P054T-T056Y-I080V-N085S-E087D-S099R-S126A-F128G-N242D | 2.6 |
| WALBSP-07008 | A037T-S039E-I043V-A047V-P054T-T056Y-I080V-N085S-E087D-T114Q-S126A-D127E-F128G-N242D | 3.1 |
| WALBSP-07025 | A037T-S039E-I043V-A047V-T056Y-I080V-N085S-E087D-S126A-D127E-F128G-N242D | 3.3 |
| WALBSP-07009 | A037T-S039E-A047V-T056Y-I080V-N085S-E087D-S099R-T114Q-S126A-D127E-F128G-N242D | 2.9 |
| WALBSP-07075 | S039E-S099R-S126A-D127E-F128G | 2.3 |
| WALBSP-07017 | A037T-S039E-A047V-P054T-T056Y-I080V-N085S-E087D-S099R-T114Q-S126A-D127E-F128G-N242D | 2.6 |
| WALBSP-07069 | A037T-S039E-I043V-A047V-T056Y-I080V-N085S-E087D-T114Q-S126A-D127E-F128G-N242D | 3.0 |
| WALBSP-07044 | A037T-S039E-A047V-T056Y-I080V-N085S-E087D-S099R-S126A-D127E-F128G-N242D | 2.7 |
| WALBSP-07100 | S039E-S099R-S126A-D127E-F128G-Q256E | 3.7 |
| WALBSP-07013 | S039E-S099R-S126A-D127E-F128G-N242D | 2.8 |
| WALBSP-07139 | S039E-S099R-S126A-D127E-F128G-Q200L | 0.6 |
| WALBSP-07077 | A037T-S039E-I043V-A047V-P054T-T056Y-S099R-T114Q-S126A-D127E-F128G-N242D | 2.6 |
| WALBSP-07087 | A037T-S039E-I043V-A047V-P054T-T056Y-S099R-S126A-D127E-F128G-N242D | 2.5 |
| WALBSP-07138 | S039E-N074D-I080V-S099R-S126A-D127E-F128G | 1.8 |
| WALBSP-07021 | A037T-S039E-I043V-A047V-P054T-T056Y-N085S-E087D-S099R-S126A-D127E-F128G-N242D | 2.7 |
| WALBSP-07039 | A037T-S039E-I043V-A047V-T056Y-N085S-E087D-S099R-T114Q-S126A-D127E-F128G-N242D | 2.7 |
| WALBSP-07053 | A037T-S039E-I043V-A047V | 2.4 |
| WALBSP-07073 | A037T-S039E-I043V-A047V-N242D | 2.9 |
| WALBSP-07118 | S039E-P054T-N074D-S099R-S126A-D127E-F128G | 2.3 |
| WALBSP-07108 | S039E-A047V-N074D-S099R-S126A-D127E-F128G | 1.7 |
| WALBSP-07057 | A037T-S039E-I043V-A047V-P054T-T056Y-N085S-E087D-S099R-T114Q-S126A-D127E-F128G-N242D | 2.8 |
| WALBSP-07089 | S039E-N074D-S099R-T114Q-S126A-D127E-F128G | 2.2 |
| WALBSP-07148 | S039E-N074D-N085S-S099R-S126A-D127E-F128G | 2.0 |
| WALBSP-07074 | A037T-S039E-I043V-A047V-T056Y-N085S-E087D-S099R-S126A-D127E-F128G-N242D | 2.5 |
| WALBSP-07079 | S039E-N074D-E087D-S099R-S126A-D127E-F128G | 1.8 |
| WALBSP-07098 | S039E-I043V-N074D-S099R-S126A-D127E-F128G | 1.9 |
| WALBSP-07128 | S039E-T056Y-N074D-S099R-S126A-D127E-F128G | 2.0 |
| WALBSP-07099 | S039E-N074D-S099R-S126A-D127E-F128G-N242D | 4.0 |

TABLE 13

Liquid Laundry Cleaning Performance of *B. gibsonii*-clade Subtilisin Variants measured on BMI stain in Persil Non-Bio detergent, expressed as PI compared to Bgi02446 parent.

| *B gibsonii*-variants | Substitutions with respect to Bgi02446 wildtype | BMI Persil |
|---|---|---|
| BG46 WT | | 1.0 |
| WALBSP-05031 | I021V-A037T-S039E-I043V-A047V-P054T-T056Y-I080V-N085S-E087D-S099R-T114Q-S126A-D127E-F128G-N242D | 1.8 |
| WALBSP-05037 | A037T-S039E-I043V-A047V-P054T-T056E-I080V-N085S-E087D-S099R-T114Q-S126A-D127E-F128G-N242D | 4.0 |
| WALBSP-05042 | A037T-S039E-I043V-A047V-P054T-T056K-I080V-N085S-E087D-S099R-T114Q-S126A-D127E-F128G-N242D | 3.3 |
| WALBSP-05047 | A037T-S039E-I043V-A047V-P054T-T056Q-I080V-N085S-E087D-S099R-T114Q-S126A-D127E-F128G-N242D | 2.4 |
| WALBSP-05034 | A037T-S039E-I043V-A047V-P054T-T056A-I080V-N085S-E087D-S099R-T114Q-S126A-D127E-F128G-N242D | 2.1 |
| WALBSP-05035 | A037T-S039E-I043V-A047V-P054T-T056C-I080V-N085S-E087D-S099R-T114Q-S126A-D127E-F128G-N242D | 2.4 |
| WALBSP-05036 | A037T-S039E-I043V-A047V-P054T-T056D-I080V-N085S-E087D-S099R-T114Q-S126A-D127E-F128G-N242D | 3.8 |
| WALBSP-05038 | A037T-S039E-I043V-A047V-P054T-T056F-I080V-N085S-E087D-S099R-T114Q-S126A-D127E-F128G-N242D | 2.2 |
| WALBSP-05040 | A037T-S039E-I043V-A047V-P054T-T056H-I080V-N085S-E087D-S099R-T114Q-S126A-D127E-F128G-N242D | 2.3 |
| WALBSP-05041 | A037T-S039E-I043V-A047V-P054T-T056I-I080V-N085S-E087D-S099R-T114Q-S126A-D127E-F128G-N242D | 2.2 |
| WALBSP-05043 | A037T-S039E-I043V-A047V-P054T-T056L-I080V-N085S-E087D-S099R-T114Q-S126A-D127E-F128G-N242D | 2.1 |
| WALBSP-05044 | A037T-S039E-I043V-A047V-P054T-T056M-I080V-N085S-E087D-S099R-T114Q-S126A-D127E-F128G-N242D | 1.8 |
| WALBSP-05045 | A037T-S039E-I043V-A047V-P054T-T056N-I080V-N085S-E087D-S099R-T114Q-S126A-D127E-F128G-N242D | 2.2 |
| WALBSP-05046 | A037T-S039E-I043V-A047V-P054T-T056P-I080V-N085S-E087D-S099R-T114Q-S126A-D127E-F128G-N242D | 1.9 |
| WALBSP-05049 | A037T-S039E-I043V-A047V-P054T-T056S-I080V-N085S-E087D-S099R-T114Q-S126A-D127E-F128G-N242D | 2.5 |
| WALBSP-05051 | A037T-S039E-I043V-A047V-P054T-T056V-I080V-N085S-E087D-S099R-T114Q-S126A-D127E-F128G-N242D | 2.4 |
| WALBSP-05052 | A037T-S039E-I043V-A047V-P054T-T056W-I080V-N085S-E087D-S099R-T114Q-S126A-D127E-F128G-N242D | 2.1 |
| WALBSP-05093 | A037Y-S039E-I043V-A047V-P054T-T056Y-I080V-N085S-E087D-S099R-T114Q-S126A-D127E-F128G-N242D | 1.6 |
| WALBSP-05120 | A037T-S039E-I043V-A047H-P054T-T056Y-I080V-N085S-E087D-S099R-T114Q-S126A-D127E-F128G-N242D | 2.5 |
| WALBSP-05075 | A037C-S039E-I043V-A047V-P054T-T056Y-I080V-N085S-E087D-S099R-T114Q-S126A-D127E-F128G-N242D | 2.7 |
| WALBSP-05076 | A037D-S039E-I043V-A047V-P054T-T056Y-I080V-N085S-E087D-S099R-T114Q-S126A-D127E-F128G-N242D | 2.7 |
| WALBSP-05079 | A037G-S039E-I043V-A047V-P054T-T056Y-I080V-N085S-E087D-S099R-T114Q-S126A-D127E-F128G-N242D | 1.6 |
| WALBSP-05080 | A037H-S039E-I043V-A047V-P054T-T056Y-I080V-N085S-E087D-S099R-T114Q-S126A-D127E-F128G-N242D | 1.8 |
| WALBSP-05085 | A037N-S039E-I043V-A047V-P054T-T056Y-I080V-N085S-E087D-S099R-T114Q-S126A-D127E-F128G-N242D | 1.9 |
| WALBSP-05086 | A037P-S039E-I043V-A047V-P054T-T056Y-I080V-N085S-E087D-S099R-T114Q-S126A-D127E-F128G-N242D | 1.9 |
| WALBSP-05087 | A037Q-S039E-I043V-A047V-P054T-T056Y-I080V-N085S-E087D-S099R-T114Q-S126A-D127E-F128G-N242D | 2.7 |
| WALBSP-05091 | A037V-S039E-I043V-A047V-P054T-T056Y-I080V-N085S-E087D-S099R-T114Q-S126A-D127E-F128G-N242D | 2.6 |
| WALBSP-05092 | A037W-S039E-I043V-A047V-P054T-T056Y-I080V-N085S-E087D-S099R-T114Q-S126A-D127E-F128G-N242D | 1.6 |
| WALBSP-05096 | A037T-S039D-I043V-A047V-P054T-T056Y-I080V-N085S-E087D-S099R-T114Q-S126A-D127E-F128G-N242D | 1.8 |
| WALBSP-05116 | A037T-S039E-I043V-A047D-P054T-T056Y-I080V-N085S-E087D-S099R-T114Q-S126A-D127E-F128G-N242D | 4.9 |
| WALBSP-05117 | A037T-S039E-I043V-A047E-P054T-T056Y-I080V-N085S-E087D-S099R-T114Q-S126A-D127E-F128G-N242D | 3.8 |
| WALBSP-05118 | A037T-S039E-I043V-A047F-P054T-T056Y-I080V-N085S-E087D-S099R-T114Q-S126A-D127E-F128G-N242D | 2.4 |
| WALBSP-05121 | A037T-S039E-I043V-A047I-P054T-T056Y-I080V-N085S-E087D-S099R-T114Q-S126A-D127E-F128G-N242D | 2.3 |
| WALBSP-05124 | A037T-S039E-I043V-A047M-P054T-T056Y-I080V-N085S-E087D-S099R-T114Q-S126A-D127E-F128G-N242D | 2.2 |
| WALBSP-05125 | A037T-S039E-I043V-A047N-P054T-T056Y-I080V-N085S-E087D-S099R-T114Q-S126A-D127E-F128G-N242D | 2.1 |
| WALBSP-05127 | A037T-S039E-I043V-A047Q-P054T-T056Y-I080V-N085S-E087D-S099R-T114Q-S126A-D127E-F128G-N242D | 2.3 |

TABLE 13-continued

Liquid Laundry Cleaning Performance of *B. gibsonii*-clade Subtilisin Variants measured on BMI stain in Persil Non-Bio detergent, expressed as PI compared to Bgi02446 parent.

| *B gibsonii*-variants | Substitutions with respect to Bgi02446 wildtype | BMI Persil |
|---|---|---|
| WALBSP-05129 | A037T-S039E-I043V-A047S-P054T-T056Y-I080V-N085S-E087D-S099R-T114Q-S126A-D127E-F128G-N242D | 2.8 |
| WALBSP-05132 | A037T-S039E-I043V-A047W-P054T-T056Y-I080V-N085S-E087D-S099R-T114Q-S126A-D127E-F128G-N242D | 2.5 |
| WALBSP-05133 | A037T-S039E-I043V-A047Y-P054T-T056Y-I080V-N085S-E087D-S099R-T114Q-S126A-D127E-F128G-N242D | 2.0 |
| WALBSP-05137 | A037T-S039E-I043V-A047V-P054E-T056Y-I080V-N085S-E087D-S099R-T114Q-S126A-D127E-F128G-N242D | 3.3 |
| WALBSP-05139 | A037T-S039E-I043V-A047V-P054G-T056Y-I080V-N085S-E087D-S099R-T114Q-S126A-D127E-F128G-N242D | 2.2 |
| WALBSP-05141 | A037T-S039E-I043V-A047V-P054I-T056Y-I080V-N085S-E087D-S099R-T114Q-S126A-D127E-F128G-N242D | 1.7 |
| WALBSP-05143 | A037T-S039E-I043V-A047V-P054L-T056Y-I080V-N085S-E087D-S099R-T114Q-S126A-D127E-F128G-N242D | 1.8 |
| WALBSP-05147 | A037T-S039E-I043V-A047V-P054Q-T056Y-I080V-N085S-E087D-S099R-T114Q-S126A-D127E-F128G-N242D | 1.7 |
| WALBSP-05149 | A037T-S039E-I043V-A047V-P054S-T056Y-I080V-N085S-E087D-S099R-T114Q-S126A-D127E-F128G-N242D | 1.9 |
| WALBSP-05151 | A037T-S039E-I043V-A047V-P054V-T056Y-I080V-N085S-E087D-S099R-T114Q-S126A-D127E-F128G-N242D | 1.9 |
| WALBSP-05230 | A037T-S039E-I043V-A047V-P054T-T056Y-N074T-I080V-N085S-E087D-S099R-T114Q-S126A-D127E-F128G-N242D | 2.0 |
| WALBSP-05215 | A037T-S039E-I043V-A047V-P054T-T056Y-N074C-I080V-N085S-E087D-S099R-T114Q-S126A-D127E-F128G-N242D | 2.7 |
| WALBSP-05216 | A037T-S039E-I043V-A047V-P054T-T056Y-N074D-I080V-N085S-E087D-S099R-T114Q-S126A-D127E-F128G-N242D | 2.8 |
| WALBSP-05217 | A037T-S039E-I043V-A047V-P054T-T056Y-N074E-I080V-N085S-E087D-S099R-T114Q-S126A-D127E-F128G-N242D | 2.7 |
| WALBSP-05220 | A037T-S039E-I043V-A047V-P054T-T056Y-N074H-I080V-N085S-E087D-S099R-T114Q-S126A-D127E-F128G-N242D | 2.1 |
| WALBSP-05229 | A037T-S039E-I043V-A047V-P054T-T056Y-N074S-I080V-N085S-E087D-S099R-T114Q-S126A-D127E-F128G-N242D | 1.8 |
| WALBSP-05335 | A037T-S039E-I043V-A047V-P054T-T056Y-I080C-N085S-E087D-S099R-T114Q-S126A-D127E-F128G-N242D | 1.8 |
| WALBSP-05343 | A037T-S039E-I043V-A047V-P054T-T056Y-I080L-N085S-E087D-S099R-T114Q-S126A-D127E-F128G-N242D | 1.8 |
| WALBSP-05436 | A037T-S039E-I043V-A047V-P054T-T056Y-I080V-N085D-E087D-S099R-T114Q-S126A-D127E-F128G-N242D | 2.5 |
| WALBSP-05437 | A037T-S039E-I043V-A047V-P054T-T056Y-I080V-N085E-E087D-S099R-T114Q-S126A-D127E-F128G-N242D | 2.8 |
| WALBSP-05440 | A037T-S039E-I043V-A047V-P054T-T056Y-I080V-N085H-E087D-S099R-T114Q-S126A-D127E-F128G-N242D | 2.3 |
| WALBSP-05443 | A037T-S039E-I043V-A047V-P054T-T056Y-I080V-N085L-E087D-S099R-T114Q-S126A-D127E-F128G-N242D | 2.0 |
| WALBSP-05446 | A037T-S039E-I043V-A047V-P054T-T056Y-I080V-N085P-E087D-S099R-T114Q-S126A-D127E-F128G-N242D | 2.3 |
| WALBSP-05447 | A037T-S039E-I043V-A047V-P054T-T056Y-I080V-N085Q-E087D-S099R-T114Q-S126A-D127E-F128G-N242D | 1.9 |
| WALBSP-05450 | A037T-S039E-I043V-A047V-P054T-T056Y-I080V-N085T-E087D-S099R-T114Q-S126A-D127E-F128G-N242D | 2.5 |
| WALBSP-05451 | A037T-S039E-I043V-A047V-P054T-T056Y-I080V-N085V-E087D-S099R-T114Q-S126A-D127E-F128G-N242D | 2.2 |
| WALBSP-05452 | A037T-S039E-I043V-A047V-P054T-T056Y-I080V-N085W-E087D-S099R-T114Q-S126A-D127E-F128G-N242D | 1.7 |
| WALBSP-05434 | A037T-S039E-I043V-A047V-P054T-T056Y-I080V-N085A-E087D-S099R-T114Q-S126A-D127E-F128G-N242D | 1.6 |
| WALBSP-05674 | A037T-S039E-I043V-A047V-P054T-T056Y-I080V-N085S-E087D-N097A-S099R-T114Q-S126A-D127E-F128G-N242D | 1.2 |
| WALBSP-05679 | A037T-S039E-I043V-A047V-P054T-T056Y-I080V-N085S-E087D-N097G-S099R-T114Q-S126A-D127E-F128G-N242D | 1.8 |
| WALBSP-05689 | A037T-S039E-I043V-A047V-P054T-T056Y-I080V-N085S-E087D-N097S-S099R-T114Q-S126A-D127E-F128G-N242D | 1.8 |
| WALBSP-05717 | A037T-S039E-I043V-A047V-P054T-T056Y-I080V-N085S-E087D-S099E-T114Q-S126A-D127E-F128G-N242D | 6.7 |
| WALBSP-05724 | A037T-S039E-I043V-A047V-P054T-T056Y-I080V-N085S-E087D-S099M-T114Q-S126A-D127E-F128G-N242D | 4.3 |
| WALBSP-05731 | A037T-S039E-I043V-A047V-P054T-T056Y-I080V-N085S-E087D-S099V-T114Q-S126A-D127E-F128G-N242D | 4.2 |
| WALBSP-05754 | A037T-S039E-I043V-A047V-P054T-T056Y-I080V-N085S-E087D-S099R-S101A-T114Q-S126A-D127E-F128G-N242D | 1.7 |
| WALBSP-05777 | A037T-S039E-I043V-A047V-P054T-T056Y-I080V-N085S-E087D-S099R-V102E-T114Q-S126A-D127E-F128G-N242D | 8.4 |
| WALBSP-05781 | A037T-S039E-I043V-A047V-P054T-T056Y-I080V-N085S-E087D-S099R-V102I-T114Q-S126A-D127E-F128G-N242D | 1.6 |

TABLE 13-continued

Liquid Laundry Cleaning Performance of *B. gibsonii*-clade Subtilisin Variants measured on BMI stain in Persil Non-Bio detergent, expressed as PI compared to Bgi02446 parent.

| *B gibsonii*-variants | Substitutions with respect to Bgi02446 wildtype | BMI Persil |
|---|---|---|
| WALBSP-06016 | A037T-S039E-I043V-A047V-P054T-T056Y-I080V-N085S-E087D-S099R-T114D-S126A-D127E-F128G-N242D | 2.8 |
| WALBSP-06017 | A037T-S039E-I043V-A047V-P054T-T056Y-I080V-N085S-E087D-S099R-T114E-S126A-D127E-F128G-N242D | 2.9 |
| WALBSP-06018 | A037T-S039E-I043V-A047V-P054T-T056Y-I080V-N085S-E087D-S099R-T114F-S126A-D127E-F128G-N242D | 1.7 |
| WALBSP-06019 | A037T-S039E-I043V-A047V-P054T-T056Y-I080V-N085S-E087D-S099R-T114G-S126A-D127E-F128G-N242D | 1.9 |
| WALBSP-06020 | A037T-S039E-I043V-A047V-P054T-T056Y-I080V-N085S-E087D-S099R-T114H-S126A-D127E-F128G-N242D | 1.6 |
| WALBSP-06021 | A037T-S039E-I043V-A047V-P054T-T056Y-I080V-N085S-E087D-S099R-T114I-S126A-D127E-F128G-N242D | 1.8 |
| WALBSP-06023 | A037T-S039E-I043V-A047V-P054T-T056Y-I080V-N085S-E087D-S099R-T114L-S126A-D127E-F128G-N242D | 1.7 |
| WALBSP-06031 | A037T-S039E-I043V-A047V-P054T-T056Y-I080V-N085S-E087D-S099R-T114V-S126A-D127E-F128G-N242D | 2.0 |
| WALBSP-06068 | A037T-S039E-I043V-A047V-P054T-T056Y-I080V-N085S-E087D-S099R-T114Q-N116R-S126A-D127E-F128G-N242D | 1.2 |
| WALBSP-04915 | A037T-S039E-I043V-A047V-P054T-T056Y-I080V-N085S-E087D-S099R-T114Q-M122L-S126A-D127E-F128G-N242D | 1.8 |
| WALBSP-06258 | A037T-S039E-I043V-A047V-P054T-T056Y-I080V-N085S-E087D-S099R-T114Q-S126F-D127E-F128G-N242D | 1.9 |
| WALBSP-06260 | A037T-S039E-I043V-A047V-P054T-T056Y-I080V-N085S-E087D-S099R-T114Q-S126H-D127E-F128G-N242D | 2.0 |
| WALBSP-06265 | A037T-S039E-I043V-A047V-P054T-T056Y-I080V-N085S-E087D-S099R-T114Q-S126N-D127E-F128G-N242D | 2.8 |
| WALBSP-06294 | A037T-S039E-I043V-A047V-P054T-T056Y-I080V-N085S-E087D-S099R-T114Q-S126A-D127E-F128A-N242D | 1.0 |
| WALBSP-06296 | A037T-S039E-I043V-A047V-P054T-T056Y-I080V-N085S-E087D-S099R-T114Q-S126A-D127E-F128D-N242D | 4.5 |
| WALBSP-06297 | A037T-S039E-I043V-A047V-P054T-T056Y-I080V-N085S-E087D-S099R-T114Q-S126A-D127E-F128E-N242D | 3.9 |
| WALBSP-06889 | A037T-S039E-I043V-A047V-P054T-T056Y-I080V-N085S-E087D-S099R-T114Q-S126A-D127E-F128G-G157S-N242D | 2.4 |

We claim:

1. A subtilisin variant comprising an amino acid sequence that is at least 90% identical to the amino acid sequence set forth in SEQ ID NO: 1, wherein the variant has the substitutions 5039E-5099R-S126A-D127E-F128G numbered by correspondence with the amino acid sequence of SEQ ID NO:1, and wherein the variant has a blood/milk/ink on cotton (BMI), egg, and/or crème brûlée stain cleaning PI>1 when compared to SEQ ID NO:1.

2. The subtilisin variant of claim 1, wherein the variant has combinations of mutations selected from the group consisting of:

S039E-S099R-S126A-D127E-F128G-M211L, 5039E-S099R-S126A-D127E-F128G-N242D, 5039E-S099R-S126A-D127E-F128G-N253D, 5039E-S099R-S126A-D127E-F128G-Q200L, 5039E-S099R-S126A-D127E-F128G-Q256E, 5039E-S099R-S126A-D127E-F128G-S255W, 5039E-5099R-S126A-D127E-F128G-V199I, S039E-5099R-S126A-D127E-F128G-Y203W, 5039E-5099R-T1140-S126A-D127E-F128G, 5039E-T056Y-N074D-S099R-S126A-D127E-F128G, 5039E-T056Y-S099R-S126A-D127E-F128G, 5039E-T056Y-S099R-S126A-D127E-F128G-M211L, and T009E-5039E-5099R-S126A-D127E-F128G, numbered by correspondence with the amino acid sequence of SEQ ID NO:1.

3. The subtilisin variant of claim 1, wherein the variant comprises an amino acid sequence with 91%, 92%, 93%, 94%, 95%, 96%, 97%, 98%, 99% or less than 100% amino acid sequence identity to the amino acid sequence of SEQ ID NO:1.

4. A composition comprising the substilisin variant of claim 1.

5. The composition of claim 4, wherein the composition is selected from an enzyme composition and a detergent composition.

6. The composition of claim 5, wherein the detergent composition is selected from a laundry detergent, a fabric softening detergent, a dishwashing detergent, and a hard-surface cleaning detergent.

7. The composition of claim 4, further comprising (i) one or more enzymes selected from acyl transferases, amylases, alpha-amylases, beta-amylases, alpha-galactosidases, arabinases, arabinosidases, aryl esterases, beta-galactosidases, beta-glucanases, carrageenases, catalases, chondroitinases, cutinases, endo-beta-mannanases, exo-beta-mannanases, esterases, exo-mannanases, galactanases, glucoamylases, hemicellulases, hyaluronidases, keratinases, lactases, ligninases, lipases, lipolytic enzymes, lipoxygenases, mannanases, metalloproteases, oxidases, oxidoreductases, pectate lyases, pectin acetyl esterases, pectinases, pentosanases, perhydrolases, peroxidases, phenoloxidases, phosphatases, phospholipases, polyesterases, polygalacturonases, proteases, pullulanases, reductases, rhamnogalacturonases, cellulases, beta-glucanases, tannases, transglutaminases, xylan acetyl-esterases, xylanases, and xylosidases; (ii) one or more surfactants; (iii) one or more ions selected from calcium and zinc; (iv) one or more adjunct material; (v) one or more stabilizers; (vi) one or more bleaching agents and/or (vii) combinations thereof.

8. The composition of claim 4, wherein the composition is phosphate-free or contains phosphate and/or is boron free or contains boron.

9. The composition of claim 4, wherein the composition is granular, powder, solid, bar, liquid, tablet, gel, paste and/or a unit dose composition.

* * * * *

SEQUENCE LISTING

```
<160> NUMBER OF SEQ ID NOS: 13

<210> SEQ ID NO 1
<211> LENGTH: 269
<212> TYPE: PRT
<213> ORGANISM: Bacillus gibsonii

<400> SEQUENCE: 1

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125
```

```
Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265


<210> SEQ ID NO 2
<211> LENGTH: 1052
<212> TYPE: DNA
<213> ORGANISM: Bacillus subtilis

<400> SEQUENCE: 2

gcaaaacgcg gatcattgga agagacgacc gtacccgcag catcaatgcc taaaataagc      60

ggatactctc tgacgatatt gcctcctgct tttccggcca gaccatcttt gtaattaatg     120

ccggaataag caactttaat caggacacca tccttcggca aatcctctgt tgatatggtt     180

ttcacatgga ctgaaacatc atcggcattt ttttctgcct gcaaggcttg aaataacgtt     240

gacattcggc acactccttt tcatttatat cgtaaccgaa gaacgttcaa aaaaccaaat     300

catcaagccg ccattttcac ttcgccggca cattgagaca ataatggaca aatccggtat     360

cctcttcata gccgttttgc tcatacaagc ttcttgcctt ccggttgtgg tgctcagtct     420

gaagtgttaa acattttgcc ccgttttgcc ctgcataatc ctttgcggca gaaagcagcc     480

ggccgccggc tccctttgta cgcgcatgag gaacgacaaa taagtcattt aatatgtata     540

tccttttcat tgacacagaa gaaaacgttg gatagagctg ggtaaagcct atgaattctc     600

cattttcttc tgctatcaaa ataacagact cgtgattttc caaacgagct ttcaaaaaag     660

cctctgcccc ttgcaaatcg gatgcctgtc tataaaattc ccgatattgg ttaaacagcg     720

gcgcaatggc ggccgcatct gatgtctttg cttggcgaat gttcatctta tttcttcctc     780

cctctcaata attttttcat tctatccctt ttctgtaaag tttatttttc agaatacttt     840

tatcatcatg ctttgaaaaa atatcacgat aatatccatt gttctcacgg aagcacacgc     900

gtcgctgata aacagctgac atcaactaaa agcttcatta aatactttga aaaaagttgt     960

tgacttaaaa gaagctaaat gttatagtaa taaaacagaa tagtctttta agtaagtcta    1020

ctctgaattt ttttaaaagg agagggtaaa ga                                  1052


<210> SEQ ID NO 3
<211> LENGTH: 87
<212> TYPE: DNA
<213> ORGANISM: Bacillus subtilis

<400> SEQUENCE: 3
```

gtgagaagca aaaaattgtg gatcagcttg ttgtttgcgt taacgttaat ctttacgatg 60
gcgttcagca acatgtctgc gcaggct 87

<210> SEQ ID NO 4
<211> LENGTH: 252
<212> TYPE: DNA
<213> ORGANISM: Bacillus lentus

<400> SEQUENCE: 4
gctgaagaag caaaagaaaa atatttaatt ggctttaatg agcaggaagc tgtcagtgag 60
tttgtagaac aagtagaggc aaatgacgag gtcgccattc tctctgagga agaggaagtc 120
gaaattgaat tgcttcatga atttgaaacg attcctgttt tatccgttga gttaagccca 180
gaagatgtgg acgcgcttga actcgatcca gcgatttctt atattgaaga ggatgcagaa 240
gtaacgacaa tg 252

<210> SEQ ID NO 5
<211> LENGTH: 810
<212> TYPE: DNA
<213> ORGANISM: Artificial Sequence
<220> FEATURE:
<223> OTHER INFORMATION: variant DNA sequence

<400> SEQUENCE: 5
caacaaacag tgccatgggg aattactcgt gtgcaagccc cagctgttca taaccgtgga 60
attacaggtt ctggtgtaag agttgctatc ctcgattcag gtatttccac acatgaagac 120
ttaaatgttc gtggtggcgt tagctttgta ccaggggaac caacgtatgc tgatttaaat 180
gggcatggca cgcatgtggc tgggacggta gctgctttaa acaattcgat tggcgttgtt 240
ggcgtagcac cgtcagcgga tctatacgct gttaaagtat taggggcgaa tggtagaggt 300
tcggtcagcg ggattgccca aggattggaa tgggcagcac aaaataacat gcacattgct 360
aatatgagtt taggaacaga tgcaccaagt tctacacttg agcgtgctgt taattatgcg 420
acttctagag atgttcttgt tattgcggca actgggaata acggttctgg ctcagtaggc 480
tatccggccc gttatgcgaa cgcaatggca gtcggagcta ctgaccaaaa caacagacgc 540
gccaactttt cacagtatgg cacggggatt gacattgtcg caccaggtgt aaacgtgcag 600
agcacatacc caggtaaccg ttatgtgagc atgaacggta catcgatggc tactcctcat 660
gttgcaggtg cagcagccct tgttaaacaa cgctatccat cttggaatgc gactcaaatc 720
cgcgaccatc taaagaatac ggcaacgaat ttaggaaact cttcacaatt tggaagcgga 780
cttgtcaatg cagaagcggc aacacgctaa 810

<210> SEQ ID NO 6
<211> LENGTH: 254
<212> TYPE: DNA
<213> ORGANISM: Bacillus amyloliquefaciens

<400> SEQUENCE: 6
tctagataca taaaaaaccg gccttggccc cgccggtttt ttattatttt tcttcctccg 60
catgttcaat ccgctccata atcgacggat ggctccctct gaaaatttta acgagaaacg 120
gcgggttgac ccggctcagt cccgtaacgg ccaagtcctg aaacgtctca atcgccgctt 180
cccggtttcc ggtcagctca atgccgtaac ggtcggcggc gttttcctga taccgggaga 240
cggcattcgt aatc 254

<210> SEQ ID NO 7
<211> LENGTH: 855
<212> TYPE: DNA
<213> ORGANISM: Staphylococcus aureus

<400> SEQUENCE: 7

```
ttagtgacat tagaaaaccg actgtaaaaa gtacagtcgg cattatctca tattataaaa     60

gccagtcatt aggcctatct gacaattcct gaatagagtt cataaacaat cctgcatgat    120

aaccatcaca aacagaatga tgtacctgta aagatagcgg taaatatatt gaattacctt    180

tattaatgaa ttttcctgct gtaataatgg gtagaaggta attactatta ttattgatat    240

ttaagttaaa cccagtaaat gaagtccatg gaataataga aagagaaaaa gcattttcag    300

gtataggtgt tttgggaaac aatttccccg aaccattata tttctctaca tcagaaaggt    360

ataaatcata aaactctttg aagtcattct ttacaggagt ccaaatacca gagaatgttt    420

tagatacacc atcaaaaatt gtataaagtg gctctaactt atcccaataa cctaactctc    480

cgtcgctatt gtaaccagtt ctaaaagctg tatttgagtt tatcaccctt gtcactaaga    540

aaataaatgc agggtaaaat ttatatcctt cttgttttat gtttcggtat aaaacactaa    600

tatcaatttc tgtggttata ctaaaagtcg tttgttggtt caaataatga ttaaatatct    660

cttttctctt ccaattgtct aaatcaattt tattaaagtt catttgatat gcctcctaaa    720

tttttatcta aagtgaattt aggaggctta cttgtctgct ttcttcatta gaatcaatcc    780

ttttttaaaa gtcaatatta ctgtaacata aatatatatt ttaaaaatat cccactttat    840

ccaatttcg tttgt                                                       855
```

<210> SEQ ID NO 8
<211> LENGTH: 269
<212> TYPE: PRT
<213> ORGANISM: Artificial Sequence
<220> FEATURE:
<223> OTHER INFORMATION: variant of Bgi02446

<400> SEQUENCE: 8

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Tyr Ala Asp Leu Asn Gly His Gly Thr
    50                  55                  60

His Val Ala Gly Thr Val Ala Ala Leu Asn Asn Ser Ile Gly Val Val
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Gln Asn Asn Met His Ile Ala Asn Met Ser Leu Gly Thr Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
```

```
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asp His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 9
<211> LENGTH: 994
<212> TYPE: DNA
<213> ORGANISM: Artificial Sequence
<220> FEATURE:
<223> OTHER INFORMATION: 3' flanking region

<400> SEQUENCE: 9

```
tcagccttat tctcctgata acgcgagaca gcattagaaa aaggcgtaac cgcaaagctc     60

aaaacagaaa acaaaagcaa taacagcgga agtgccgcaa gatcatgccg cccttctaaa    120

tgaaacatgc tgcgggttag gcgaaccgtc cgcttgtaaa gcttatcaat gacataaaat    180

ccggcgagcg acacgagcaa atagccagcc agaccgatgt aaacgtgctt catgacataa    240

tggcccattt cgtggcccat aataaacaga atttctgaat cgtcaagttt gttcagcgtc    300

gtatcccaca atacaatccg tttattggcc ccaattcctg taacataggc attcagcgca    360

tttgtttttt ctgacatgtt cacttcatat acatggtcag ccggaatatt ggcttcatct    420

gccagctcta aaattttgct ttcaagctct ttgtttttca gcggataaaa atcattgtat    480

aaaggatcga taatgaccgg ctgaataaaa aacagaaaca gcgaaaacgg cactgttaac    540

agccaggcgt ataaccacca tttttttca tgccttttga tcagccaata aaaaacgaga    600

acgcaaagcg taaagattgg aaagctgatc caaaagctga taacctgatc cttagcccag    660

ctggccgttg tctgtgtgga aatgttatag tcaagcgata cttgatagcc tatccaatct    720

aaaggcagcg tcaccaatgt tgtaatcagc gaaagcacaa acacaaaacc aacggtctgc    780

aaaaaccgaa aaggcacggc cgcttcgatc catttcttga ttttctttga aacaccgctg    840

acaagcagaa caaaaaacag aaaccaatca agtggtaccc cgataaaaaa taaaaaattc    900

ttgacattcg aatactgctc ggccactgcc aactcagacg gcttcatgaa agaagccgga    960

tcagcctgcg tccctttcac ggcttccggt attg                                994
```

<210> SEQ ID NO 10
<211> LENGTH: 29
<212> TYPE: PRT
<213> ORGANISM: Bacillus subtilis

<400> SEQUENCE: 10

```
Val Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala
            20                  25
```

<210> SEQ ID NO 11
<211> LENGTH: 84
<212> TYPE: PRT
<213> ORGANISM: Bacillus lentus

<400> SEQUENCE: 11

```
Ala Glu Glu Ala Lys Glu Lys Tyr Leu Ile Gly Phe Asn Glu Gln Glu
1               5                   10                  15

Ala Val Ser Glu Phe Val Glu Gln Val Glu Ala Asn Asp Glu Val Ala
            20                  25                  30

Ile Leu Ser Glu Glu Glu Glu Val Glu Ile Glu Leu Leu His Glu Phe
        35                  40                  45

Glu Thr Ile Pro Val Leu Ser Val Glu Leu Ser Pro Glu Asp Val Asp
    50                  55                  60

Ala Leu Glu Leu Asp Pro Ala Ile Ser Tyr Ile Glu Glu Asp Ala Glu
65                  70                  75                  80

Val Thr Thr Met
```

<210> SEQ ID NO 12
<211> LENGTH: 602
<212> TYPE: DNA
<213> ORGANISM: Bacillus subtilis

<400> SEQUENCE: 12

```
tccattttct tctgctatca aaataacaga ctcgtgattt tccaaacgag ctttcaaaaa     60

agcctctgcc ccttgcaaat cggatgcctg tctataaaat tcccgatatt ggttaaacag    120

cggcgcaatg gcggccgcat ctgatgtctt tgcttggcga atgttcatct tatttcttcc    180

tccctctcaa taattttttc attctatccc ttttctgtaa agtttatttt tcagaatact    240

tttatcatca tgctttgaaa aaatatcacg ataatatcca ttgttctcac ggaagcacac    300

gcaggtcatt tgaacgaatt ttttcgacag gaatttgccg ggactcagga gcatttaacc    360

taaaaaagca tgacatttca gcataatgaa catttactca tgtctatttt cgttcttttc    420

tgtatgaaaa tagttatttc gagtctctac ggaaatagcg agagatgata tacctaaata    480

gagataaaat catctcaaaa aaatgggtct actaaaatat tattccatct attacaataa    540

attcacagaa tagtctttta agtaagtcta ctctgaattt ttttaaaagg agagggtaaa    600

ga                                                                   602
```

<210> SEQ ID NO 13
<211> LENGTH: 269
<212> TYPE: PRT
<213> ORGANISM: Bacillus lentus

<400> SEQUENCE: 13

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95
```

-continued

```
Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```